US008518085B2

(12) United States Patent
Winslow et al.

(10) Patent No.: US 8,518,085 B2
(45) Date of Patent: Aug. 27, 2013

(54) ADAPTIVE SPINAL ROD AND METHODS FOR STABILIZATION OF THE SPINE

(75) Inventors: Charles J. Winslow, Walnut Creek, CA (US); Ken Y. Hsu, San Francisco, CA (US); James F. Zucherman, San Francisco, CA (US); Steven T. Mitchell, Pleasant Hill, CA (US); John J. Flynn, Walnut Creek, CA (US)

(73) Assignee: Spartek Medical, Inc., Concord, CA (US)

( * ) Notice: Subject to any disclaimer, the term of this patent is extended or adjusted under 35 U.S.C. 154(b) by 265 days.

(21) Appl. No.: 13/014,868

(22) Filed: Jan. 27, 2011

(65) Prior Publication Data
US 2011/0307013 A1 Dec. 15, 2011

Related U.S. Application Data

(60) Provisional application No. 61/353,508, filed on Jun. 10, 2010, provisional application No. 61/435,961, filed on Jan. 25, 2011.

(51) Int. Cl.
A61B 17/70 (2006.01)

(52) U.S. Cl.
USPC ............................ 606/265; 606/256; 606/259

(58) Field of Classification Search
CPC ........... A61B 17/7002; A61B 17/7014; A61B 17/7019; A61B 17/702; A61B 17/7023; A61B 17/7025
USPC ................. 606/251–253, 256–259, 264, 265
See application file for complete search history.

(56) References Cited

U.S. PATENT DOCUMENTS

| 4,041,939 | A | 8/1977 | Hall ................................. 128/69 |
| 4,065,817 | A | 1/1978 | Branemark et al. ............. 3/1.91 |
| 4,274,401 | A | 6/1981 | Miskew |
| 4,347,845 | A | 9/1982 | Mayfield ....................... 128/303 |
| 4,369,770 | A | 1/1983 | Bacal et al. ..................... 128/69 |
| 4,382,438 | A | 5/1983 | Jacobs ............................ 128/69 |
| 4,409,968 | A | 10/1983 | Drummond .................... 128/69 |
| 4,411,259 | A | 10/1983 | Drummond .................... 128/69 |
| 4,422,451 | A | 12/1983 | Kalamchi ....................... 128/69 |

(Continued)

FOREIGN PATENT DOCUMENTS

| DE | 2649042 B1 | 10/1976 |
| DE | 3639810 A1 | 5/1988 |

(Continued)

OTHER PUBLICATIONS

International Search Report for PCT/US2011/039144 dated Feb. 29, 2012, 11 pages.

(Continued)

Primary Examiner — Ellen C Hammond
(74) Attorney, Agent, or Firm — Fliesler Meyer LLP

(57) ABSTRACT

An adaptive spinal rod is provided for connecting levels of an adaptive stabilization system to support the spine while providing for the preservation of spinal motion. Embodiments of the adaptive stabilization rod include a ball having an anchor system, a deflection system, a vertical rod system and a connection system. The deflection system provides adaptive stabilization and load-sharing. The adaptive spinal rod connects different levels of the construct in a multilevel construct. The adaptive spinal rod cooperates with the deflection system to further reduce stress exerted upon the bone anchors and spinal anatomy.

18 Claims, 34 Drawing Sheets

(56) References Cited

U.S. PATENT DOCUMENTS

| | | | |
|---|---|---|---|
| 4,479,491 A | 10/1984 | Martin | 128/92 |
| 4,567,885 A | 2/1986 | Androphy | 128/92 |
| 4,573,454 A | 3/1986 | Hoffman | 128/69 |
| 4,604,995 A | 8/1986 | Stephens et al. | 128/69 |
| 4,611,580 A | 9/1986 | Wu | 128/69 |
| 4,611,581 A | 9/1986 | Steffee | 128/69 |
| 4,611,582 A | 9/1986 | Duff | 128/69 |
| 4,641,636 A | 2/1987 | Cotrel | 128/69 |
| 4,648,388 A | 3/1987 | Steffee | 128/69 |
| 4,653,481 A | 3/1987 | Howland et al. | 128/69 |
| 4,653,489 A | 3/1987 | Tronzo | 128/92 |
| 4,655,199 A | 4/1987 | Steffee | 128/69 |
| 4,658,809 A | 4/1987 | Ulrich et al. | 128/92 |
| 4,696,290 A | 9/1987 | Steffee | 128/69 |
| 4,719,905 A | 1/1988 | Steffee | 128/69 |
| 4,763,644 A | 8/1988 | Webb | 128/69 |
| 4,773,402 A | 9/1988 | Asher et al. | 128/69 |
| 4,805,602 A | 2/1989 | Puno et al. | 128/69 |
| 4,815,453 A | 3/1989 | Cotrel | 128/69 |
| 4,887,595 A | 12/1989 | Heinig et al. | 606/61 |
| 4,913,134 A | 4/1990 | Luque | 128/69 |
| 4,946,458 A | 8/1990 | Harms et al. | 606/61 |
| 4,950,269 A | 8/1990 | Gaines, Jr. | 606/61 |
| 4,955,885 A | 9/1990 | Meyers | 606/53 |
| 4,987,892 A | 1/1991 | Krag et al. | 606/61 |
| 5,005,562 A | 4/1991 | Cotrel | 128/69 |
| 5,024,213 A | 6/1991 | Asher et al. | 128/69 |
| 5,030,220 A | 7/1991 | Howland | 606/61 |
| 5,042,982 A | 8/1991 | Harms et al. | 606/61 |
| 5,047,029 A | 9/1991 | Aebi et al. | 606/61 |
| 5,067,955 A | 11/1991 | Cotrel | 606/61 |
| 5,074,864 A | 12/1991 | Cozad et al. | 606/54 |
| 5,084,049 A | 1/1992 | Asher et al. | 606/61 |
| 5,092,866 A | 3/1992 | Breard et al. | 606/61 |
| 5,102,412 A | 4/1992 | Rogozinski | 606/61 |
| 5,112,332 A | 5/1992 | Cozad et al. | 606/61 |
| 5,113,685 A | 5/1992 | Asher et al. | 72/458 |
| 5,116,334 A | 5/1992 | Cozad et al. | |
| 5,127,912 A | 7/1992 | Ray et al. | 606/61 |
| 5,129,388 A | 7/1992 | Vignaud et al. | 606/61 |
| 5,129,900 A | 7/1992 | Asher et al. | 606/61 |
| 5,147,359 A | 9/1992 | Cozad et al. | 606/61 |
| 5,154,718 A | 10/1992 | Cozad et al. | 606/61 |
| 5,176,680 A | 1/1993 | Vignaud et al. | 606/61 |
| 5,180,393 A | 1/1993 | Commarmond | 623/13 |
| 5,190,543 A | 3/1993 | Schläpfer | 606/61 |
| 5,201,734 A | 4/1993 | Cozad et al. | 606/62 |
| 5,207,678 A | 5/1993 | Harms et al. | 606/61 |
| 5,261,911 A | 11/1993 | Carl | 606/61 |
| 5,261,912 A | 11/1993 | Frigg | 606/61 |
| 5,261,913 A | 11/1993 | Marnay | 606/61 |
| 5,281,222 A | 1/1994 | Allard et al. | 606/54 |
| 5,282,801 A | 2/1994 | Sherman | 606/61 |
| 5,282,863 A | 2/1994 | Burton | 623/17 |
| 5,290,289 A | 3/1994 | Sanders et al. | 606/61 |
| 5,312,402 A | 5/1994 | Schläpfer et al. | 606/53 |
| 5,312,404 A | 5/1994 | Asher et al. | 606/61 |
| 5,344,422 A | 9/1994 | Frigg | 606/61 |
| 5,346,493 A | 9/1994 | Stahurski et al. | 606/61 |
| 5,360,429 A | 11/1994 | Jeanson et al. | 606/61 |
| 5,360,431 A | 11/1994 | Puno et al. | 606/72 |
| 5,374,267 A | 12/1994 | Siegal | |
| 5,380,325 A | 1/1995 | Lahille et al. | 606/61 |
| 5,380,326 A | 1/1995 | Lin | 606/61 |
| 5,382,248 A | 1/1995 | Jacobson et al. | 606/60 |
| 5,385,583 A | 1/1995 | Cotrel | 623/17 |
| 5,387,213 A | 2/1995 | Breard et al. | 606/61 |
| 5,415,661 A | 5/1995 | Holmes | 606/69 |
| 5,429,639 A | 7/1995 | Judet | 606/61 |
| 5,437,672 A | 8/1995 | Alleyne | |
| 5,443,467 A | 8/1995 | Biedermann et al. | 606/65 |
| 5,466,237 A | 11/1995 | Byrd, III et al. | 606/61 |
| 5,474,555 A | 12/1995 | Puno et al. | 606/73 |
| 5,480,442 A | 1/1996 | Bertanoli | |
| 5,487,742 A | 1/1996 | Cotrel | 606/61 |
| 5,496,321 A | 3/1996 | Puno et al. | 606/61 |
| 5,498,264 A | 3/1996 | Schlapfer et al. | 606/72 |
| 5,501,684 A | 3/1996 | Schlapfer et al. | |
| 5,520,689 A | 5/1996 | Schläpfer et al. | 606/61 |
| 5,534,001 A | 7/1996 | Schlapfer et al. | 606/61 |
| 5,536,268 A | 7/1996 | Griss | 606/61 |
| 5,540,688 A | 7/1996 | Navas | 606/61 |
| 5,545,167 A | 8/1996 | Lin | 606/61 |
| 5,549,607 A | 8/1996 | Olson et al. | 606/61 |
| 5,562,737 A | 10/1996 | Graf | 623/17 |
| 5,569,248 A | 10/1996 | Mathews | 606/61 |
| 5,591,166 A | 1/1997 | Bernhardt et al. | |
| 5,601,552 A | 2/1997 | Cotrel | |
| 5,609,592 A | 3/1997 | Brumfield et al. | 606/61 |
| 5,609,593 A | 3/1997 | Errico et al. | 606/61 |
| 5,611,800 A | 3/1997 | Davis et al. | 606/61 |
| 5,624,441 A | 4/1997 | Sherman et al. | 606/61 |
| 5,628,740 A | 5/1997 | Mullane | 606/61 |
| 5,630,816 A | 5/1997 | Kambin | 606/61 |
| 5,643,260 A | 7/1997 | Doherty | 606/61 |
| 5,645,599 A | 7/1997 | Samani | 623/17 |
| 5,651,789 A | 7/1997 | Cotrel | 606/61 |
| 5,653,708 A | 8/1997 | Howland | 606/61 |
| 5,658,284 A | 8/1997 | Sebastian et al. | 606/61 |
| 5,658,285 A | 8/1997 | Marnay et al. | |
| 5,667,506 A | 9/1997 | Sutterlin | 606/61 |
| 5,667,507 A | 9/1997 | Corin et al. | 606/61 |
| 5,669,910 A | 9/1997 | Korhonen et al. | 606/61 |
| 5,672,175 A | 9/1997 | Martin | 606/61 |
| 5,672,176 A | 9/1997 | Biedermann et al. | 606/61 |
| 5,676,665 A | 10/1997 | Bryan | 606/61 |
| 5,676,703 A | 10/1997 | Gelbard | 623/17 |
| 5,681,310 A | 10/1997 | Yuan et al. | |
| 5,681,311 A | 10/1997 | Foley et al. | 606/61 |
| 5,681,319 A | 10/1997 | Biedermann et al. | 606/104 |
| 5,683,391 A | 11/1997 | Boyd | 606/61 |
| 5,683,392 A | 11/1997 | Richelsoph et al. | 606/61 |
| 5,683,393 A | 11/1997 | Ralph | 606/61 |
| 5,688,272 A | 11/1997 | Montague et al. | 606/61 |
| 5,688,273 A | 11/1997 | Errico et al. | 606/61 |
| 5,690,629 A | 11/1997 | Asher et al. | 606/61 |
| 5,690,632 A | 11/1997 | Schwartz et al. | 606/73 |
| 5,690,633 A | 11/1997 | Taylor et al. | 606/73 |
| 5,693,053 A | 12/1997 | Estes | 606/61 |
| 5,697,929 A | 12/1997 | Mellinger | 606/61 |
| 5,700,292 A | 12/1997 | Margulies | 623/17 |
| 5,702,392 A | 12/1997 | Wu et al. | 606/61 |
| 5,702,394 A | 12/1997 | Henry et al. | 606/61 |
| 5,702,395 A | 12/1997 | Hopf | 606/61 |
| 5,702,396 A | 12/1997 | Hoenig et al. | 606/69 |
| 5,702,399 A | 12/1997 | Kilpela et al. | 606/72 |
| 5,702,452 A | 12/1997 | Argenson et al. | 623/17 |
| 5,713,900 A | 2/1998 | Benzel et al. | 606/61 |
| 5,713,904 A | 2/1998 | Errico et al. | 606/73 |
| 5,716,355 A | 2/1998 | Jackson et al. | 606/61 |
| 5,716,356 A | 2/1998 | Biedermann et al. | 606/61 |
| 5,716,357 A | 2/1998 | Rogozinski | 606/61 |
| 5,716,358 A | 2/1998 | Ochoa et al. | 606/62 |
| 5,716,359 A | 2/1998 | Ojima et al. | 606/76 |
| 5,720,751 A | 2/1998 | Jackson | 606/86 |
| 5,725,528 A | 3/1998 | Errico et al. | 606/61 |
| 5,725,582 A | 3/1998 | Bevan et al. | 623/17 |
| 5,728,098 A | 3/1998 | Sherman et al. | 606/61 |
| 5,733,286 A | 3/1998 | Errico et al. | 606/61 |
| 5,735,851 A | 4/1998 | Errico et al. | 606/61 |
| 5,741,254 A | 4/1998 | Henry et al. | 606/61 |
| 5,743,907 A | 4/1998 | Asher et al. | 606/61 |
| 5,743,911 A | 4/1998 | Cotrel | 606/61 |
| 5,752,957 A | 5/1998 | Ralph et al. | 606/61 |
| 5,766,254 A | 6/1998 | Gelbard | 623/17 |
| 5,776,135 A | 7/1998 | Errico et al. | |
| 5,782,833 A | 7/1998 | Haider | 606/61 |
| 5,785,711 A | 7/1998 | Errico et al. | 606/61 |
| 5,797,911 A | 8/1998 | Sherman et al. | 606/61 |
| 5,800,435 A | 9/1998 | Errico et al. | 606/61 |
| 5,810,819 A | 9/1998 | Errico et al. | 606/61 |
| 5,863,293 A | 1/1999 | Richelsoph | 606/61 |
| 5,868,745 A | 2/1999 | Alleyne | |
| 5,879,350 A | 3/1999 | Sherman et al. | 606/61 |

| Patent | Date | Inventor | Class |
|---|---|---|---|
| 5,885,286 A | 3/1999 | Sherman et al. | 606/61 |
| 5,891,145 A | 4/1999 | Morrison et al. | 606/61 |
| 5,899,904 A | 5/1999 | Errico et al. | 606/61 |
| RE36,221 E | 6/1999 | Breard et al. | 606/61 |
| 5,910,142 A | 6/1999 | Tatar | 606/61 |
| 5,925,047 A | 7/1999 | Errico et al. | 606/65 |
| 5,928,231 A | 7/1999 | Klein et al. | 606/60 |
| 5,928,232 A | 7/1999 | Howland et al. | 606/61 |
| 5,928,233 A | 7/1999 | Apfelbaum et al. | 606/61 |
| 5,947,965 A | 9/1999 | Bryan | 606/61 |
| 5,947,969 A | 9/1999 | Errico et al. | 606/61 |
| 5,954,725 A | 9/1999 | Sherman et al. | 606/78 |
| 5,961,517 A | 10/1999 | Biedermann et al. | 606/61 |
| 5,964,760 A | 10/1999 | Richelsoph | 606/61 |
| 5,980,521 A | 11/1999 | Montague et al. | 606/61 |
| 5,980,523 A | 11/1999 | Jackson | 606/61 |
| 5,984,922 A | 11/1999 | McKay | 606/61 |
| 5,989,251 A | 11/1999 | Nichols | 606/61 |
| 5,989,254 A | 11/1999 | Katz | 606/73 |
| 6,001,098 A | 12/1999 | Metz-Stavenhagen et al. | 606/61 |
| 6,004,322 A | 12/1999 | Bernstein | 606/61 |
| 6,010,503 A | 1/2000 | Richelsoph et al. | 606/61 |
| 6,015,409 A | 1/2000 | Jackson | 606/61 |
| 6,033,410 A | 3/2000 | McLean et al. | |
| 6,036,693 A | 3/2000 | Yuan et al. | 606/61 |
| 6,050,997 A | 4/2000 | Mullane | 606/61 |
| 6,053,917 A | 4/2000 | Sherman et al. | 606/61 |
| 6,063,089 A | 5/2000 | Errico et al. | 606/61 |
| 6,077,262 A | 6/2000 | Schläpfer et al. | 606/61 |
| 6,086,588 A | 7/2000 | Ameil et al. | 606/61 |
| 6,090,111 A | 7/2000 | Nichols | 606/61 |
| 6,096,039 A | 8/2000 | Stoltenberg et al. | 606/61 |
| 6,113,600 A | 9/2000 | Drummond et al. | 606/61 |
| 6,113,601 A | 9/2000 | Tatar | 606/61 |
| 6,123,706 A | 9/2000 | Lange | |
| 6,127,597 A | 10/2000 | Beyar et al. | 623/16 |
| 6,132,430 A | 10/2000 | Wagner | 606/61 |
| 6,132,434 A | 10/2000 | Sherman et al. | 606/78 |
| 6,132,464 A | 10/2000 | Martin | |
| 6,136,000 A | 10/2000 | Louis et al. | 606/61 |
| 6,146,383 A | 11/2000 | Studer et al. | 606/61 |
| 6,171,311 B1 | 1/2001 | Richelsoph | 606/61 |
| 6,193,720 B1 | 2/2001 | Yuan et al. | 606/61 |
| 6,197,028 B1 | 3/2001 | Ray et al. | 606/61 |
| 6,210,413 B1 | 4/2001 | Justis et al. | 606/61 |
| 6,217,578 B1 | 4/2001 | Crozet et al. | 606/61 |
| 6,248,106 B1 | 6/2001 | Ferree | 606/61 |
| 6,254,602 B1 | 7/2001 | Justis | 606/61 |
| 6,261,287 B1 | 7/2001 | Metz-Stavenhagen | 606/61 |
| 6,267,765 B1 | 7/2001 | Taylor et al. | |
| 6,273,888 B1 | 8/2001 | Justis | 606/61 |
| 6,273,914 B1 | 8/2001 | Papas | 623/17.11 |
| 6,280,442 B1 | 8/2001 | Barker et al. | |
| 6,280,443 B1 | 8/2001 | Gu et al. | 606/61 |
| 6,287,311 B1 | 9/2001 | Sherman et al. | 606/78 |
| 6,293,949 B1 | 9/2001 | Justis et al. | 606/61 |
| 6,302,882 B1 | 10/2001 | Lin et al. | |
| 6,302,888 B1 | 10/2001 | Mellinger et al. | 606/73 |
| 6,309,391 B1 | 10/2001 | Crandall et al. | 606/61 |
| 6,325,802 B1 | 12/2001 | Frigg | 606/61 |
| 6,328,740 B1 | 12/2001 | Richelsoph | 606/61 |
| 6,344,057 B1 | 2/2002 | Rabbe et al. | 623/17 |
| 6,355,040 B1 | 3/2002 | Richelsoph et al. | 606/61 |
| 6,379,354 B1 | 4/2002 | Rogozinski | 606/61 |
| 6,402,749 B1 | 6/2002 | Ashman | 606/61 |
| 6,402,751 B1 | 6/2002 | Hoeck et al. | 606/61 |
| 6,402,752 B2 | 6/2002 | Schäffler-Wachter et al. | 606/61 |
| 6,413,257 B1 | 7/2002 | Lin et al. | 606/61 |
| 6,416,515 B1 | 7/2002 | Wagner | 606/61 |
| 6,423,064 B1 | 7/2002 | Kluger | 606/61 |
| 6,440,169 B1 | 8/2002 | Elberg et al. | 623/17.16 |
| 6,451,021 B1 | 9/2002 | Ralph et al. | 606/61 |
| 6,454,773 B1 | 9/2002 | Sherman et al. | 606/78 |
| 6,458,131 B1 | 10/2002 | Ray | 606/61 |
| 6,458,132 B2 | 10/2002 | Choi | 606/61 |
| 6,468,276 B1 | 10/2002 | McKay | 606/61 |
| 6,471,705 B1 | 10/2002 | Biedermann et al. | 606/61 |
| 6,475,219 B1 | 11/2002 | Shelokov | |
| 6,478,797 B1 | 11/2002 | Paul | 606/61 |
| 6,482,207 B1 | 11/2002 | Errico | 606/61 |
| 6,485,491 B1 | 11/2002 | Farris et al. | 606/61 |
| 6,488,681 B2 | 12/2002 | Martin et al. | 606/61 |
| 6,520,962 B1 | 2/2003 | Taylor et al. | 606/61 |
| 6,520,990 B1 | 2/2003 | Ray | 623/17.11 |
| 6,537,276 B2 | 3/2003 | Metz-Stavenhagen | 606/61 |
| 6,540,748 B2 | 4/2003 | Lombardo | 606/61 |
| 6,540,749 B2 | 4/2003 | Schäfer et al. | 606/61 |
| 6,547,789 B1 | 4/2003 | Ventre et al. | 606/61 |
| 6,554,831 B1 | 4/2003 | Rivard et al. | |
| 6,554,832 B2 | 4/2003 | Shluzas | 606/61 |
| 6,554,834 B1 | 4/2003 | Crozet et al. | 606/65 |
| 6,565,565 B1 | 5/2003 | Yuan et al. | 606/61 |
| 6,565,566 B1 | 5/2003 | Wagner et al. | 606/61 |
| 6,565,567 B1 | 5/2003 | Haider | 606/61 |
| 6,565,605 B2 | 5/2003 | Goble et al. | 623/17.11 |
| 6,572,617 B1 | 6/2003 | Senegas | 606/61 |
| 6,572,653 B1 | 6/2003 | Simonson | 623/17.13 |
| 6,579,290 B1 | 6/2003 | Hardcastle et al. | 606/61 |
| 6,585,737 B1 | 7/2003 | Baccelli et al. | 606/61 |
| 6,589,243 B1 | 7/2003 | Viart et al. | |
| 6,616,669 B2 | 9/2003 | Ogilvie et al. | 606/61 |
| 6,623,485 B2 | 9/2003 | Doubler et al. | 606/61 |
| 6,626,905 B1 | 9/2003 | Schmiel et al. | 606/61 |
| 6,626,908 B2 | 9/2003 | Cooper et al. | 606/61 |
| 6,645,207 B2 | 11/2003 | Dixon et al. | 606/61 |
| 6,652,526 B1 | 11/2003 | Arafiles | 606/61 |
| 6,656,181 B2 | 12/2003 | Dixon et al. | 606/69 |
| 6,660,004 B2 | 12/2003 | Barker et al. | 606/61 |
| 6,660,005 B2 | 12/2003 | Toyama et al. | 606/61 |
| 6,676,661 B1 | 1/2004 | Martin Benlloch et al. | |
| 6,695,845 B2 | 2/2004 | Dixon et al. | 606/70 |
| 6,706,045 B2 | 3/2004 | Lin et al. | 606/61 |
| 6,709,434 B1 | 3/2004 | Gournay et al. | 606/61 |
| 6,716,213 B2 | 4/2004 | Shitoto | 606/61 |
| 6,716,214 B1 | 4/2004 | Jackson | 606/61 |
| 6,726,689 B2 | 4/2004 | Jackson | 606/73 |
| 6,736,820 B2 | 5/2004 | Biedermann et al. | 606/73 |
| 6,740,086 B2 | 5/2004 | Richelsoph | |
| 6,749,614 B2 | 6/2004 | Teitelbaum et al. | 606/61 |
| 6,752,807 B2 | 6/2004 | Lin et al. | 606/61 |
| 6,755,829 B1 | 6/2004 | Bono et al. | 606/61 |
| 6,755,835 B2 | 6/2004 | Schultheiss et al. | 606/73 |
| 6,761,719 B2 | 7/2004 | Justis et al. | 606/61 |
| 6,783,526 B1 | 8/2004 | Lin et al. | 606/61 |
| 6,783,527 B2 | 8/2004 | Drewry et al. | 606/61 |
| 6,786,907 B2 | 9/2004 | Lange | 606/61 |
| 6,793,656 B1 | 9/2004 | Mathews | 606/61 |
| 6,805,695 B2 | 10/2004 | Keith et al. | 606/61 |
| 6,805,714 B2 | 10/2004 | Sutcliffe | 623/17.11 |
| 6,811,567 B2 | 11/2004 | Reiley | 623/17.11 |
| 6,827,743 B2 | 12/2004 | Eisermann et al. | |
| 6,832,999 B2 | 12/2004 | Ueyama et al. | 606/61 |
| 6,840,940 B2 | 1/2005 | Ralph et al. | 606/61 |
| 6,843,791 B2 | 1/2005 | Serhan | 606/61 |
| 6,852,128 B2 | 2/2005 | Lange | 623/17.11 |
| 6,858,029 B2 | 2/2005 | Yeh | |
| 6,858,030 B2 | 2/2005 | Martin et al. | 606/61 |
| 6,869,433 B2 | 3/2005 | Glascott | 606/73 |
| 6,875,211 B2 | 4/2005 | Nichols et al. | 606/61 |
| 6,881,215 B2 | 4/2005 | Assaker et al. | 606/61 |
| 6,883,520 B2 | 4/2005 | Lambrecht | 128/898 |
| 6,887,242 B2 | 5/2005 | Doubler et al. | 606/61 |
| 6,899,714 B2 | 5/2005 | Vaughan | 606/61 |
| 6,918,911 B2 | 7/2005 | Biedermann et al. | 606/61 |
| 6,932,817 B2 | 8/2005 | Baynham et al. | 606/61 |
| 6,945,974 B2 | 9/2005 | Dalton | 606/70 |
| 6,951,561 B2 | 10/2005 | Warren et al. | 606/73 |
| 6,964,666 B2 | 11/2005 | Jackson | 606/61 |
| 6,966,910 B2 | 11/2005 | Ritland | 606/61 |
| 6,986,771 B2 | 1/2006 | Paul et al. | 606/61 |
| 6,991,632 B2 | 1/2006 | Ritland | 606/61 |
| 7,008,423 B2 | 3/2006 | Assaker et al. | 606/61 |
| 7,011,685 B2 | 3/2006 | Arnin et al. | 623/17.16 |
| 7,018,378 B2 | 3/2006 | Biedermann et al. | 606/61 |
| 7,018,379 B2 | 3/2006 | Drewry | 606/61 |
| 7,022,122 B2 | 4/2006 | Amrein et al. | 606/61 |
| 7,029,475 B2 | 4/2006 | Panjabi | 606/61 |
| 7,033,392 B2 | 4/2006 | Schmiel | |

| Patent No. | Date | Inventor(s) | Class |
|---|---|---|---|
| 7,048,736 B2 | 5/2006 | Robinson et al. | 606/61 |
| 7,051,451 B2 | 5/2006 | Augostino et al. | 33/512 |
| 7,060,066 B2 | 6/2006 | Zhao et al. | 606/61 |
| 7,074,237 B2 | 7/2006 | Goble et al. | 623/17.11 |
| 7,081,117 B2 | 7/2006 | Bono et al. | 606/61 |
| 7,083,621 B2 | 8/2006 | Shaolian et al. | 606/61 |
| 7,083,622 B2 | 8/2006 | Simonson | 606/61 |
| 7,087,056 B2 | 8/2006 | Vaughan | 606/61 |
| 7,087,057 B2 | 8/2006 | Konieczynski et al. | 606/73 |
| 7,087,084 B2 | 8/2006 | Reiley | 623/17.11 |
| 7,090,698 B2 | 8/2006 | Goble et al. | 623/17.11 |
| 7,101,398 B2 | 9/2006 | Dooris et al. | 623/13.11 |
| 7,104,991 B2 | 9/2006 | Dixon | |
| 7,104,992 B2 | 9/2006 | Bailey | 606/61 |
| 7,107,091 B2 | 9/2006 | Jutras et al. | 600/429 |
| 7,125,410 B2 | 10/2006 | Freudiger | 606/61 |
| 7,125,426 B2 | 10/2006 | Moumene et al. | 623/23.42 |
| 7,137,985 B2 | 11/2006 | Jahng | |
| 7,163,538 B2 * | 1/2007 | Altarac et al. | 606/86 A |
| 7,189,235 B2 | 3/2007 | Cauthen | |
| 7,214,227 B2 | 5/2007 | Colleran et al. | 606/61 |
| 7,250,052 B2 | 7/2007 | Landry et al. | 606/61 |
| 7,270,665 B2 | 9/2007 | Morrison et al. | |
| 7,282,064 B2 | 10/2007 | Chin | 623/17.15 |
| 7,294,128 B2 | 11/2007 | Alleyne et al. | |
| 7,294,129 B2 | 11/2007 | Hawkins et al. | 606/61 |
| 7,306,603 B2 | 12/2007 | Boehm, Jr. et al. | 606/61 |
| 7,306,606 B2 | 12/2007 | Sasing | 606/61 |
| 7,309,355 B2 | 12/2007 | Donnelly et al. | |
| 7,326,210 B2 | 2/2008 | Jahng et al. | 606/61 |
| 7,335,201 B2 | 2/2008 | Doubler et al. | 606/61 |
| 7,338,490 B2 | 3/2008 | Ogilvie et al. | |
| 7,338,491 B2 | 3/2008 | Baker et al. | |
| 7,344,539 B2 | 3/2008 | Serhan et al. | |
| 7,361,196 B2 | 4/2008 | Fallin et al. | |
| 7,377,923 B2 | 5/2008 | Purcell et al. | |
| 7,445,627 B2 | 11/2008 | Hawkes et al. | |
| 7,455,684 B2 | 11/2008 | Gradel et al. | |
| 7,476,238 B2 | 1/2009 | Panjabi | |
| 7,479,156 B2 | 1/2009 | Lourdel et al. | |
| 7,481,828 B2 | 1/2009 | Mazda et al. | |
| 7,491,218 B2 | 2/2009 | Landry et al. | |
| 7,503,924 B2 | 3/2009 | Lee et al. | |
| 7,513,905 B2 | 4/2009 | Jackson | |
| 7,513,911 B2 | 4/2009 | Lambrecht et al. | |
| 7,520,879 B2 | 4/2009 | Justis | |
| 7,530,992 B2 | 5/2009 | Biedermann et al. | |
| 7,533,672 B2 | 5/2009 | Morgan et al. | |
| 7,553,320 B2 | 6/2009 | Molz, IV et al. | |
| 7,553,329 B2 | 6/2009 | Lambrecht et al. | |
| 7,559,943 B2 | 7/2009 | Mujwid | |
| 7,563,274 B2 | 7/2009 | Justis et al. | |
| 7,572,279 B2 | 8/2009 | Jackson | |
| 7,578,833 B2 | 8/2009 | Bray | |
| 7,585,312 B2 | 9/2009 | Rawlins et al. | |
| 7,588,575 B2 | 9/2009 | Colleran et al. | |
| 7,588,588 B2 | 9/2009 | Spitler et al. | |
| 7,594,924 B2 | 9/2009 | Albert et al. | |
| 7,597,707 B2 | 10/2009 | Freudiger | |
| 7,601,166 B2 | 10/2009 | Biedermann et al. | |
| 7,608,095 B2 | 10/2009 | Yuan et al. | |
| 7,611,526 B2 | 11/2009 | Carl et al. | |
| 7,615,068 B2 | 11/2009 | Timm et al. | |
| 7,625,394 B2 | 12/2009 | Molz, IV et al. | |
| 7,625,396 B2 | 12/2009 | Jackson | |
| 7,635,379 B2 | 12/2009 | Callahan et al. | |
| 7,648,520 B2 | 1/2010 | Markworth | |
| 7,648,522 B2 | 1/2010 | David | |
| 7,662,172 B2 | 2/2010 | Warnick | |
| 7,662,173 B2 | 2/2010 | Cragg et al. | |
| 7,662,175 B2 | 2/2010 | Jackson | |
| 7,674,293 B2 | 3/2010 | Kuiper et al. | |
| 7,678,136 B2 | 3/2010 | Doubler et al. | |
| 7,678,137 B2 | 3/2010 | Butler et al. | |
| 7,682,377 B2 | 3/2010 | Konieczynski et al. | |
| 7,691,129 B2 | 4/2010 | Felix | |
| 7,691,132 B2 | 4/2010 | Landry et al. | |
| 7,699,873 B2 | 4/2010 | Stevenson et al. | |
| 7,699,875 B2 | 4/2010 | Timm et al. | |
| 7,704,270 B2 | 4/2010 | De Coninck | |
| 7,708,762 B2 | 5/2010 | McCarthy et al. | |
| 7,713,287 B2 | 5/2010 | Timm et al. | |
| 7,713,288 B2 | 5/2010 | Timm et al. | |
| 7,717,939 B2 | 5/2010 | Ludwig et al. | |
| 7,722,646 B2 | 5/2010 | Ralph et al. | |
| 7,722,649 B2 | 5/2010 | Biedermann et al. | |
| 7,722,654 B2 | 5/2010 | Taylor et al. | |
| 7,727,259 B2 | 6/2010 | Park | |
| 7,727,261 B2 | 6/2010 | Barker et al. | |
| 7,731,734 B2 | 6/2010 | Clement et al. | |
| 7,731,736 B2 | 6/2010 | Guenther et al. | |
| 7,763,051 B2 | 7/2010 | Labrom et al. | |
| 7,763,052 B2 | 7/2010 | Jahng | |
| 7,766,944 B2 | 8/2010 | Metz-Stavenhagen | |
| 7,766,945 B2 | 8/2010 | Nilsson et al. | |
| 7,776,071 B2 | 8/2010 | Fortin et al. | |
| 7,785,350 B2 | 8/2010 | Eckhardt et al. | |
| 7,785,354 B2 | 8/2010 | Biedermann et al. | |
| 7,789,896 B2 | 9/2010 | Jackson | |
| 7,794,477 B2 | 9/2010 | Melkent et al. | |
| 7,794,481 B2 | 9/2010 | Molz, IV et al. | |
| 7,799,060 B2 | 9/2010 | Lange et al. | |
| 7,803,189 B2 | 9/2010 | Koske | |
| 7,806,913 B2 | 10/2010 | Fanger et al. | |
| 7,806,914 B2 | 10/2010 | Boyd et al. | |
| 7,811,288 B2 | 10/2010 | Jones et al. | |
| 7,811,309 B2 | 10/2010 | Timm et al. | |
| 7,811,311 B2 | 10/2010 | Markworth et al. | |
| 7,815,664 B2 | 10/2010 | Sherman et al. | |
| 7,815,665 B2 | 10/2010 | Jahng et al. | |
| 7,819,899 B2 | 10/2010 | Lancial | |
| 7,819,901 B2 | 10/2010 | Yuan et al. | |
| 7,819,902 B2 | 10/2010 | Abdelgany et al. | |
| 7,828,824 B2 | 11/2010 | Kwak et al. | |
| 7,828,825 B2 | 11/2010 | Bruneau et al. | |
| 7,828,826 B2 | 11/2010 | Drewry et al. | |
| 7,828,830 B2 | 11/2010 | Thramann et al. | |
| 7,833,250 B2 | 11/2010 | Jackson | |
| 7,833,256 B2 | 11/2010 | Biedermann et al. | |
| 7,842,072 B2 | 11/2010 | Dawson | |
| 7,850,715 B2 | 12/2010 | Banouskou et al. | |
| 7,850,718 B2 | 12/2010 | Bette et al. | |
| 7,854,752 B2 | 12/2010 | Colleran et al. | |
| 7,857,833 B2 | 12/2010 | Abdou | |
| 7,857,834 B2 | 12/2010 | Boschert | |
| 7,862,586 B2 | 1/2011 | Malek | |
| 7,862,587 B2 | 1/2011 | Jackson | |
| 7,862,588 B2 | 1/2011 | Abdou | |
| 7,862,591 B2 | 1/2011 | Dewey et al. | |
| 7,862,594 B2 | 1/2011 | Abdelgany et al. | |
| 7,871,413 B2 | 1/2011 | Park et al. | |
| 7,875,059 B2 | 1/2011 | Patterson et al. | |
| 7,875,060 B2 | 1/2011 | Chin | |
| 7,879,074 B2 | 2/2011 | Kwak et al. | |
| 7,892,266 B2 | 2/2011 | Carli | |
| 7,909,856 B2 | 3/2011 | Yuan et al. | |
| 7,914,558 B2 | 3/2011 | Landry et al. | |
| 7,918,792 B2 | 4/2011 | Drzyzga et al. | |
| 7,927,359 B2 | 4/2011 | Trautwein | |
| 2003/0004511 A1 | 1/2003 | Ferree | |
| 2003/0171749 A1 | 9/2003 | Le Couedic et al. | |
| 2004/0015166 A1 | 1/2004 | Gorek | |
| 2004/0034374 A1 | 2/2004 | Zatzsch et al. | |
| 2004/0049285 A1 | 3/2004 | Haas | |
| 2004/0097925 A1 | 5/2004 | Boehm, Jr. et al. | |
| 2004/0111088 A1 | 6/2004 | Picetti et al. | |
| 2004/0122425 A1 | 6/2004 | Suzuki et al. | |
| 2004/0147928 A1 | 7/2004 | Landry et al. | |
| 2004/0153077 A1 | 8/2004 | Biedermann et al. | |
| 2004/0158247 A1 | 8/2004 | Sitiso et al. | |
| 2004/0162560 A1 | 8/2004 | Raynor et al. | |
| 2004/0172022 A1 | 9/2004 | Landry et al. | |
| 2004/0172024 A1 | 9/2004 | Gorek | |
| 2004/0215192 A1 | 10/2004 | Justis et al. | |
| 2004/0225289 A1 | 11/2004 | Biedermann et al. | |
| 2004/0230192 A1 | 11/2004 | Graf | |
| 2004/0230304 A1 | 11/2004 | Yuan et al. | |
| 2005/0049589 A1 | 3/2005 | Jackson | |

| | | | | | | |
|---|---|---|---|---|---|---|
| 2005/0080415 A1 | 4/2005 | Keyer et al. | | 2007/0016194 A1 | 1/2007 | Shaolian et al. |
| 2005/0090822 A1 | 4/2005 | DiPoto | | 2007/0016201 A1 | 1/2007 | Freudiger |
| 2005/0096652 A1 | 5/2005 | Burton | | 2007/0049936 A1 | 3/2007 | Colleran et al. |
| 2005/0107788 A1 | 5/2005 | Beaurain et al. | | 2007/0083200 A1 | 4/2007 | Gittings et al. |
| 2005/0113923 A1 | 5/2005 | Acker et al. | | 2007/0088359 A1 | 4/2007 | Woods et al. |
| 2005/0131404 A1 | 6/2005 | Mazda et al. | | 2007/0093814 A1 | 4/2007 | Callahan, II et al. |
| 2005/0131406 A1 | 6/2005 | Reiley et al. | | 2007/0093820 A1 | 4/2007 | Freudiger |
| 2005/0143737 A1 | 6/2005 | Pafford et al. | | 2007/0093821 A1 | 4/2007 | Freudiger |
| 2005/0171537 A1 | 8/2005 | Mazel et al. | | 2007/0118122 A1 | 5/2007 | Butler et al. |
| 2005/0171543 A1 | 8/2005 | Timm et al. | | 2007/0123871 A1 | 5/2007 | Jahng |
| 2005/0177156 A1 | 8/2005 | Timm et al. | | 2007/0161994 A1 | 7/2007 | Lowery et al. |
| 2005/0177157 A1 | 8/2005 | Jahng | | 2007/0162007 A1 | 7/2007 | Shoham |
| 2005/0177164 A1 | 8/2005 | Walters et al. | | 2007/0167946 A1 | 7/2007 | Triplett et al. |
| 2005/0182400 A1 | 8/2005 | White | | 2007/0167947 A1 | 7/2007 | Gittings |
| 2005/0182401 A1 | 8/2005 | Timm et al. | | 2007/0198014 A1 | 8/2007 | Graf et al. |
| 2005/0192569 A1 | 9/2005 | Nichols et al. | | 2007/0213719 A1 | 9/2007 | Hudgins et al. |
| 2005/0228382 A1 | 10/2005 | Richelsoph et al. | | 2007/0233068 A1 | 10/2007 | Bruneau et al. |
| 2005/0228385 A1 | 10/2005 | Iott et al. | | 2007/0233072 A1 | 10/2007 | Dickinson et al. |
| 2005/0240180 A1 | 10/2005 | Vienney et al. | | 2007/0233090 A1 | 10/2007 | Naifeh et al. |
| 2005/0240265 A1 | 10/2005 | Kuiper et al. | | 2007/0233091 A1 | 10/2007 | Naifeh et al. |
| 2005/0261770 A1 | 11/2005 | Kuiper et al. | | 2007/0233092 A1 | 10/2007 | Falahee |
| 2005/0267470 A1 | 12/2005 | McBride | | 2007/0233093 A1 | 10/2007 | Falahee |
| 2005/0277922 A1 | 12/2005 | Trieu et al. | | 2007/0233094 A1 | 10/2007 | Colleran et al. |
| 2005/0288670 A1 | 12/2005 | Panjabi et al. | | 2007/0250061 A1 | 10/2007 | Chin et al. |
| 2006/0025771 A1 | 2/2006 | Jackson | | 2007/0270836 A1 | 11/2007 | Bruneau et al. |
| 2006/0036324 A1 | 2/2006 | Sachs et al. | | 2007/0270838 A1 | 11/2007 | Bruneau et al. |
| 2006/0052783 A1 | 3/2006 | Dant et al. | | 2007/0276380 A1 | 11/2007 | Jahng et al. |
| 2006/0052784 A1 | 3/2006 | Dant et al. | | 2007/0288009 A1 | 12/2007 | Brown et al. |
| 2006/0052786 A1 | 3/2006 | Dant et al. | | 2007/0288012 A1 | 12/2007 | Colleran et al. |
| 2006/0058787 A1 | 3/2006 | David | | 2008/0009864 A1 | 1/2008 | Forton et al. |
| 2006/0058788 A1 | 3/2006 | Hammer et al. | | 2008/0021459 A1 | 1/2008 | Lim |
| 2006/0079894 A1 | 4/2006 | Colleran et al. | | 2008/0021461 A1 | 1/2008 | Barker et al. |
| 2006/0079896 A1 | 4/2006 | Kwak et al. | | 2008/0033433 A1 | 2/2008 | Implicito |
| 2006/0084978 A1 | 4/2006 | Mokhtar | | 2008/0039838 A1 | 2/2008 | Landry et al. |
| 2006/0084982 A1 | 4/2006 | Kim | | 2008/0051787 A1 | 2/2008 | Remington et al. |
| 2006/0084983 A1 | 4/2006 | Kim | | 2008/0065073 A1 | 3/2008 | Perriello et al. |
| 2006/0084984 A1 | 4/2006 | Kim | | 2008/0065075 A1 | 3/2008 | Dant et al. |
| 2006/0084985 A1 | 4/2006 | Kim | | 2008/0065079 A1 | 3/2008 | Bruneau et al. |
| 2006/0084987 A1 | 4/2006 | Kim | | 2008/0071273 A1 | 3/2008 | Hawkes et al. |
| 2006/0084988 A1 | 4/2006 | Kim | | 2008/0077139 A1 | 3/2008 | Landry et al. |
| 2006/0084989 A1 | 4/2006 | Dickinson et al. | | 2008/0183215 A1 | 7/2008 | Altarac et al. |
| 2006/0084990 A1 | 4/2006 | Gournay et al. | | 2008/0195208 A1 | 8/2008 | Castellvi et al. |
| 2006/0085069 A1 | 4/2006 | Kim | | 2008/0262554 A1 | 10/2008 | Klyce et al. |
| 2006/0085070 A1 | 4/2006 | Kim | | 2008/0312693 A1 | 12/2008 | Trautwein et al. |
| 2006/0089643 A1 | 4/2006 | Mujwid | | 2010/0030275 A1* | 2/2010 | Winslow et al. ............ 606/264 |
| 2006/0095035 A1 | 5/2006 | Jones et al. | | 2010/0174317 A1 | 7/2010 | Timm et al. |
| 2006/0106383 A1 | 5/2006 | Biedermann et al. | | 2010/0198270 A1 | 8/2010 | Barker et al. |
| 2006/0111712 A1 | 5/2006 | Jackson | | 2010/0222819 A1 | 9/2010 | Timm et al. |
| 2006/0122620 A1 | 6/2006 | Kim | | | | |
| 2006/0129148 A1 | 6/2006 | Simmons et al. | | FOREIGN PATENT DOCUMENTS | | |
| 2006/0129149 A1 | 6/2006 | Iott et al. | | EP | 0128058 B1 | 4/1988 |
| 2006/0142761 A1 | 6/2006 | Landry et al. | | EP | 0669109 B1 | 8/1995 |
| 2006/0149242 A1 | 7/2006 | Kraus et al. | | EP | 0982007 | 3/2000 |
| 2006/0149244 A1 | 7/2006 | Amrein et al. | | EP | 1281362 A2 | 2/2003 |
| 2006/0149380 A1 | 7/2006 | Lotz et al. | | EP | 1330987 A1 | 7/2003 |
| 2006/0161153 A1 | 7/2006 | Hawkes et al. | | FR | 2612070 A1 | 9/1988 |
| 2006/0195093 A1 | 8/2006 | Jahng | | FR | 2615095 A1 | 11/1988 |
| 2006/0200128 A1 | 9/2006 | Mueller | | FR | 2844180 A1 | 3/2004 |
| 2006/0200131 A1 | 9/2006 | Chao et al. | | FR | 2880256 B1 | 7/2006 |
| 2006/0229607 A1 | 10/2006 | Brumfield | | GB | 780652 | 8/1957 |
| 2006/0229613 A1 | 10/2006 | Timm et al. | | GB | 2173104 | 10/1986 |
| 2006/0235385 A1 | 10/2006 | Whipple | | GB | 2382304 | 5/2003 |
| 2006/0235389 A1 | 10/2006 | Albert et al. | | KR | 20080072848 | 8/2008 |
| 2006/0235392 A1 | 10/2006 | Hammer et al. | | WO | WO 87/07134 | 12/1987 |
| 2006/0235393 A1 | 10/2006 | Bono et al. | | WO | WO 94/21185 | 9/1994 |
| 2006/0241600 A1 | 10/2006 | Ensign et al. | | WO | WO 98/27884 | 7/1998 |
| 2006/0241601 A1 | 10/2006 | Trautwein et al. | | WO | WO 01/45576 | 6/2001 |
| 2006/0241603 A1 | 10/2006 | Jackson | | WO | WO 01/91656 | 12/2001 |
| 2006/0241757 A1 | 10/2006 | Anderson | | WO | WO 02/07621 | 1/2002 |
| 2006/0247623 A1 | 11/2006 | Anderson et al. | | WO | WO 02/07622 | 1/2002 |
| 2006/0247631 A1 | 11/2006 | Ahn et al. | | WO | WO 02/17803 | 3/2002 |
| 2006/0247637 A1 | 11/2006 | Colleran et al. | | WO | WO 02/39921 | 5/2002 |
| 2006/0253118 A1 | 11/2006 | Bailey | | WO | WO 02/43603 | 6/2002 |
| 2006/0264935 A1 | 11/2006 | White | | WO | WO 02/102259 | 12/2002 |
| 2006/0264937 A1 | 11/2006 | White | | WO | WO 03/007828 | 1/2003 |
| 2006/0276897 A1 | 12/2006 | Winslow et al. | | WO | WO 03/009737 | 2/2003 |
| 2006/0282073 A1 | 12/2006 | Simanovsky | | WO | WO 03/015647 | 2/2003 |
| 2006/0282078 A1 | 12/2006 | Labrom et al. | | WO | WO 03/037216 | 5/2003 |
| 2007/0016190 A1 | 1/2007 | Martinez et al. | | WO | WO 03/077806 | 9/2003 |

| WO | WO2004/024011 | 3/2004 |
| WO | WO2004/034916 | 4/2004 |
| WO | WO2006/033503 | 3/2006 |
| WO | WO2006/066685 | 6/2006 |
| WO | WO2006/105935 | 10/2006 |
| WO | WO2007064324 | 6/2007 |
| WO | WO2007/080317 | 7/2007 |
| WO | WO2008/034130 | 3/2008 |
| WO | WO2008/073544 | 6/2008 |

OTHER PUBLICATIONS

Mekanika, Inc. Website, 2003; Mekanika—The Spinal Stabilization Company, product description for Modulus System, 2 pages, <http://mekanika.com/htm/modsystem.htm>.

Zimmer, Inc. Website, 2007; Zimmer Spine, product description for Dynesis—The Dynamic Stabilization System, 5 pages, <http://www.zimmer com/ctl?template=INn&action=1&op=global&id=9165&pr=Y>.

Ito Medical Instrument website, 2006; ITOIKA Medical Instruments, product description for S-Plate, 15 pages, <http://ito-ika.co.jp/s-plate/splate1.pdf and http://ito-ika.co.jp/s-plate/splate1.pdf>.

"Flexible rods and the case for dynamic stabilization," Jason M. Highsmith, M.D., et al., Neurosurg. Focus, vol. 22, Jan. 2007, pp. 1-5.

"The Spinous Process: The Forgotten Appendage," Kenneth R. Kattan, M. D. eta l., Skeletal Radiology, vol. 6, 1981, pp. 199-204.

"Morphological and functional changes of the lumbar spinous processes in the elderly," R. Scapinelli, Surgical Radiologic Anatomy, vol. 11, 1989, pp. 129-133.

"The Paraspinal Sacrospinalis-Splitting Approach to the Lumbar Spine," Leon L. Wiltse et al., The Journal of Bone & Joint Surgery, vol. 50-A, No. 5, Jul. 1968 pp. 919-926.

Dynamic Reconstruction of the Spine, D.H. Kim et al., Thieme, New York 2006, Chapters 1, 2, 30, 31, 37-43.

International Search Report for PCT/US07/70981 dated Apr. 23, 2008, 7 pages.

International Search Report for PCT/US/2009/058466 dated Apr. 29, 2010, 13 pages.

International Search Report for PCT/US/2009/058460 dated Apr. 29, 2010, 11 pages.

International Search Report for PCT/US/2009/058470 dated Apr. 29, 2010, 12 pages.

International Search Report for PCT/US/2009/066567 dated Jul. 20, 2010, 9 pages.

* cited by examiner

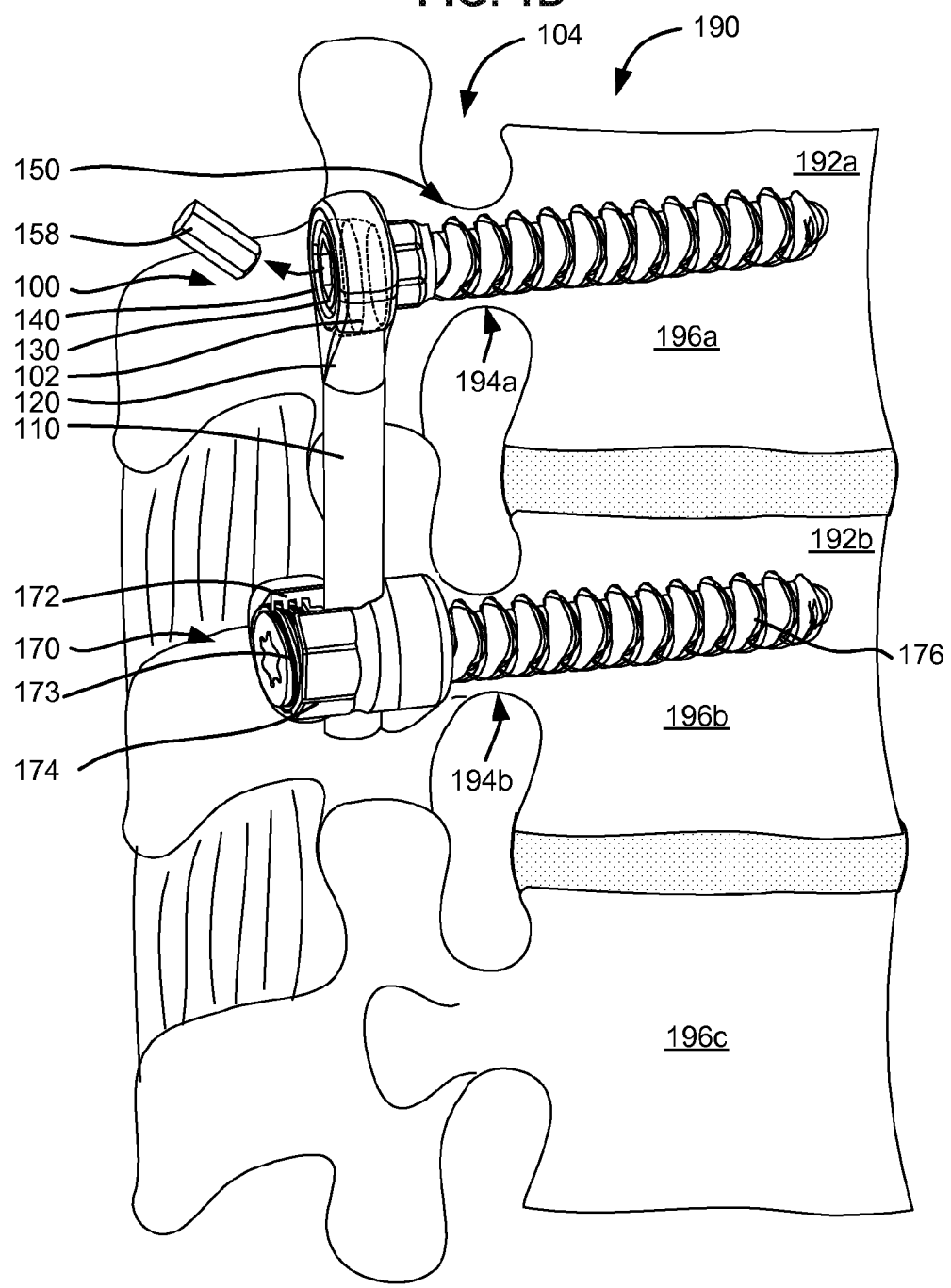

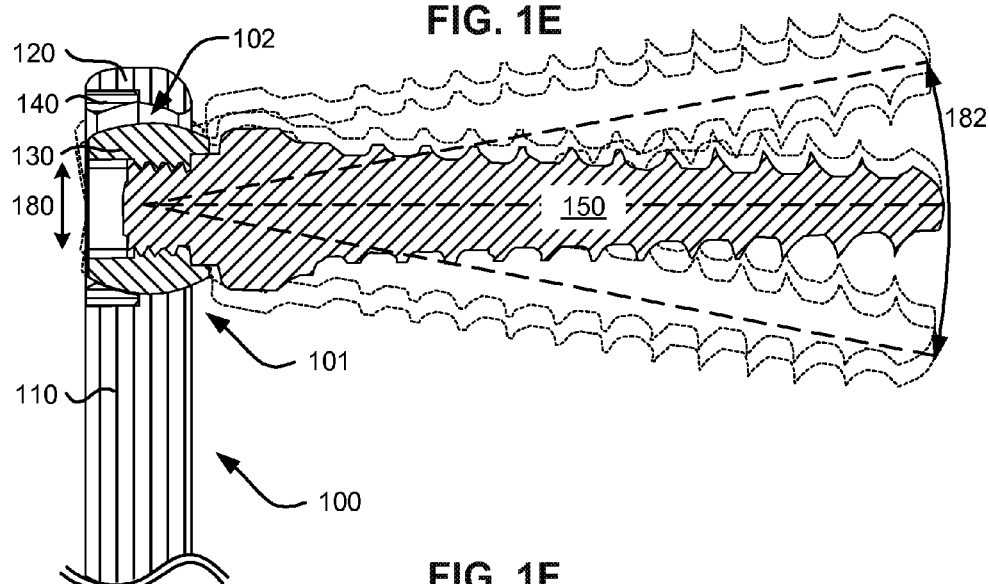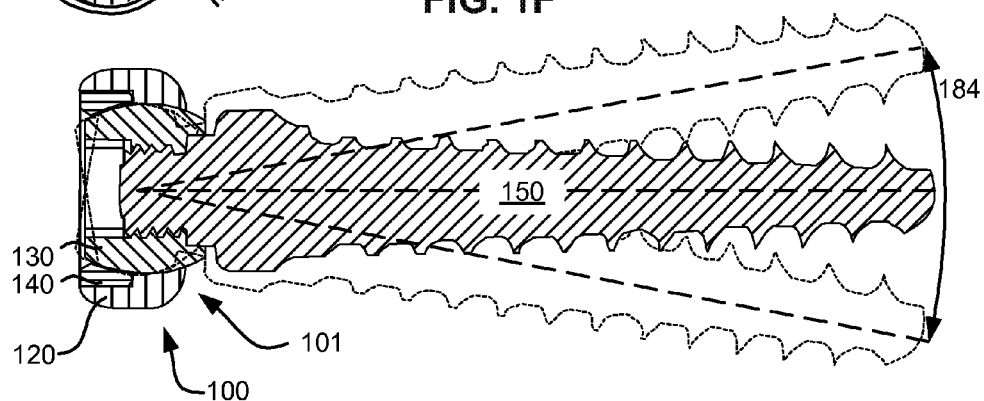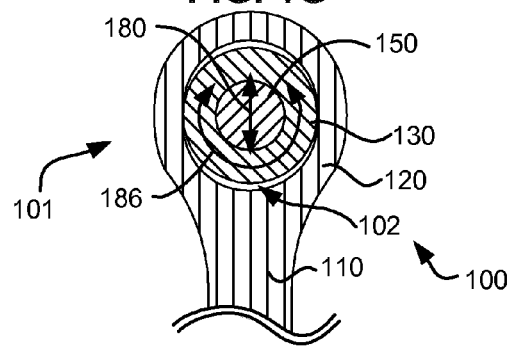

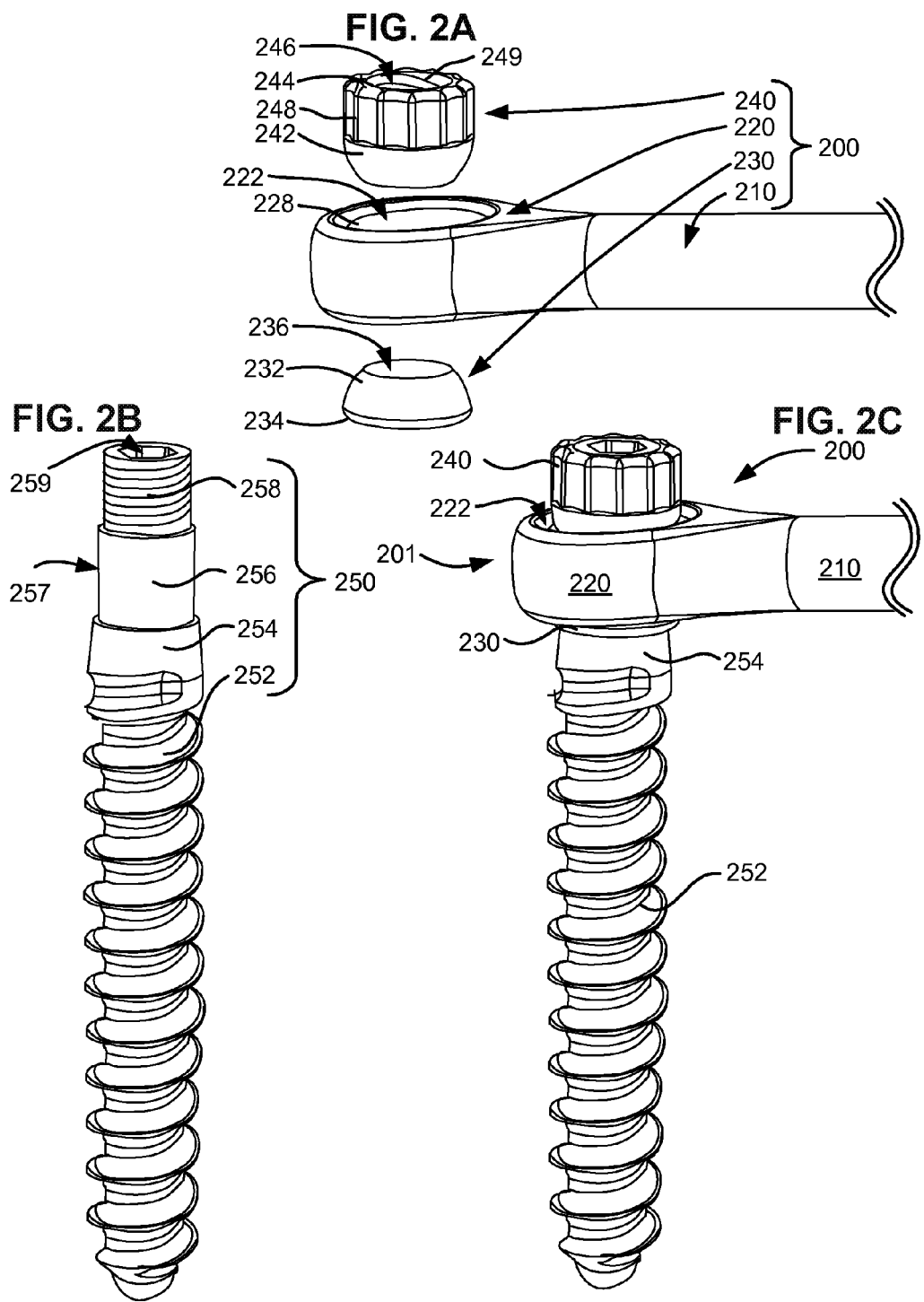

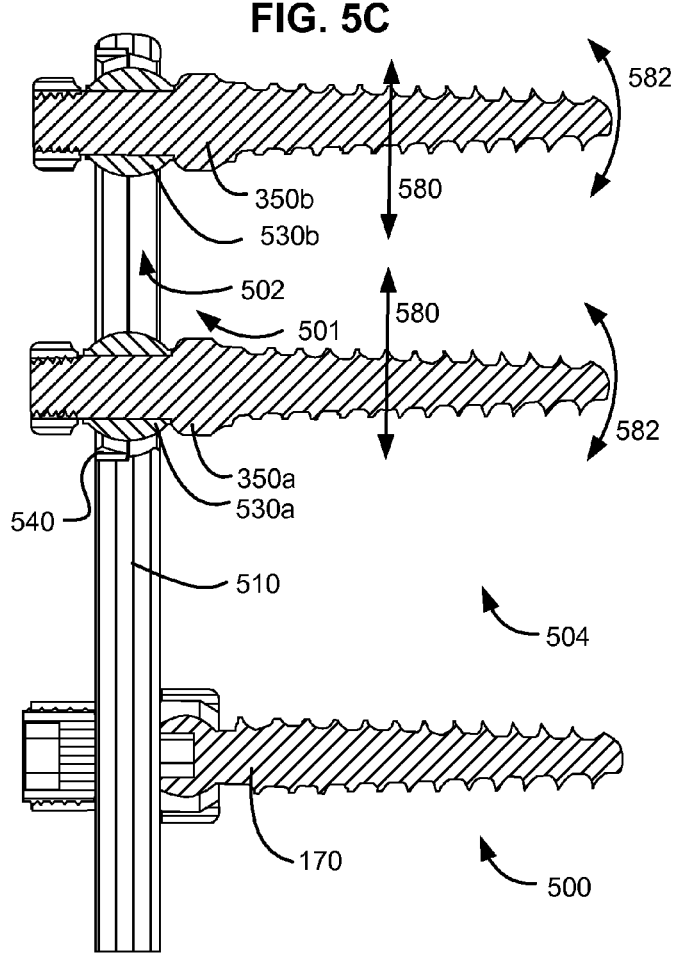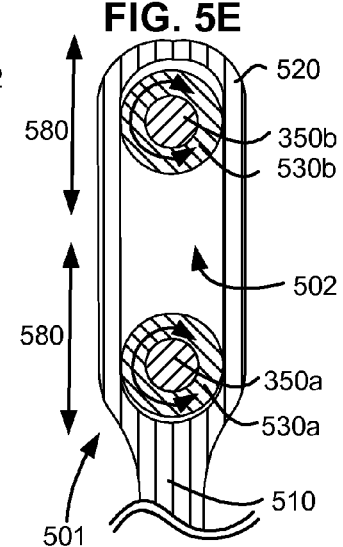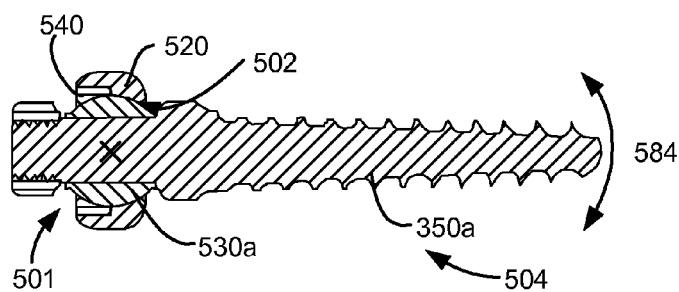

FIG. 6A
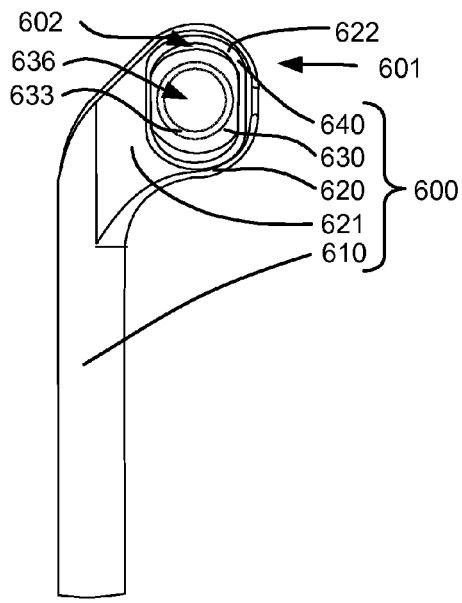
FIG. 6B
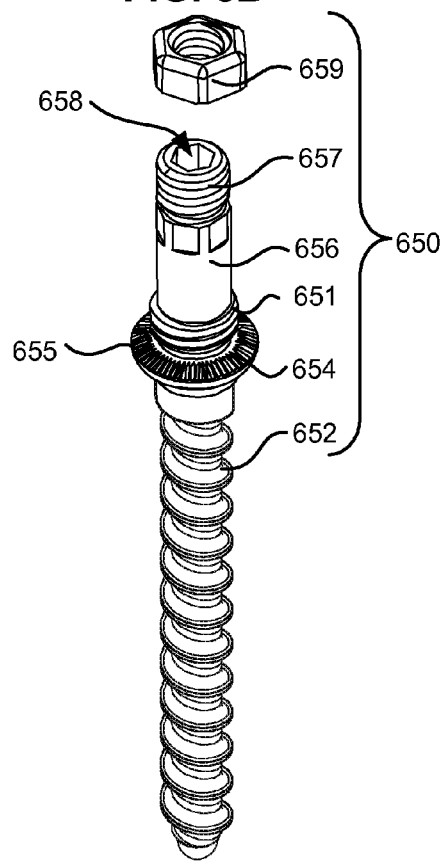
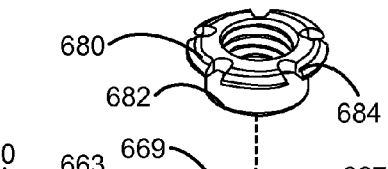
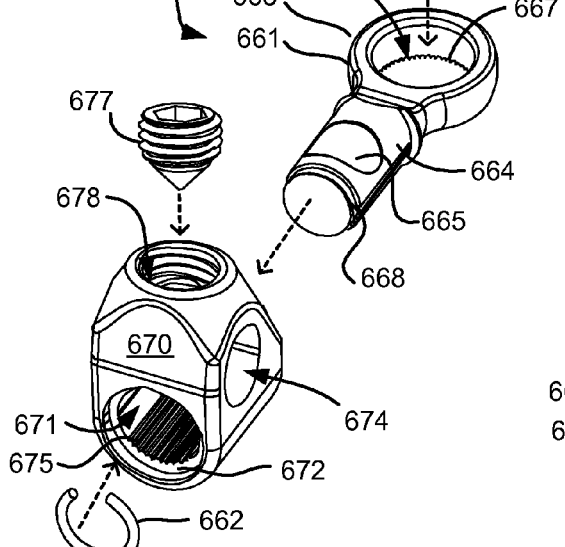
FIG. 6C
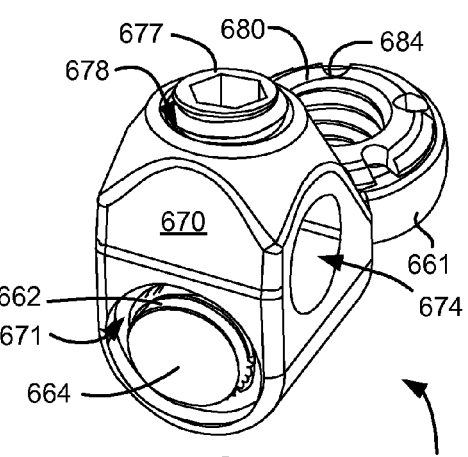
FIG. 6D

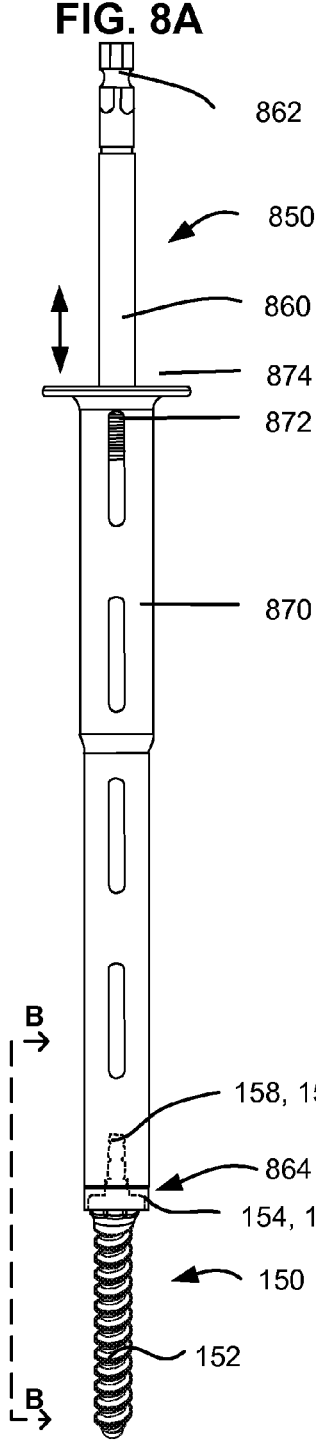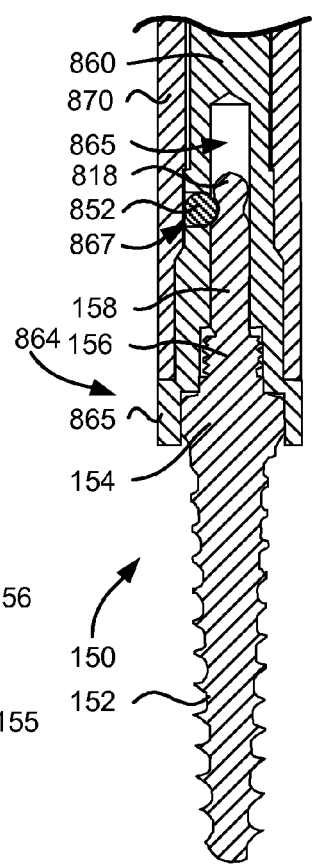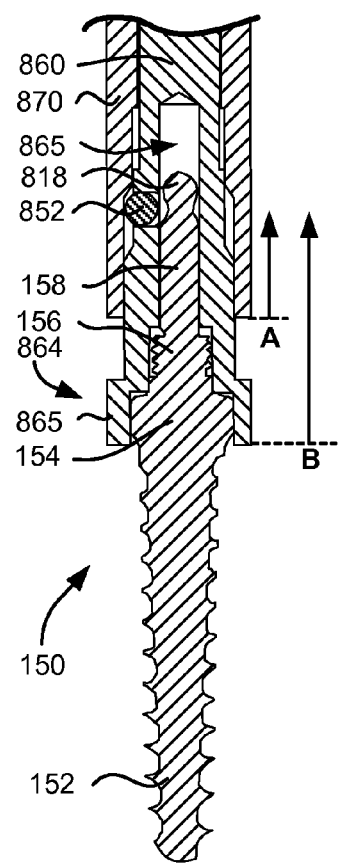

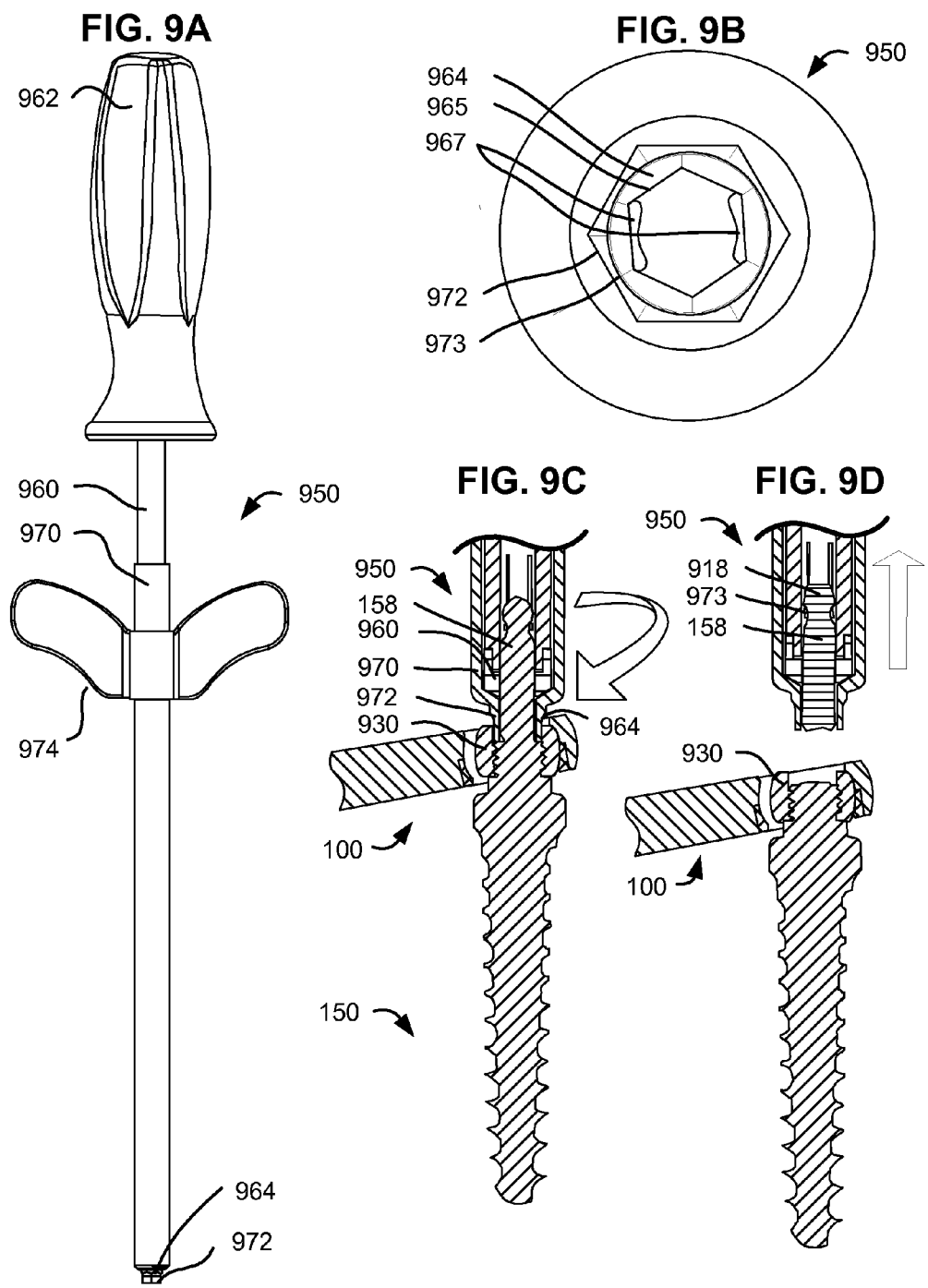

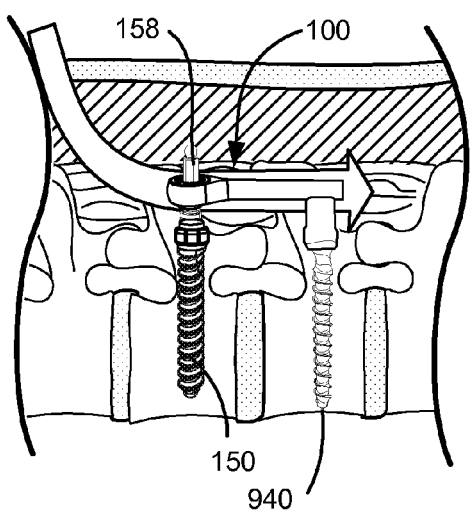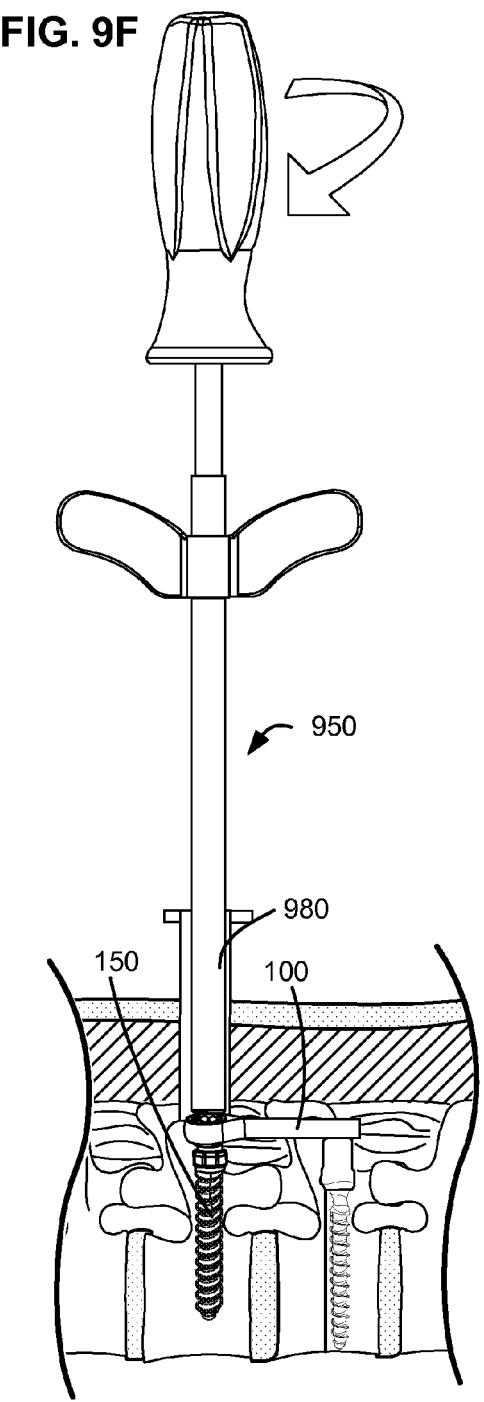

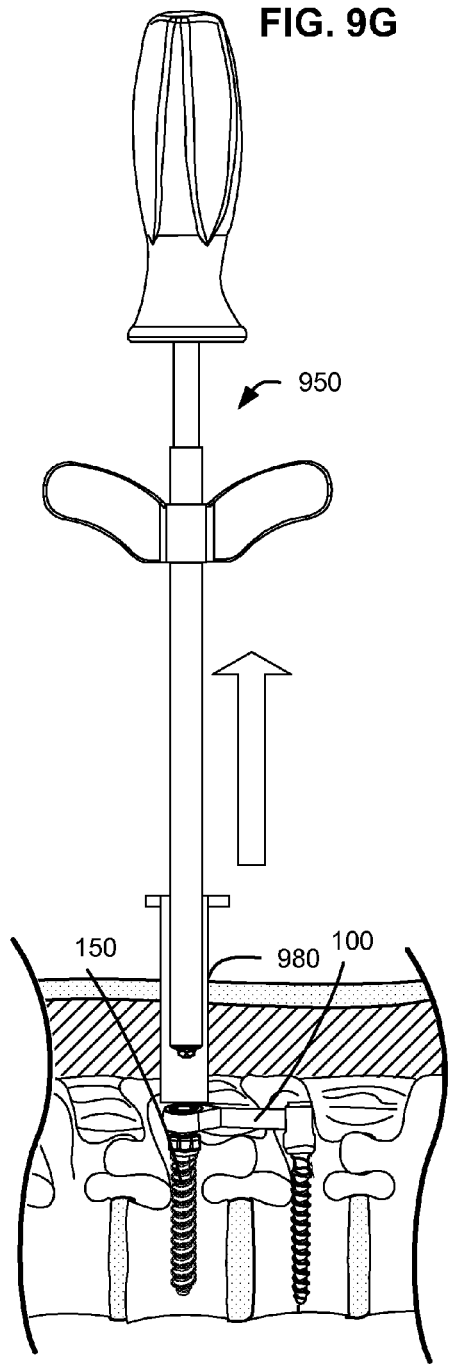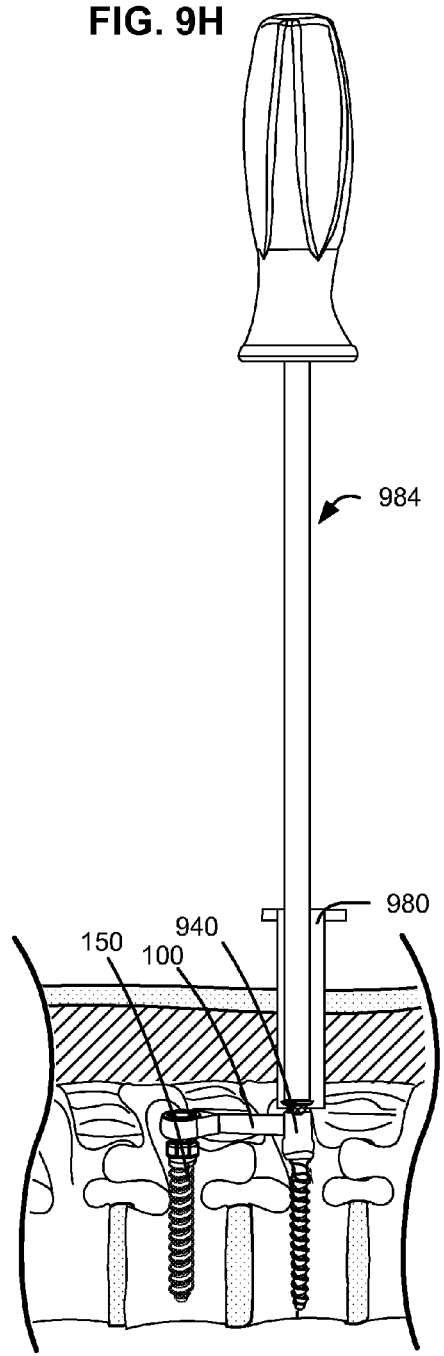

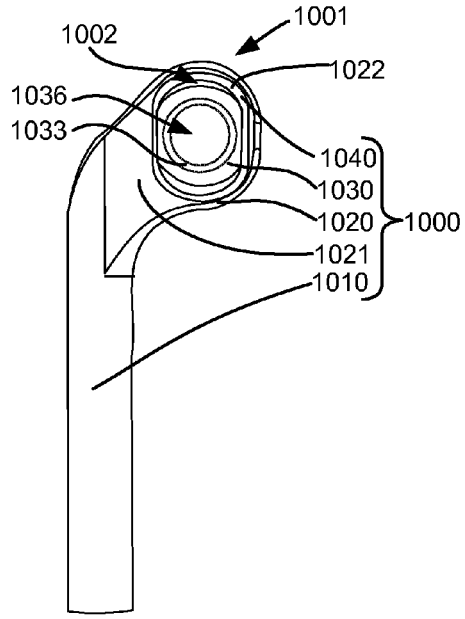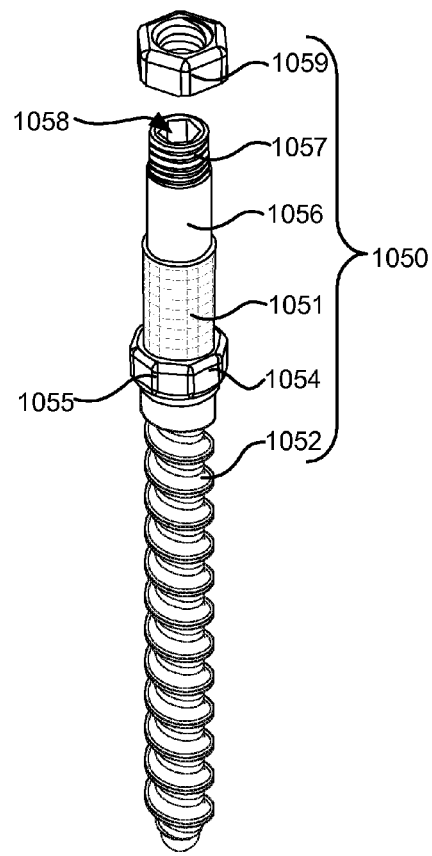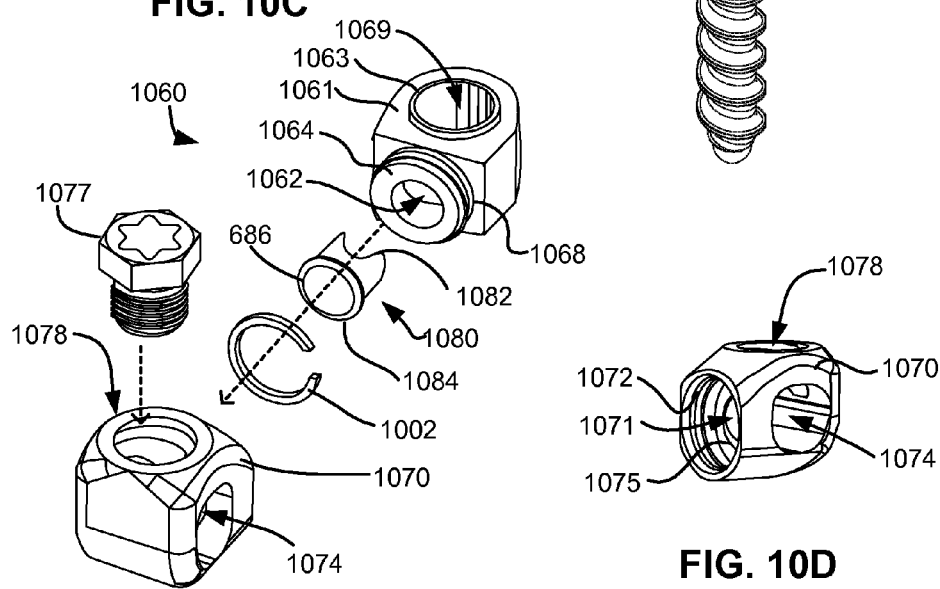

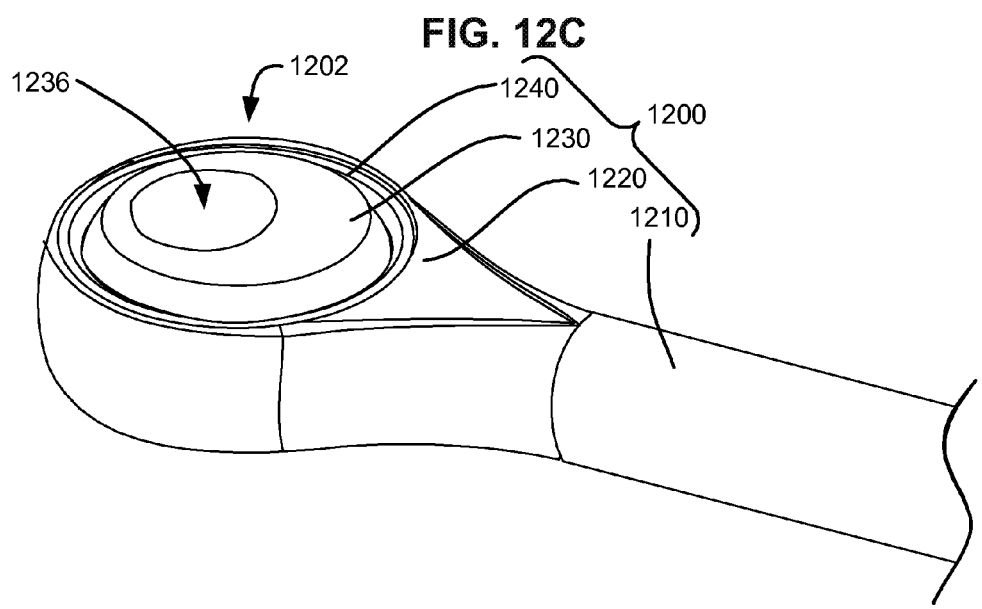

ADAPTIVE SPINAL ROD AND METHODS FOR STABILIZATION OF THE SPINE

CLAIM TO PRIORITY

This patent application claims priority to the following patents and patent applications:
U.S. Provisional Patent Application No. 61/353,508, filed Jun. 10, 2010, entitled "ADAPTIVE SPINAL ROD AND METHODS FOR STABILIZATION OF THE SPINE"; and
U.S. Provisional Patent Application No. 61/435,961, filed Jan. 25, 2011, entitled "ADAPTIVE SPINAL ROD AND METHODS FOR STABILIZATION OF THE SPINE".

All of the afore-mentioned patent applications are incorporated herein by reference in their entireties.

CROSS-REFERENCES TO RELATED APPLICATIONS

This application is related to all of the afore-mentioned patent applications. This application is also related to all of the following applications including:
U.S. patent application Ser. No. 13/014,878, filed Jan. 27, 2011, entitled "ADAPTIVE SPINAL ROD AND METHODS FOR STABILIZATION OF THE SPINE"; and
U.S. patent application Ser. No. 13/014,894, filed Jan. 27, 2011, entitled "ADAPTIVE SPINAL ROD AND METHODS FOR STABILIZATION OF THE SPINE".

All of the afore-mentioned patent applications are incorporated herein by reference in their entireties.

BACKGROUND OF INVENTION

Back pain is a significant clinical problem and the costs to treat it, both surgical and medical, are estimated to be over $2 billion per year. One method for treating a broad range of degenerative spinal disorders is spinal fusion. Implantable medical devices designed to fuse vertebrae of the spine to treat have developed rapidly over the last decade. However, spinal fusion has several disadvantages including reduced range of motion and accelerated degenerative changes adjacent the fused vertebrae.

Alternative devices and treatments have been developed for treating degenerative spinal disorders while preserving motion. These devices and treatments offer the possibility of treating degenerative spinal disorders without the disadvantages of spinal fusion. However, current devices and treatments suffer from disadvantages e.g., complicated implantation procedures; lack of flexibility to conform to diverse patient anatomy; the need to remove tissue and bone for implantation; increased stress on spinal anatomy; insecure anchor systems; poor durability, and poor revision options. Consequently, there is a need for new and improved devices and methods for treating degenerative spinal disorders while preserving motion.

SUMMARY OF INVENTION

The present invention includes a spinal implant system and methods that can dynamically stabilize the spine while providing for the preservation of spinal motion. Embodiments of the invention provide an adaptive spinal stabilization system which includes: versatile components, adaptive stabilization assemblies, and methods of implantation. An aspect of embodiments of the invention is the ability to stabilize two, three and/or more levels of the spine by the selection of appropriate components of embodiments of the invention for implantation in a patient. Another aspect of embodiments of the invention is the ability to accommodate particular anatomy of the patient by providing a system of versatile components which may be customized to the anatomy and needs of a particular patient and procedure. Another aspect of the invention is to facilitate the process of implantation and minimize disruption of tissues during implantation.

Thus, the present invention provides new and improved systems, devices and methods for treating degenerative spinal disorders by providing and implanting an adaptive spinal stabilization assembly which supports the spine while preserving motion. These and other objects, features and advantages of the invention will be apparent from the drawings and detailed description which follow.

BRIEF DESCRIPTION OF THE DRAWINGS

FIG. 1D is a perspective view of a spinal prosthesis including the adaptive spinal rod of FIGS. 1A, and 1B and bone anchor of FIG. 1C according to an embodiment of the present invention.

FIG. 1E is a saggital section of the spinal prosthesis of FIG. 1D.

FIG. 1F is a transverse section of the spinal prosthesis of FIG. 1D.

FIG. 1G is a dorsal section of the spinal prosthesis of FIG. 1D.

FIG. 2A is an exploded view of an adaptive spinal rod according to an embodiment of the present invention.

FIG. 2B is a perspective view of a bone anchor suitable for use with the adaptive spinal rod of FIG. 2A according to an embodiment of the present invention.

FIG. 2C is a perspective view of an assembly including the bone anchor of FIG. 2B and the adaptive spinal rod of FIG. 2A according to an embodiment of the present invention.

FIG. 5C is a saggital section of a two-level adaptive spinal prosthesis incorporating the adaptive spinal rod of FIG. 5B.

FIG. 5D is a transverse section of a two-level adaptive spinal prosthesis incorporating the adaptive spinal rod of FIG. 5B.

FIG. 5E is a dorsal section of a two-level adaptive spinal prosthesis incorporating the adaptive spinal rod of FIG. 5B.

FIG. 6A is a view of an adaptive spinal rod according to an alternative embodiment of the present invention.

FIG. 6B is a view of a bone anchor for use in a two-level adaptive stabilization system according to an alternative embodiment of the present invention.

FIG. 6C is an exploded view of a polyaxial connector for use in a two-level adaptive stabilization system according to an alternative embodiment of the present invention.

FIG. 6D is an alternative view of a component of the connector of FIG. 6C.

FIG. 8A shows a perspective view of an implantation tool for an adaptive bone anchor according to an embodiment of the invention.

FIGS. 8B and 8C show detailed sectional views of the head of the implantation tool of FIG. 8A in relation to the bone anchor.

FIG. 9A shows a perspective view of an attachment tool for securing an adaptive spinal rod to a bone anchor according to an embodiment of the invention.

FIG. 9B shows a detailed view of the head of the attachment tool of FIG. 9A.

FIGS. 9C and 9D show detailed sectional views of the head of the attachment tool of FIG. 9A in relation to an adaptive spinal rod and bone anchor.

FIG. 9E-9H are lateral views of the lumbar spine illustrating steps to secure an adaptive spinal rod to a bone anchor using the attachment tool of FIG. 9A according to an embodiment of the invention.

FIG. 10A is a view of an adaptive spinal rod according to an alternative embodiment of the present invention.

FIG. 10B is a view of a bone anchor for use in a two-level adaptive stabilization system according to an alternative embodiment of the present invention.

FIG. 10C is an exploded view of a polyaxial connector for use in a two-level adaptive stabilization system according to an alternative embodiment of the present invention.

FIG. 10D is an alternative view of a component of the connector of FIG. 10C.

FIG. 12C is a perspective view of the adaptive spinal rod of FIG. 11A as assembled.

Figure 1A:
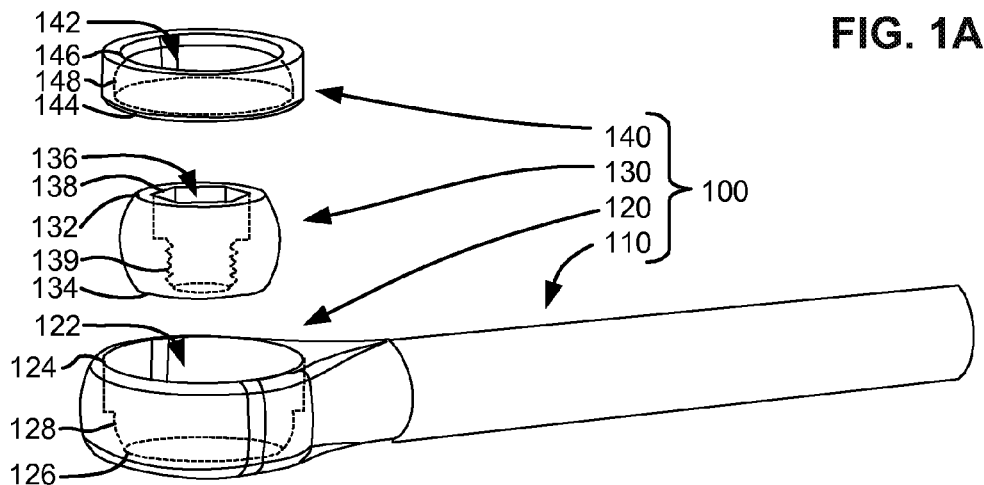
FIG. 1A is an exploded view of an adaptive spinal rod according to an embodiment of the present invention.

In the figures and detail description that follows common reference numerals are used to indicate like elements throughout the drawings and detailed description; therefore, reference numerals used in a drawing may or may not be referenced in the detailed description specific to such drawing if the associated element is referenced and described elsewhere. Elements having identical reference numbers differing only by a terminal reference letter are related and/or identical—the description of the structure and/or function of each such element should be considered with respect to all such elements to the extent differences between the elements are not specified. The first digit in a three digit reference numeral indicates the series of figures in which the referenced item first appears. Likewise the first two digits in a four digit reference numeral.

The terms "vertical" and "horizontal" are used throughout the detailed description to describe general orientation of structures relative to the spine of a human patient that is standing. This application also uses the terms proximal and distal in the conventional manner when describing the components of the spinal implant system. Thus, proximal refers to the end or side of a device or component closest to the hand operating the device, whereas distal refers to the end or side of a device furthest from the hand operating the device. For example, the tip of a bone screw that enters a bone would conventionally be called the distal end (it is furthest from the surgeon) while the head of the screw would be termed the proximal end (it is closest to the surgeon).

DETAILED DESCRIPTION OF THE PREFERRED EMBODIMENTS

The present invention includes a versatile spinal implant system and methods which can stabilize the spine while providing for the preservation of spinal motion. Alternative embodiments can be used for spinal fusion. An aspect of the invention is stabilizing the spine while restoring and/or preserving the natural motion of the spine including the quality of motion as well as the range of motion. Still, another aspect of the invention is providing for load sharing and stabilization of the spine while preserving motion. Another aspect of embodiments of the invention is the ability to stabilize two, three and/or more levels of the spine by the selection of appropriate components for implantation in a patient. Another aspect of the invention is the ability to provide for higher stiffness and fusion at one level or to one portion of the spine while allowing for lower stiffness and adaptive stabilization at another adjacent level or to another portion of the spine. Embodiments of the invention allow for fused levels to be placed next to dynamically stabilized levels. Such embodiments of the invention enable vertebral levels adjacent to fusion levels to be shielded by providing a transition from a rigid fusion level to a dynamically stable, motion preserved, and more mobile level. Alternative embodiments can be utilized in spinal fusion procedures.

Embodiments of the present invention provide for assembly of an adaptive spinal prosthesis which supports the spine while providing for the preservation of spinal motion. Another aspect of the invention is to provide an adaptable modular system which can be utilized to create an adaptive spinal prosthesis customized to the needs of the patient. The adaptive stabilization system includes bone anchors and adaptive spinal rods. The bone anchors secure the adaptive spinal stabilization system to the spinal anatomy. The adaptive spinal rods provide adaptive stabilization by contributing for load sharing and stabilization of the spine while preserving motion. Embodiments of the invention include surgical kits, surgical methods, constructs, and prostheses including: an adaptive spinal rod; a bone screw specifically designed for use with an adaptive spinal rod; a bone anchor in combination with an adaptive spinal rod; a plurality of bone anchors in combination with an adaptive spinal rod; a plurality of bone anchors in combinations with a plurality of adaptive spinal rods.

Adaptive Stabilization System

Figure 1B:
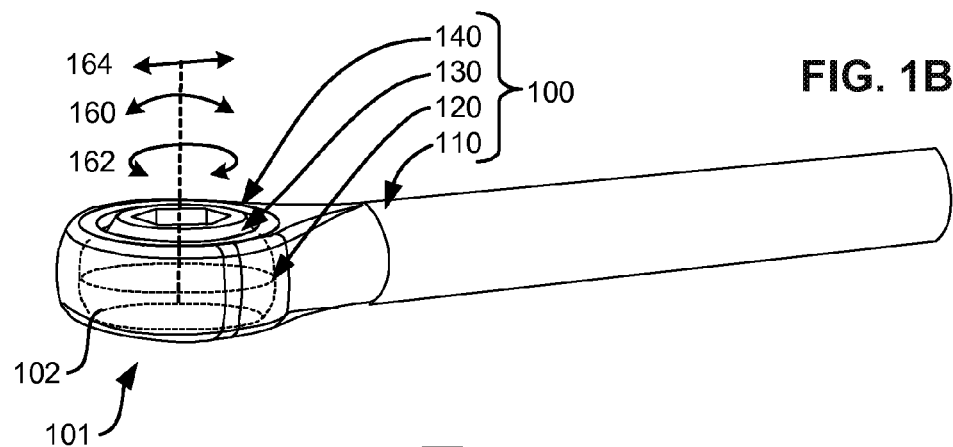
FIG. 1B is a perspective view of an assembled adaptive spinal rod according to an embodiment of the present invention.
Figure 1C:
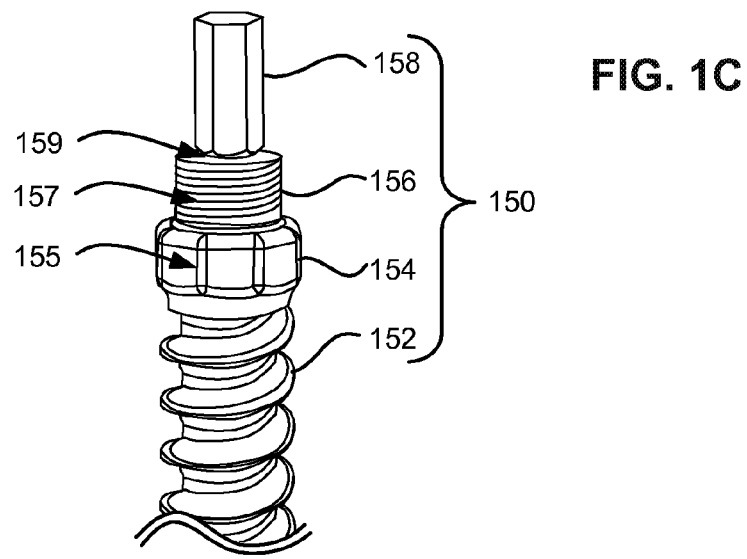
FIG. 1C is a perspective view of a bone anchor for adapted for use with the adaptive spinal rod of FIGS. 1A, and 1B according to an embodiment of the present invention.
Figure 1H:
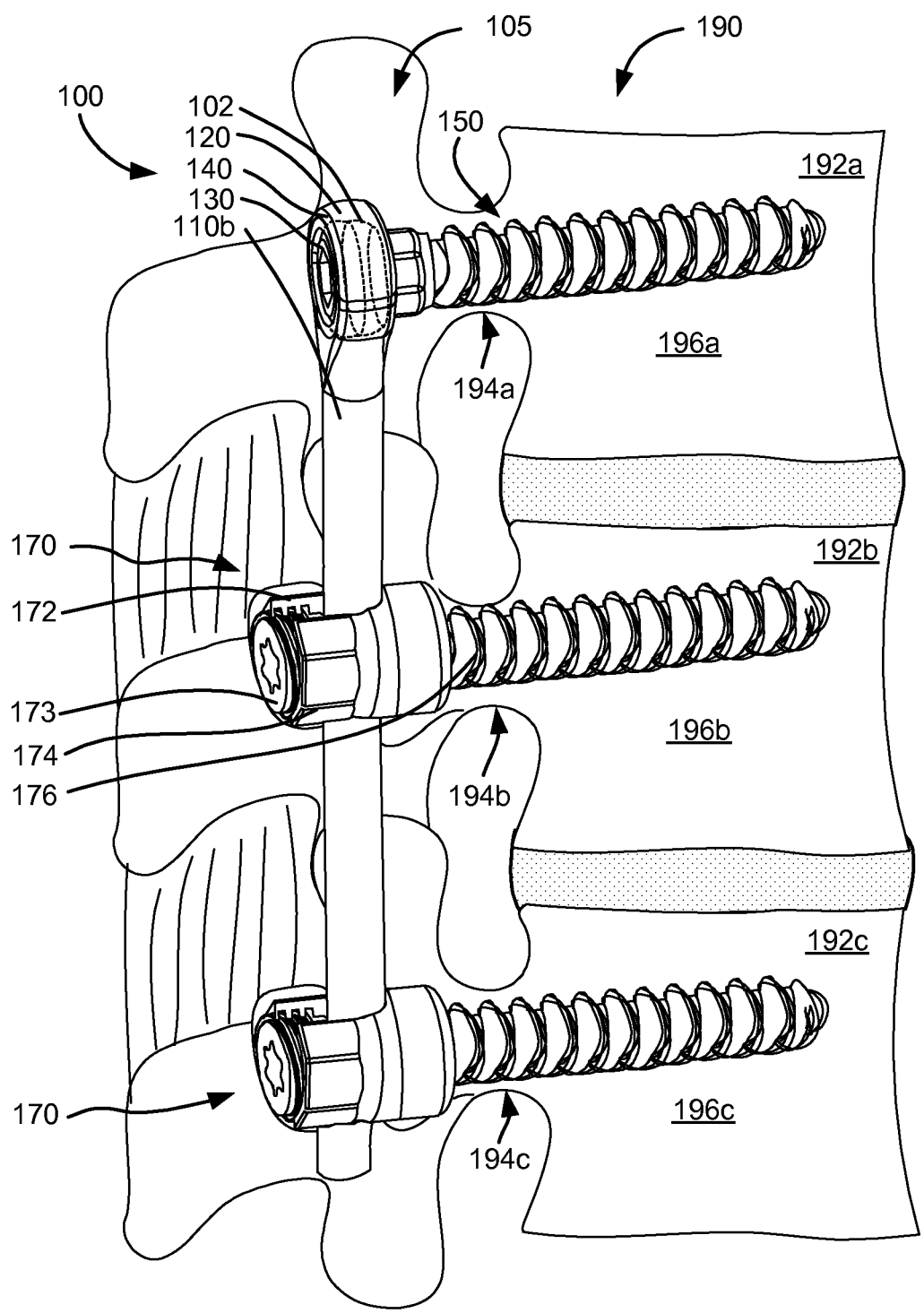
FIG. 1H is a perspective view of a two-level spinal prosthesis including the adaptive spinal rod of FIGS. 1A, and 1B and bone anchor of FIG. 1C according to an embodiment of the present invention.

FIGS. 1A-1G are views of an adaptive stabilization system including an adaptive spinal rod according to an embodiment of the present invention. FIG. 1A is an exploded view showing the components of an adaptive spinal rod. FIG. 1B is a perspective view of the assembled adaptive spinal rod. FIG. 1C shows a perspective view of a bone anchor suitable for mounting the adaptive spinal rod to a vertebra. FIG. 1D shows a spinal prosthesis assembly including the adaptive spinal rod, a bone anchor and a conventional pedicle screw. FIGS. 1E, 1F and 1G are sectional views illustrating the kinematics of the bone anchor relative to the adaptive spinal rod.

Referring first to FIG. 1A, which is an exploded view of the components of an adaptive spinal rod 100. Adaptive spinal rod 100 has three components: rod 110 including housing 120, ball 130 and cap 140. Rod 110 is connected at one end to housing 120. Rod 110 is preferably similar in size, shape and material to standard spinal rods. Rod 110 is preferably adapted for mounting to a standard pedicle screw or polyaxial screw (not shown). Rod 110 is, in preferred embodiments, a cylinder of about 5 mm to 6.5 mm in diameter and from 35 mm to 100 mm in length. Housing 120 is preferably in the form of a flattened disc. Housing 120 has a slot 122 passing there through. Slot 122 is shaped to receive ball 130 from open side 124 however, the closed side 126 of slot 122 is too small for ball 130 to pass. Slot 122 and thus linear race 102 can be elongated to allow ball 130 to slide in slot 122 as explained below. It is to be understood that linear race 102, in addition to being elongated such that ball 130 can move linearly along the direction of the longitudinal axis of rod 110, can be oval and/or elliptical shaped and/or rectangular with rounded corners and/or race-track shaped such that ball 130 can move linearly in any direction. Further, slot 122 and thus linear race 102 can be an enlarged sphere shaped such that ball 130 can move in any linear direction relative to the sphere as well as pivoting and rotating relative to linear race 102. Open side 124 of slot 122 is shaped to receive cap 140. Closed side 126 of slot 122 has a curved surface 128 adapted to engage ball 130. In one embodiment curved surface 128 has the same radius of curvature as ball 130. Cap 140 can be force fit or welded in place to the housing 120 to hold ball 130 in place. In preferred embodiments, rod 110 and housing 120 are made in one piece from titanium or titanium alloy.

Ball 130 is in the form of a sphere truncated on two opposing sides 132, 134. An aperture 136 passes through ball 130 from side 132 to side 134. As shown in FIG. 1A, one end of aperture 136 is provided with tool engagement features 138 (a hexagonal depression is shown) which allow ball 130 to be engaged and turned by a tool. The other end of aperture 136 has a threaded wall 139 adapted to allow ball 130 to be secured to a threaded screw (not shown). Thus, ball 130 is adapted to be secured to a threaded shaft (not shown) without using a separate nut. In alternative embodiments aperture 136 is not provided with tool engagement features 138 or threaded wall 139 and is adapted to be secured to a threaded shaft (not shown) with a separate threaded nut/fastener (not shown).

Cap 140 is adapted to fit within slot 122 of housing 120. Cap 140 has a cap slot 142 therethrough. The open side 144 of slot 142 is configured to admit a portion of ball 130. The closed side 146 of slot 142 is too small for ball 130 to pass. The interior of slot 142 has a curved surface 148 adapted to engage ball 130. In one embodiment curved surface 148 has the same radius of curvature as ball 130.

During assembly, ball 130 is placed into slot 122 of housing 120. Cap 140 is then secured into slot 122 of housing 120 trapping or containing ball 130 between cap 140 and housing 120. FIG. 1B shows a fully assembled adaptive spinal rod 100 in which ball 130 is positioned between cap 140 and housing 120. Slot 122 of housing 120 and slot 142 of cap 140 cooperate to from a linear race 102 in which ball 130 is trapped or contained. Although ball 130 is trapped or contained within linear race 102, ball 130 can pivot and rotate within linear race 102 as shown by arrows 160, 162. Ball 130 can also slide a small distance along linear race 102 as shown by arrow 164. As shown in FIG. 1B, aperture 136 of ball 130 is accessible after ball 130 has been secured between cap 140 and housing 120. In adaptive spinal rod 100 as assembled, aperture 136 of ball 130 is accessible and configured for mounting adaptive spinal rod 100 to a threaded shaft of a pedicle screw as shown, for example in FIG. 1C. In combination, the surface of ball 130, and the linear race 102 form a sliding ball-joint 101.

FIG. 1C shows a bone anchor 150 configured for attachment of adaptive spinal rod 100 to a vertebra. As shown in FIG. 1C, bone anchor 150 includes a threaded shaft 152 at the distal end. Threaded shaft 152 is sized and configured for engaging a vertebra. In preferred embodiments threaded shaft 152 is sized and configured for implantation in the pedicle of a vertebra. Attached to threaded shaft 152 is head 154. Head 154 includes surface features 155 which permit head to be engaged by a tool to rotate head 154 and threaded shaft 152 and drive bone anchor 150 into a desired implant location. Protruding proximally from head 154 is a mount 156. Mount 156 has a threaded exterior surface 157 to which ball 130 of FIGS. 1A and 1B can be mounted. Protruding proximally of mount 156 is key 158. Key 158 is shaped such that the key 158 can be engaged by a driver for implanting bone anchor 150 and/or attaching ball 130. For example, key 158 has, in some embodiments, a hexagonal or octagonal cross-section. At the base of key 158 is a groove 159. Groove 159 reduces the cross-section of material such that the key 158 is designed to breakaway when a predetermined amount of torque is applied to key 158. The breakaway torque is determined by the shape of groove 159 and the remaining cross-section of material.

FIG. 1D shows the relationship between a spinal prosthesis 104 and a spine 190. Spinal prosthesis 104 includes, in this embodiment: adaptive spinal rod 100 of FIGS. 1A and 1B; bone anchor 150 of FIG. 1C; and a conventional spinal screw 170. Spinal screw 170 is, in some embodiments, a polyaxial pedicle screw. As shown in FIG. 1D, adaptive spinal rod 100 is secured at one end to the bone anchor 150 of FIG. 1C and at the other end to conventional spinal screw 170. Ball 130, trapped or contained within linear race 102, has been secured to mount 156 of bone anchor 150. Breakaway key 158 is broken away from mount 156 during implantation and removed from the patient. Rod 110 has been secured into a slot 172 in a head 174 of spinal screw 170 by a set screw 173. Set screw 173 secures rod 110 in a fixed position relative to head 174 and also, in some embodiments, locks the position of head 174 relative to the threaded screw shaft 176 of spinal screw 170.

In spinal prosthesis 104, rod 110 and housing 120 of adaptive spinal rod 100 are secured in a fixed position, as shown in FIG. 1D, relative to spinal screw 170. However, ball 130 is still able pivot rotate and slide in linear race 102 relative to housing 120 of adaptive spinal rod 100 (see FIG. 1C). Consequently, with bone anchor 150 secured to adaptive spinal rod 100 through ball 130, bone anchor 150 is still able to slide, pivot and rotate relative to rod 110 and spinal screw 170. (See FIGS. 1E, 1F and 1G).

Referring again FIG. 1D which shows the relationship between a spinal prosthesis 105 and a spine 190. Bone anchor 150 is implanted in a vertebra 192a passing through pedicle 194a into spinal body 196a. Spinal screw 170 is implanted in a vertebra 192b passing through a pedicle 194b into spinal body 196b. A second spinal screw 170 is implanted in a vertebra 192c passing through a pedicle 194c into spinal body 196c. Spinal screws 170 and rod 110b hold vertebrae 192b and 192c in fixed relationship. This embodiment of a spinal prosthesis is suitable for use for example, where vertebrae 192b and 192c are to be fused together. As shown in FIG. 1D, where bone anchor 150 and rod 110b provides load-sharing and permits a controlled range of motion between the adjacent vertebrae 192a, 192b. Thereby stabilizing a level of the spine 190 while restoring and/or preserving some natural motion of the vertebrae 192a, 192b at that level. This configuration can, in some embodiments, be utilized to prevent adjacent segment deterioration by supporting a spinal motion segment adjacent a spinal fusion.

FIGS. 1E, 1F and 1G show the kinematics of bone anchor 150 relative to rod 110 of adaptive spinal rod 100 when assembled as part of an adaptive spinal prosthesis. FIG. 1E shows a section through bone anchor 150 and adaptive spinal rod 100 in a substantially saggital plane. FIG. 1F shows a section through bone anchor 150 and adaptive spinal rod 100 in a transverse plane. FIG. 1G shows a section through bone anchor 150 and adaptive spinal rod 100 in a substantially dorsal plane through the middle of the housing 120.

Referring first to FIG. 1E which shows a section through bone anchor 150 and adaptive spinal rod 100 in a substantially saggital plane (vertical and including the longitudinal axis of bone anchor 150). The dotted outlines of bone anchor 150 illustrate a range of possible movements of bone anchor 150 in the saggital plane. As shown in FIG. 1E, ball 130 is trapped or contained between cap 140 and housing 120 to form a sliding ball-joint 101. Ball 130 can move within limits imposed by contact with housing 120 and cap 140. Bone anchor 150 thus can pivot and translate relative to rod 110 in the plane shown.

In the saggital plane shown in FIG. 1E, the sliding ball-joint 101 allows bone anchor 150 a limited vertical range of movement (shown by arrow 180). The translation is limited by contact between ball 130, cap 140 and, in some embodiments, bone anchor 150. The desired range of vertical motion 180, and thus the dimensions of sliding ball-joint 101, are selected based upon the anatomical and functional needs of a patient. In embodiments, the range of vertical movement is limited to less than 5 mm. In preferred embodiments, the range of horizontal and vertical movement is limited to less than 1.5 mm. The length of linear race 102 (along the long axis of rod 110) controls the vertical range of movement.

In the saggital plane shown in FIG. 1E, the sliding ball-joint 101 also allows bone anchor 150 a limited angular range of movement which corresponds to spinal flexion/extension (shown by arrow 182). The range of angular movement translation is limited by contact between ball 130, housing 120 and cap 140 and, in some embodiments, mount 156. The desired range of angular motion 182, and thus the shape of ball 130, housing 120 and cap 140 and, in some embodiments, mount 156 are selected based upon the anatomical and functional needs of a patient. In embodiments, the range of angular movement in the saggital plane is limited to less than 15 degrees. In preferred embodiments, the range of angular movement in the saggital plane is limited to less than 15 degrees.

In the transverse plane shown in FIG. 1F, the sliding ball-joint 101 allows bone anchor 150 a limited angular range of movement which corresponds to spinal rotation (shown by arrow 184). The range of angular movement is limited by contact between ball 130, housing 120 and cap 140 and, in some embodiments, mount 156. The desired range of angular motion 184, and thus the shape of ball 130, housing 120 and cap 140 and, in some embodiments, mount 156 are selected based upon the anatomical and functional needs of a patient. In embodiments, the range of angular movement in the transverse plane is limited to less than 10 degrees. In preferred embodiments, the range of angular movement in the transverse plane is limited to less than 15 degrees. The range of angular movement in the transverse plane can be different than the range in the vertical plane. The range of angular movement in the transverse plane need not be the same as the range of angular movement in the saggital plane (see FIG. 1E).

Referring next to FIG. 1G which shows a section through bone anchor 150 and adaptive spinal rod 100 in a substantially dorsal plane (vertical and perpendicular to the longitudinal axis of bone anchor 150). As shown in FIG. 1G, ball 130 is trapped or contained in linear race 102 formed by cap 140 in conjunction with housing 120. Ball 130 can move within linear race 102. Bone anchor 150 is oriented either directly into or directly out of the page in this transverse view through housing 120. Bone anchor 150 is mounted to ball 130 and thus can move relative to rod 110 with one angular degree of freedom and one linear degree shown in this view.

In the dorsal plane shown in FIG. 1G, sliding ball-joint 101 allows bone anchor 150 the limited vertical range of movement 180 as described above. Rotation of ball 130 within sliding ball-joint 101 is unrestricted, allowing bone anchor 150 to rotate freely (360+ degrees) as shown by arrow 186 which corresponds to lateral spinal twisting. The bone anchor 150 rotates freely around the longitudinal axis of the bone anchor. The range of rotation 186 is not limited in this embodiment. However features to limit such rotation could be designed into one or more of bone anchor 150, ball 130, cap 140, and housing 120. The desired range of rotation 186, can be selected, if necessary or desirable, based upon the anatomical and functional needs of a patient.

Figure 2D:
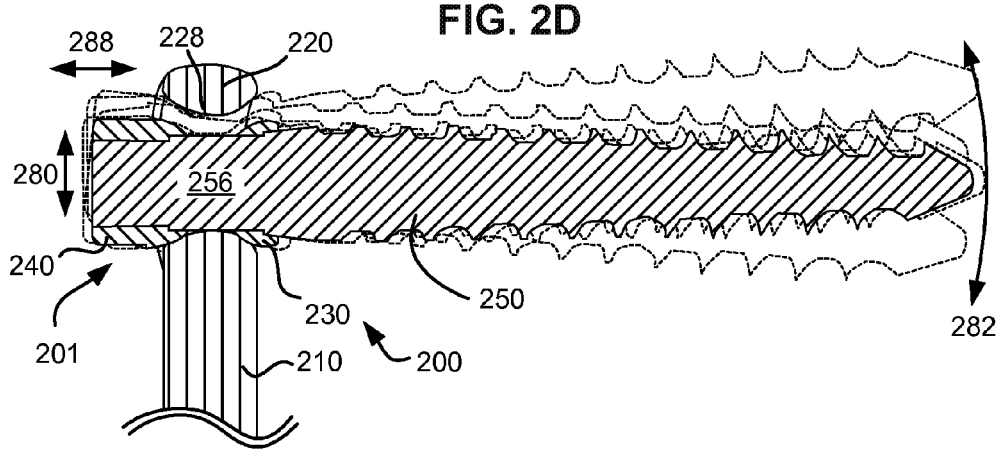
FIG. 2D is a saggital section of the assembly of FIG. 2C as implanted.
Figure 2E:
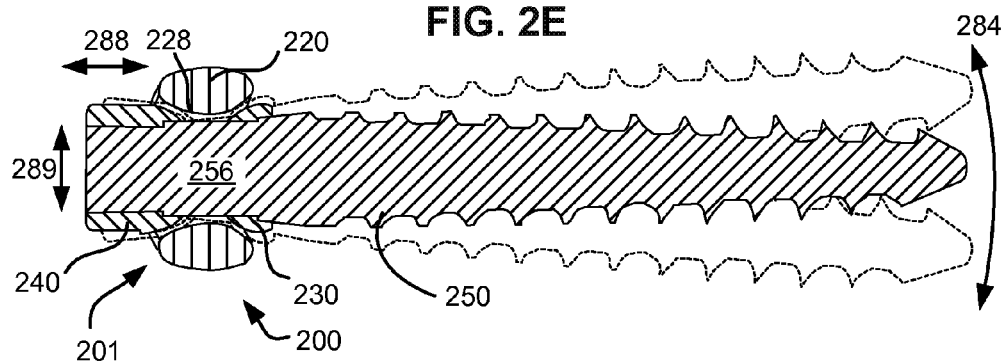
FIG. 2E is a transverse section of the spinal prosthesis of FIG. 2C as implanted.
Figure 2F:
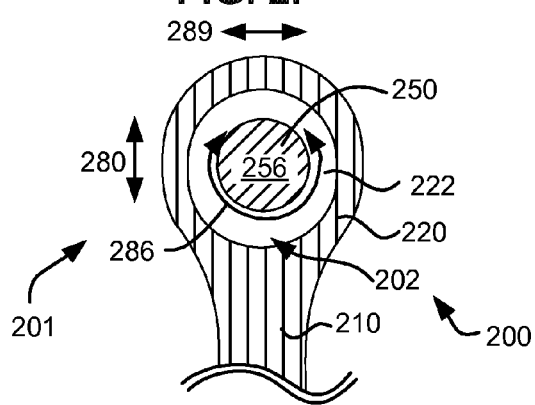
FIG. 2F is a dorsal section of the spinal prosthesis of FIG. 2C as implanted.

FIGS. 2A-2F are views of an alternative adaptive stabilization system including an adaptive spinal rod according to an embodiment of the present invention. FIG. 2A is an exploded view showing the components of an adaptive spinal rod. FIG. 2B shows a perspective view of a bone anchor suitable for mounting the adaptive spinal rod to a vertebra. FIG. 2C is a perspective view of the assembled adaptive spinal rod and bone anchor. FIGS. 2D, 2E and 2F are sectional views illustrating the kinematics of the bone anchor relative to the adaptive spinal rod.

Referring first to FIG. 2A, which is an exploded view of the components of an adaptive spinal rod 200. Adaptive spinal rod 200 has three components: rod 210 including housing 220, half-ball 230 and half-ball retainer 240. Rod 210 is connected at one end to housing 220. Rod 210 is similar in size, shape and material to standard spinal rods. Rod 210 is adapted for mounting to a standard pedicle screw or polyaxial screw (not shown). Rod 210 is in preferred embodiments, preferably a cylinder of about 5 mm to 6.5 mm in diameter and from 35 mm to 200 mm in length. Housing 220 is preferably in the form of a flattened disc.

Housing 220 has a slot 222 passing there through. Slot 222 has convex walls and slot 222 is thus wider at the openings of slot 222 than in the interior of slot 222. Thus half-ball 230 can partially enter one side of slot 222, but cannot pass entirely through slot 222. Likewise half-ball retainer 240 can partially enter one side of slot 222, but cannot pass entirely through slot 222. In preferred embodiments, rod 210 and housing 220 are made in one piece from titanium or titanium alloy.

Half-ball 230 is in the form of a hemisphere. An aperture 236 passes through half-ball 230 from domed side 232 to flat side 234. As shown in FIG. 2A, aperture 236 is, in some embodiments, provided with tool engagement features which allow ball 230 to engage a mounting post (for example threads or a hexagonal section.

Hall-ball retainer 240 in the form of a hemisphere with a nut extending from the flat surface. An aperture 246 passes through half-ball retainer 240 from domed side 242 to flat side 244. As shown in FIG. 2A, part of the surface of half-ball retainer 240 is provided with tool engagement features 248 (splines are shown) which allow half-ball retainer 240 to be engaged and turned by a tool. The interior of aperture 246 has a threaded wall 249 adapted to allow half-ball retainer 240 to be secured to a threaded screw (bone anchor 250 of FIG. 2B). Thus, half-ball retainer 240 is adapted to be secured to a threaded shaft (thread 258 of FIG. 2B) without using a separate nut. In alternative embodiments half-ball retainer 240 can be provided in two pieces including for example a half-ball component and a standard nut.

FIG. 2B, shows a bone anchor 250 configured for attachment of adaptive spinal rod 200 to a vertebra. As shown in FIG. 2B, bone anchor 250 includes a threaded shaft 252 at the distal end. Threaded shaft is sized and configured for engaging a vertebra. In preferred embodiments threaded shaft 252 is sized and configured for implantation in the pedicle of a vertebra. At the proximal end of threaded shaft 252 is a head 254 which has, in some embodiments, tool engagement features (not shown). Protruding proximally from head 254 is mount 256. Mount 256 has a cylindrical exterior surface 257 to which ball 230 of FIG. 2A can be secured. Protruding proximally of mount 256 is threaded shaft 258. Threaded shaft 258 is adapted for attaching half-ball retainer 240. In the proximal end of threaded shaft 258 is an aperture 259. Aperture 259 is shaped such that aperture 259 can be engaged by a driver for implanting bone anchor 250 and/or attaching half-ball retainer 240. For example, aperture 259 has, in some embodiments, a hexagonal or octagonal cross-section. In alternative embodiments aperture 259 is replaced with a breakaway key such as key 158 of FIG. 1C. In combination, the domed surfaces of half-ball 230, and half-ball retainer 240 and the convex surface of slot 222 form an alternative sliding ball-joint 201.

FIG. 2C is a perspective view of adaptive spinal rod 200 in combination with bone anchor 250. As shown in FIG. 2C, half-ball 230 is placed over mount 256 (FIG. 2B). Slot 222 is then placed over mount 256 (FIG. 2B). A portion of the domed surface 232 of half-ball 230 enters slot 222. Finally half-ball retainer 240 is secured the threaded shaft 258 (FIG. 2B). A portion of the domed surface 242 of half-ball retainer 240 enters slot 222. Half-ball 230 and half-ball retainer 240 may, in some but not all embodiments, contact one another inside slot 222. Upon assembly slot 222 performs as race 202 for half-ball 230 and half-ball retainer 240. Thus, bone anchor 250 can slide, pivot and rotate relative to housing 220 and rod 210 of adaptive spinal rod 200. It is to be understood that slot 222 and thus race 202 can be linear and also can be configured in accordance with the various configurations of slot 122 and linear race 102 shown in the embodiments of FIGS. 1A-1H.

In embodiments, adaptive spinal rod 200 and bone anchor 250 can be used in place of adaptive spinal rod 100 and bone anchor 150 to create a spinal prosthesis similar to spinal prosthesis 104 of FIG. 1D. In such a spinal prosthesis, rod 210 and housing 220 of adaptive spinal rod 200 are secured in a fixed position, by a pedicle screw. However, slot 222 is still able pivot rotate and slide relative to half-ball 230 and half-ball retainer 240. Consequently, with bone anchor 250 secured to adaptive spinal rod 200 by sliding ball-joint 201 is still able to slide, pivot and rotate relative to rod 210. (See FIGS. 2D, 2E and 2F). Adaptive spinal rod 200 is configured to provide load-sharing and permit a controlled range of motion between adjacent vertebrae. Thereby, stabilizing a level of the spine while restoring and/or preserving some natural motion of the vertebrae at that level.

FIGS. 2D, 2E and 2F show the kinematics of bone anchor 250 relative to rod 210 of adaptive spinal rod 200 when assembled as part of a spinal prosthesis. FIG. 2D shows a section through bone anchor 250 and adaptive spinal rod 200 in a substantially saggital plane. FIG. 2E shows a section through bone anchor 250 and adaptive spinal rod 200 in a transverse plane. FIG. 2F shows a section through bone anchor 250 and adaptive spinal rod 200 in a substantially dorsal plane through the middle of the housing 220.

Referring first to FIG. 2D which shows a section through bone anchor 250 and adaptive spinal rod 200 in a substantially saggital plane (vertical and including the longitudinal axis of bone anchor 250). The dotted outlines of bone anchor 250 illustrate a range of possible movements of bone anchor 250 in the saggital plane. As shown in FIG. 2D, half-ball 230 and half-ball retainer 240 trap or contain the convex surface of slot 222. Slot 222 can move within limits imposed by contact with half-ball 230 and half-ball retainer 240 (and, in some embodiments, mount 256. Bone anchor 250 thus can pivot and translate relative to rod 210 in the plane shown.

In the saggital plane shown in FIG. 2D, the sliding ball-joint 201 allows bone anchor 250 a limited vertical range of movement (shown by arrow 280) and a limited horizontal range of movement 288. The translation is limited by contact between slot 222 and half-ball 230, half-ball retainer 240 and, in some embodiments, mount 256. The desired range of vertical motion 280 and horizontal motion 288, and thus the dimensions of sliding ball-joint 201, are selected based upon the anatomical and functional needs of a patient. In embodiments, the range of horizontal and vertical movement is limited to less than 5 mm. In preferred embodiments, the range of horizontal and vertical movement is limited to less than 2.5 mm. The horizontal and vertical range of movement need not be the same. The width of slot 222 (perpendicular to the long axis of rod 210) controls the horizontal range of movement while the length of slot 222 (along the long axis of rod 210) controls the vertical range of movement.

In the saggital plane shown in FIG. 2D, the sliding ball-joint 201 also allows bone anchor 250 a limited angular range of movement which corresponds to spinal flexion/extension (shown by arrow 282). The range of angular movement translation is limited by contact between slot 222 and half-ball 230, half-ball retainer 240 and, in some embodiments, mount 256. The desired range of angular motion 282, and thus the shape of slot 222 and half-ball 230, half-ball retainer 240 and, in some embodiments, mount 256 are selected based upon the anatomical and functional needs of a patient. In embodiments, the range of angular movement in the saggital plane is limited to less than 20 degrees. In preferred embodiments, the range of angular movement in the saggital plane is limited to less than 20 degrees.

In the transverse plane shown in FIG. 2E, the sliding ball-joint 201 allows bone anchor 250 a limited horizontal range of movement (shown by arrow 289) and a limited horizontal range of movement 288. The translation is limited by contact between slot 222 and half-ball 230, half-ball retainer 240 and, in some embodiments, mount 256. The desired range of horizontal motion 288 and horizontal motion 289, and thus the dimensions of sliding ball-joint 201, are selected based upon the anatomical and functional needs of a patient. In embodiments, the range of horizontal and vertical movement is limited to less than 5 mm. In preferred embodiments, the range of horizontal and vertical movement is limited to less than 2.5 mm. The horizontal ranges of movement need not be the same an can be adjusted by changing, dimensions of the sliding ball-joint 201, including, for example: the curvature of the slot 222, half-ball 230, and half-ball retainer 240, the width of slot 222, and gap between half-ball 230, and half-ball retainer 240.

In the transverse plane shown in FIG. 2E, the sliding ball-joint 201 also allows bone anchor 250 a limited angular range of movement which corresponds to spinal rotation (shown by arrow 284). The range of angular movement is limited by contact between slot 222 and half-ball 230, half-ball retainer 240 and, in some embodiments, mount 256. The desired range of angular motion 284, and thus the shape of slot 222 and half-ball 230, half-ball retainer 240 and, in some embodiments, mount 256 are selected based upon the anatomical and functional needs of a patient. In embodiments, the range of angular movement in the transverse plane is limited to less than 20 degrees. In preferred embodiments, the range of angular movement in the transverse plane is limited to less than 20 degrees. The range of angular movement in the transverse plane can be different than the range in the vertical plane.

Referring next to FIG. 2F which shows a section through bone anchor 250 and adaptive spinal rod 200 in a substantially dorsal plane (vertical and perpendicular to the longitudinal axis of bone anchor 250). As shown in FIG. 2F, mount 256 is trapped or contained in linear race 202 formed slot 222 and half-ball 230, half-ball retainer 240. Mount 256 can move within race 202. Bone anchor 150 can thus move relative to rod 210 with one angular degree of freedom and one linear degree shown in this view. Bone anchor 250 is oriented either directly into or directly out of the page in this transverse view through housing 220.

In the dorsal plane shown in FIG. 2F, sliding ball-joint 201 allows bone anchor 250 the limited horizontal and vertical range of movement (shown by arrows 280 and 289) as described above. Rotation of bone anchor 250 within slot 222 is unrestricted, allowing bone anchor 250 to rotate freely (360+ degrees) as shown by arrow 286 which corresponds to lateral spinal twisting. The bone anchor 250 rotates freely around the longitudinal axis of the bone anchor. The range of angular motion 286 is not limited in this embodiment. However, features to limit such rotation could be designed into one or more of bone anchor 250 and housing 220. The desired range of rotation 286, can be selected, (if necessary) based upon the anatomical and functional needs of a patient.

Figure 3A:
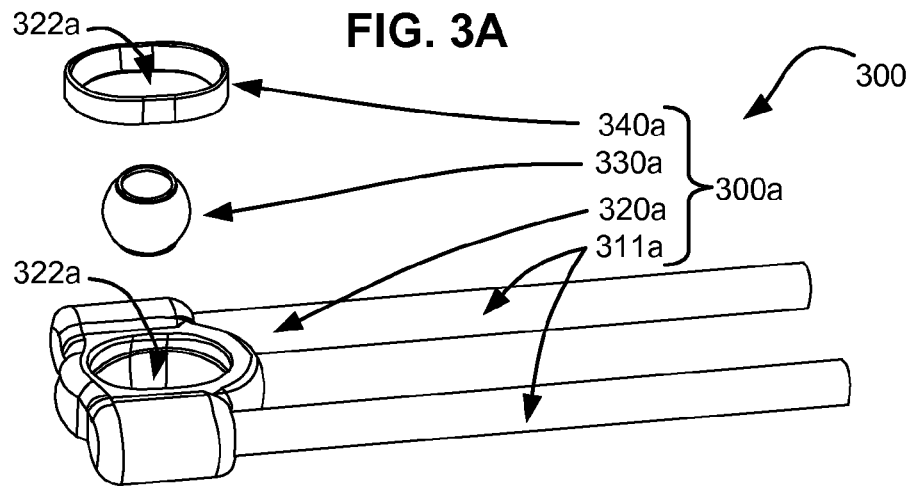
FIG. 3A is an exploded view of a first segment of a two-level adaptive spinal rod according to an embodiment of the present invention.
Figure 3B:
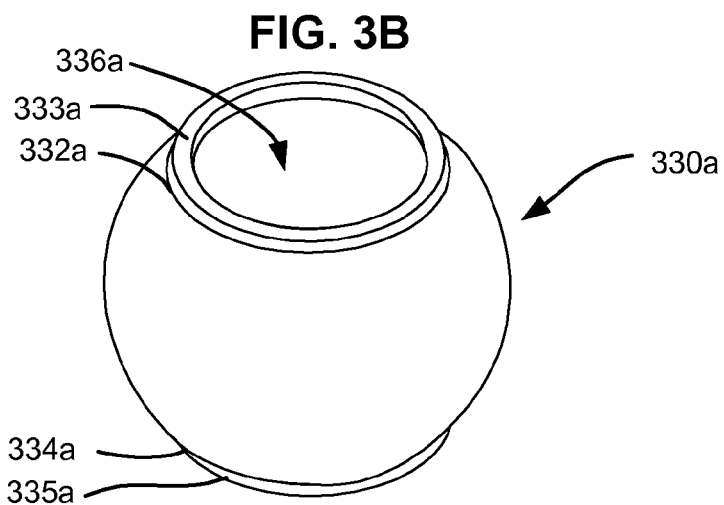
FIG. 3B is an enlarged view illustrating features of a ball for use in a sliding ball-joint according to an embodiment of the invention.
Figure 3C:
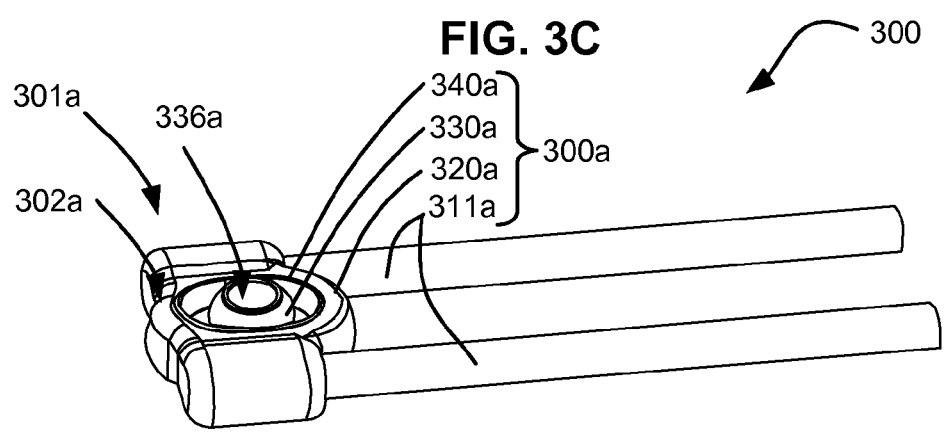
FIG. 3C is a perspective view of the first segment of a two-level adaptive spinal rod according to an embodiment of the present invention.
Figure 3D:
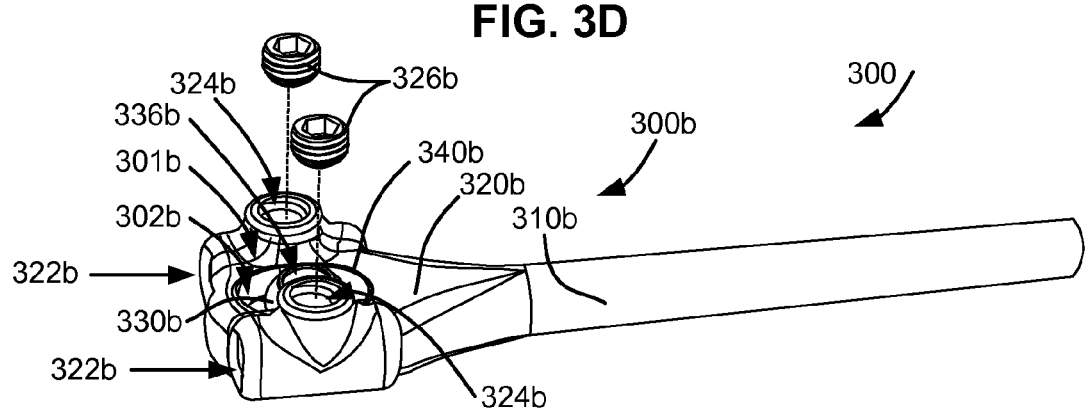
FIG. 3D is a perspective view of the second segment of a two-level adaptive spinal rod according to an embodiment of the present invention.
Figure 3E:
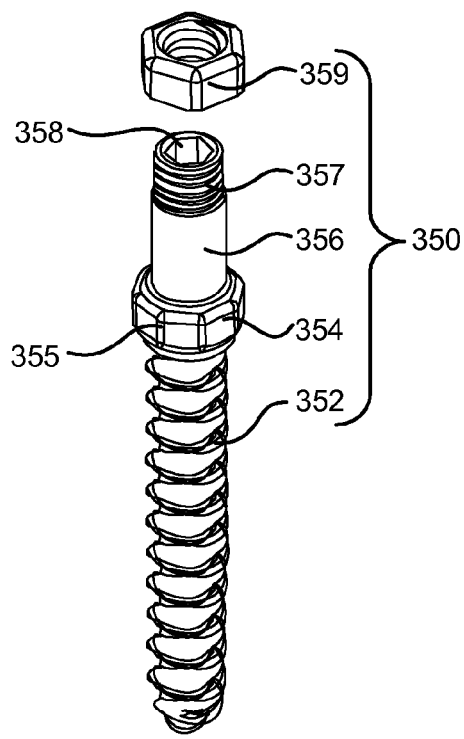
FIG. 3E is a perspective view of a bone anchor for use with the two-level adaptive spinal rod according to an embodiment of the present invention.
Figure 3F:
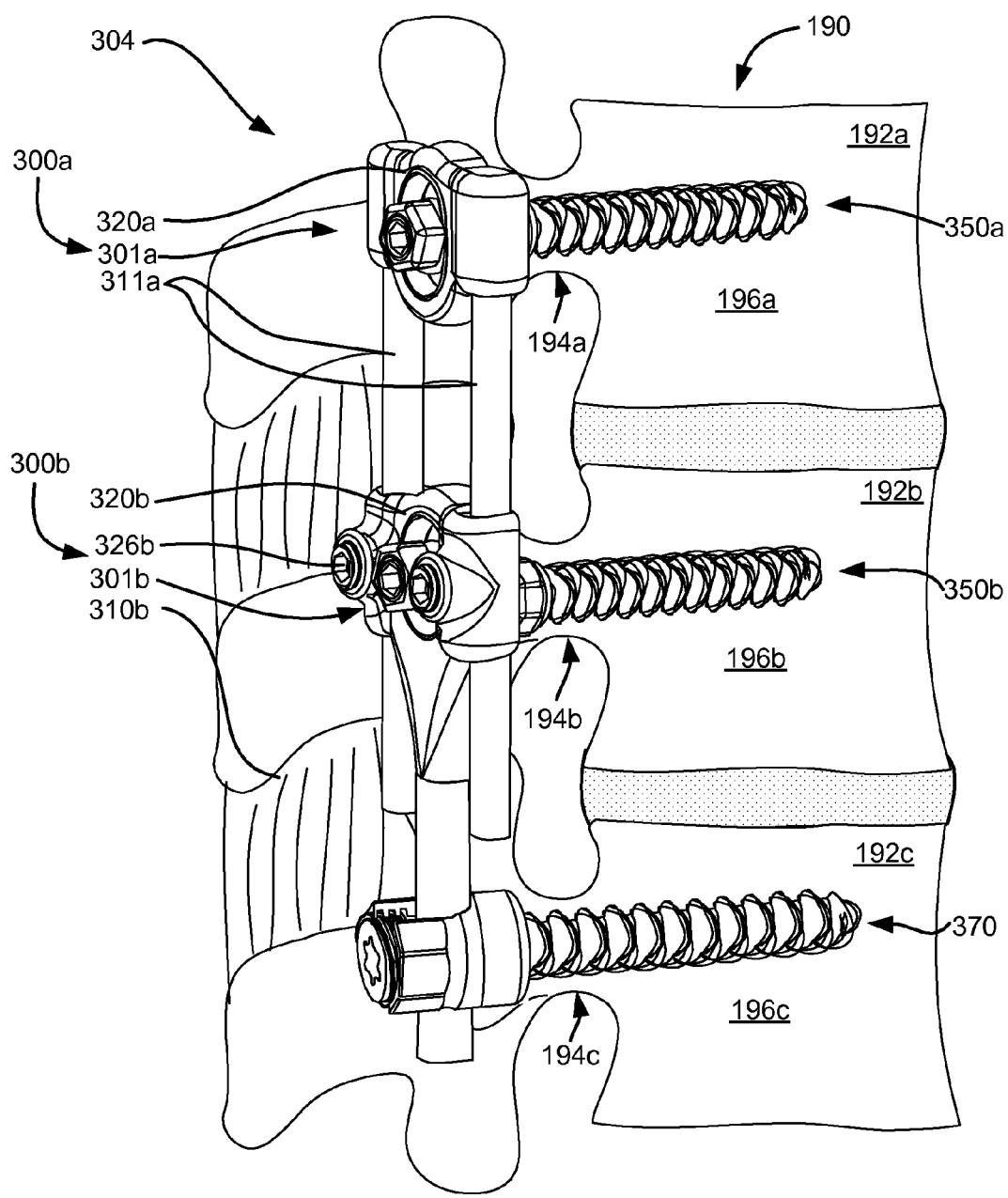
FIG. 3F is a perspective view of a spinal prosthesis including the two-level adaptive spinal rod of FIGS. 1A, and 1B and bone anchor of FIG. 1C according to an embodiment of the present invention.

FIGS. 3A-3F show views of a two-level adaptive stabilization system including an adaptive spinal rod according to an embodiment of the present invention. FIGS. 3A-3C show views of the first segment and components. FIG. 3D shows the second segment. FIG. 3E shows a compatible bone. FIG. 3F shows a perspective view of a spinal prosthesis including both segments of the two-level adaptive spinal rod of FIGS. 3A-3E.

Referring first to FIG. 3A, which is an exploded view of the components of the first segment 300a of an adaptive spinal rod 300. First segment 300a includes rods 311a, housing 320a, ball 330a and cap 340a. Rods 311a are connected to either side of housing 320a. Rods 311a are similar in shape and material to standard spinal rods. Rods 311a are adapted for mounting to the second segment 300b (See FIG. 3D) of adaptive spinal rod 300 (See FIG. 3D). Rods 311a are, in preferred embodiments, preferably cylinders about 4 mm to 4.5 mm in diameter and from 35 mm to 100 mm in length. Housing 320a is preferably in the form of a flattened disc. Housing 320a has a slot 322a passing there through (similar in design in function to slot 122 of FIG. 1A). Slot 322a is shaped to receive ball 330a. Cap 340a is adapted to fit within slot 322a of housing 320a. Cap 340a has a cap slot 342a therethrough (see, e.g. cap 140 of FIG. 1A).

FIG. 3B shows an enlarged view of ball 330a. Ball 330a is in the form of a sphere truncated on two opposing sides 332a, 334a. An aperture 336a passes through ball 330a from side 332a to side 334a. As shown in FIG. 3B, ball 330a includes a rim 333a surrounding aperture 336a on side 332a and a rim 335a surrounding aperture 336a on side 334a. Ball 330a is adapted to be secured to a shaft (mount 356 of FIG. 3E) with a separate nut. In alternative embodiments, aperture 336a is provided with tool engagement features and/or threads and is adapted to be secured to a threaded shaft (not shown) without a separate threaded nut/fastener (not shown). Rim 333a and rim 335a are configured to interaction with the housing 320a and cap 340a to control range of motion. The dimensions of rim 333a and rim 335a are thus selected based on the range of motion desired. In general, where the rim has a larger outside the diameter it will there is less clearance between the rim and the housing 320a and/or cap 340a and therefore less range of motion.

As shown in FIG. 3C, during assembly, ball 330a is placed into slot 322a of housing 320a. Cap 340a is then secured into slot 322a of housing 320a trapping/containing ball 330a between cap 340a and housing 320a. FIG. 3C shows first segment 300a fully assembled—ball 330a is positioned between cap 340a and housing 320a. Slot 322a of housing 320a and slot 342a of cap 340a cooperate to form a linear race 302a in which ball 330a is trapped/contained. Although ball 330a is trapped within race 302a, ball 330a can pivot, slide, and rotate within race 302a. In combination, the surface of ball 330a, and the race 302a form a sliding ball-joint 301a. It is to be understood that the slot 322a and thus, race 302a can be linear and also can be configured in accordance with the various configurations of slot 122 and linear race 102 shown and described in the embodiments of FIGS. 1A-1H. Aperture 336a of ball 330a is accessible and configured for mounting adaptive spinal rod 300 to a pedicle screw (See, FIG. 3F).

FIG. 3D shows a perspective view of the second segment 300b of an adaptive spinal rod 300. Second segment 300b includes rod 310b, housing 320b, ball 330b and cap 340b. Rod 310b is connected to the middle of housing 320b. Rod 310b is preferably similar in shape and material to a standard spinal rod. Rod 310b is adapted for mounting to a standard spinal screw/pedicle screw. Rod 310b is, in preferred embodiments, a cylinder about 5 mm to 6.5 mm in diameter and from 35 mm to 150 mm in length. Housing 320b is preferably in the form of a flattened disc. Housing 320b and cap 340b trap or contain ball 330b. Housing 320b and cap 340b cooperate to form a linear race 302b in which ball 330 can slide, pivot and rotate. Ball 330b and linear race 302b together comprise a ball-joint 301b. Ball 330b is of the same design as ball 330a (See FIG. 3B). Ball 330b includes an aperture 336b for securing a bone anchor.

On either side of housing 320b are bores 322b. Bores 322b run parallel to rod 310b and pass through housing 320b. Bores 322b are configured to receive rods 311a of first segment 300a (see FIG. 3A) in a sliding fashion. Each of bores 322b intersects with a threaded bore 324b. A set screw 326b is provided for each of threaded bores 324b. The set screws 326b when driven in threaded bores 324b are adapted to intersect bores 322b and engage and lock rods 311a of first segment 300a (see FIG. 3A).

FIG. 3E, shows a bone anchor 350 configured for attachment of adaptive spinal rod 300 to a vertebra. As shown in FIG. 3E, bone anchor 350 includes a threaded shaft 352 at the distal end. Threaded shaft 352 is sized and configured for engaging a vertebra. In preferred embodiments threaded shaft 352 is sized and configured for implantation in the pedicle of a vertebra. Attached to threaded shaft 352 is head 354. Head 354 includes surface features 355 which permit head to be engaged by a tool to rotate head 354 and threaded shaft 352 and drive bone anchor 350 into a desired implant location. Protruding proximally from head 354 is a mount 356. Mount 356 has a smooth exterior surface to receive ball 330 of FIG. 3B. Protruding proximally of mount 356 is a threaded shaft 357 for attaching a nut 359. In the proximal end of threaded shaft 357 is an aperture 358. Aperture 358 is shaped such that the aperture 358 can be engaged by a driver for implanting/removing bone anchor 350 and/or attaching nut 359. For example, aperture 358 has, in some embodiments, a hexagonal or octagonal cross-section.

Figure 3G:
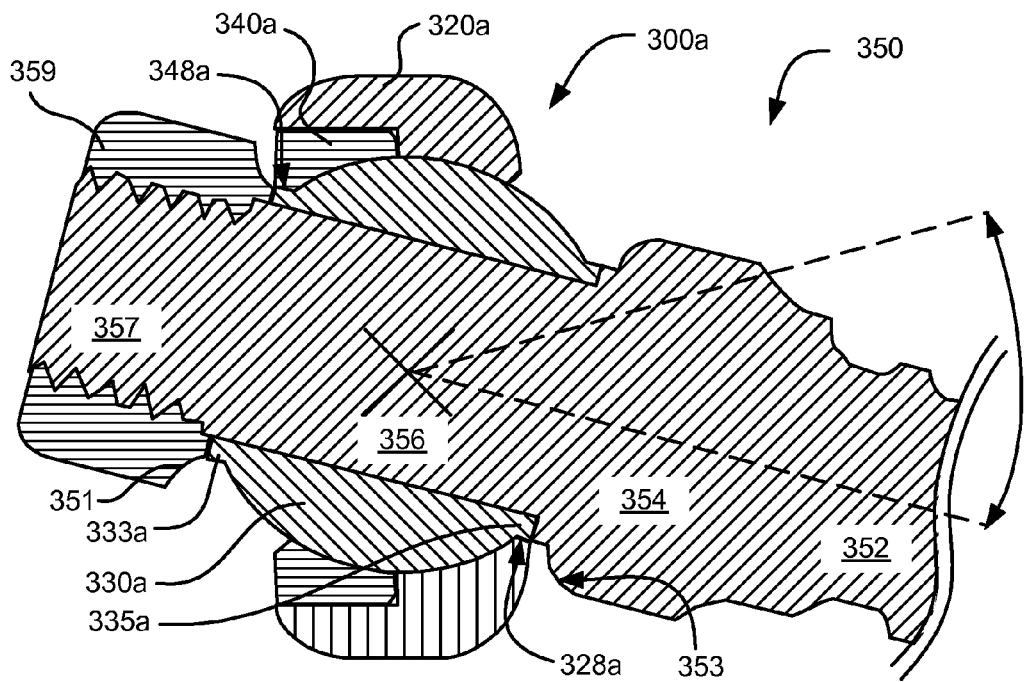
FIG. 3G is a partial sectional view illustrating motion limiting features of adaptive spinal rod according to embodiments of the present invention.

FIG. 3G is a partial sectional view of adaptive spinal rod 300 through ball 330a and housing 320a illustration features which serve to limit angulation of a bone anchor 350 relative to housing 320a. FIG. 3G shows bone anchor 350 at one limit to its range of angulation with respect to housing 320a. At the limit of angulation, rim 335a contacts limit surface 328a of housing 320a. Additionally, in some embodiments, rim 333a of ball 330a comes into contact with a limit surface 348a of cap 340a. In preferred embodiments, to reduce wear, limit surfaces 328a and 348a are substantially parallel to the surface of rims 333a and 335a of ball 330a with which they make contact when the rims and limit surfaces make contact. Note also that nut 359 is designed so as not to make contact with housing 320a or cap 340a even at the limit of angulation. In the embodiment shown in FIG. 3G, nut 359 has a relief 351 to prevent contact between nut 359 and cap 340a. Note further that screw 350 is also designed so as not to make contact with housing 320a or cap 340a even at the limit of angulation. In the embodiment shown in FIG. 3G, head 354 has a relief 353 to prevent contact between head 354 and housing 320a. In alternative embodiments, limit surfaces are provided on the bone screw and/or nut and/or another device, for example a washer. The limit surfaces are position to contact e.g. the housing or cap of an adaptive spinal rod to limit the range of motion in one or more axes.

FIG. 3F shows a spinal prosthesis 304 incorporating adaptive spinal rod 300. As shown in FIG. 3F, the first segment 300a of the adaptive spinal rod 300 is mounted by a bone anchor 350a to vertebra 192a. The second segment 300b of the adaptive spinal rod 300 is mounted by a bone anchor 350b to vertebra 192b. Rods 311a of first segment 300a pass through the housing 320b of second segment 300b. When distance between first housing 320a and second housing 320b is suitable for the functional and anatomic needs of the patient, set screws 326b are tightened thereby locking rods 311a in place. Rod 310b of second segment 300b is secured to vertebra 192c by a convention spinal screw 370 as previously described.

After implantation and assembly, rod 310b housing 320b, rods 311a and housing 320a are all held in substantially fixed relationship to vertebra 192c by spinal screw 370. However sliding ball-joint 301b enables the bone anchor 350b implanted in vertebra 192b to slide, pivot and rotate relative to housing 320b. Also, sliding ball-joint 301a enables the bone anchor 350a implanted in vertebra 192a to slide, pivot and rotate relative to housing 320a. The kinematics of both sliding ball-joints 301a and 301b are substantially as described in FIGS. 1E-1G and accompanying text. This embodiment of a spinal prosthesis 304 is suitable for use for example, where vertebrae 192a, 192b and 192c are not to be fused together. The spinal prosthesis is adapted to provide load-sharing while allowing motion thereby stabilizing a level of the spine 190 while restoring and/or preserving some natural motion of the vertebrae 192a, 192b, 192c. This configuration can, in some embodiments, be utilized to prevent adjacent segment deterioration by supporting a spinal motion segment adjacent a spinal fusion.

Figure 3H:
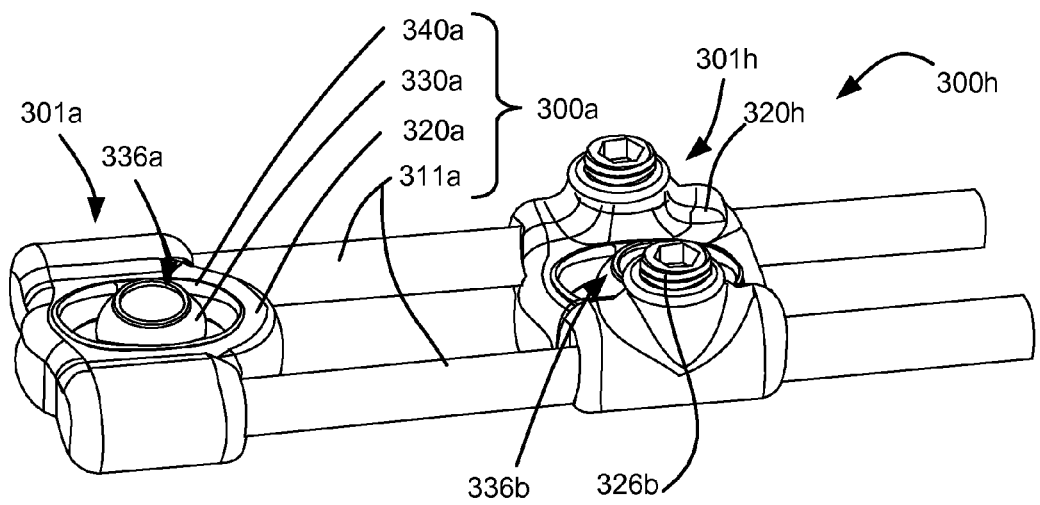
FIG. 3H is a perspective view of an alternative single-level adaptive spinal rod according to an embodiment of the present invention.

FIG. 3H shows an alternative single level adaptive spinal rod 300h. Adaptive spinal rod has almost all components in common with adaptive spinal rod 300 of FIGS. 3A-3F. Adaptive spinal rod 300h includes all of first segment 300a of FIGS. 3A-3C. Adaptive spinal rod 300h includes most of second segment 300b of FIG. 3D. However, in second segment 300b, rod 310b and housing 320b are replaced with a housing 320h which does not include a rod for attachment to a conventional spinal screw on an adjacent level. Adaptive spinal rod 300h is suitable for mounting to bone anchors 350a, 350b (of the same design as bone anchor 350 of FIG. 3E) implanted in adjacent vertebrae. The spacing between housing 320h and housing 320a is adjustable as previously described. After locking the spacing of housing 320h and housing 320a, the sliding ball joints 301a, 301h enable each of the bone anchors 350 to slide, pivot and rotate relative to housings 320a, 320b and rods 311a. The kinematics of both sliding ball-joints 301a and 301h are substantially as described in FIGS. 1E-1G and accompanying text.

Figure 4A:
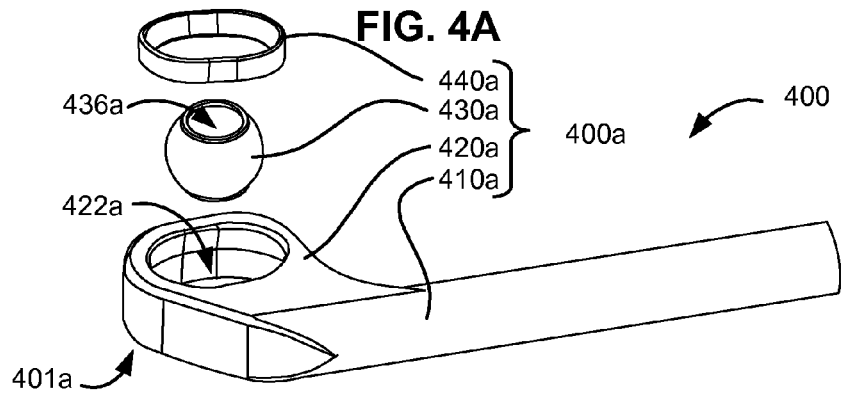
FIG. 4A is an exploded view of a first segment of a two-level adaptive spinal rod according to an embodiment of the present invention.
Figure 4B:
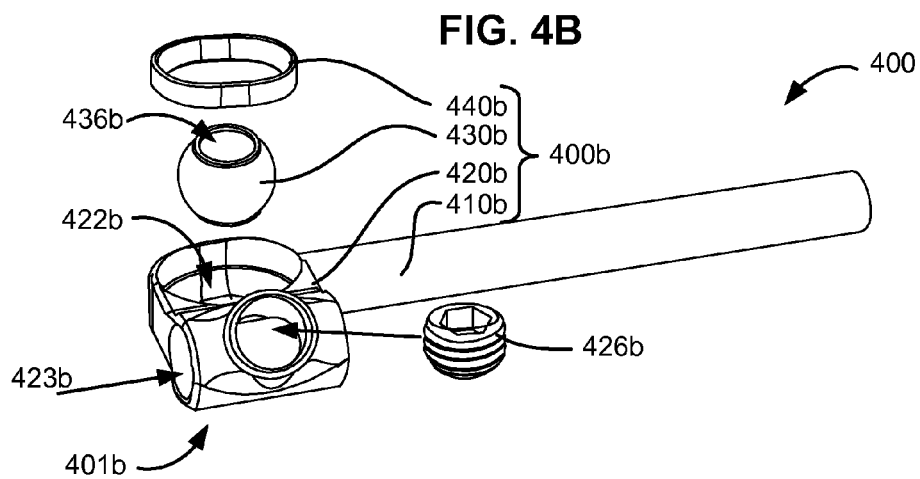
FIG. 4B is an exploded view of a second segment of a two-level adaptive spinal rod according to an embodiment of the present invention.
Figure 4C:
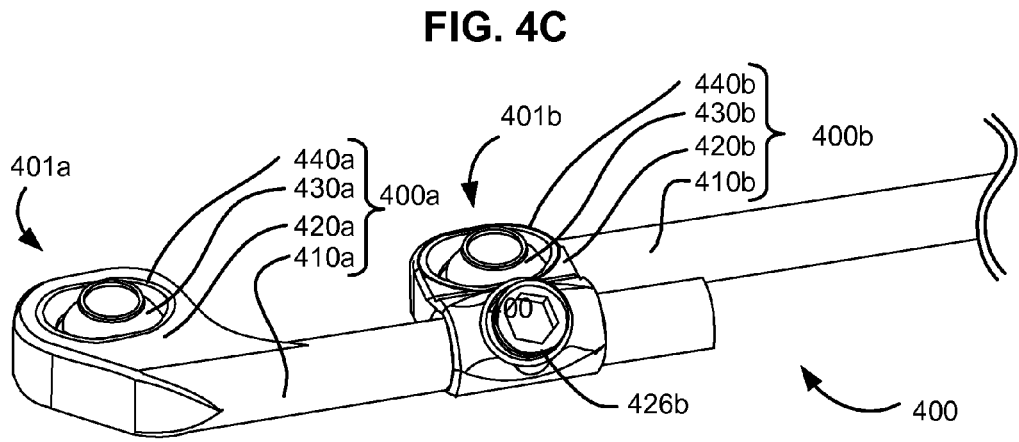
FIG. 4C is a perspective view of an adaptive spinal rod including the components of FIGS. 4A and 4B according to an embodiment of the present invention.

FIGS. 4A-4C show views of an alternative two-level adaptive stabilization rod according to an embodiment of the present invention. FIG. 4A shows an exploded view of first segment and components. FIG. 4B shows an exploded view of the second segment. FIG. 4C shows a perspective view of an assembly including both segments of the two-level adaptive spinal rod of FIGS. 4A-4B.

Referring first to FIG. 4A, which is an exploded view of the components of the first segment 400a of an adaptive spinal rod 400. First segment 400a includes rod 410a, housing 420a, ball 430a and cap 440a. Rod 410a is connected to one side of housing 420a. Rod 410a is similar in shape and material to standard spinal rods. Rod 410a is adapted for mounting to the second segment 400b (See FIG. 4B) of adaptive spinal rod 400 (See FIG. 4C). Rod 410a is, in a preferred embodiment, a cylinder about 5 mm to 6.5 mm in diameter and from 45 mm to 100 mm in length. Housing 420a is preferably in the form of a flattened disc having a lateral extension from which rod 410a protrudes. Housing 420a has a slot 422a passing there through (similar in design in function to slot 122 of FIG. 1A). Slot 422a is shaped to receive ball 430a. The long axis of slot 422 is parallel to the long axis of rod 410a. Cap 440a is adapted to fit within slot 422a of housing 420a. Cap 440a has a cap slot 442a there through (see, e.g. cap 140 of FIG. 1A). Ball 430a is of the same configuration as previously described with respect to FIG. 3B.

During assembly, ball 430a is placed into slot 422a of housing 420a. Cap 440a is then secured into slot 422a of housing 420a trapping or containing ball 430a between cap 440a and housing 420a. Slot 422a of housing 420a and slot 442a of cap 440a cooperate to from a linear race 402a in which ball 430a is trapped or contained. Although ball 430a is trapped within race 402a, ball 430a can pivot and rotate within race 402a. In combination, the surface of ball 430a, and the linear race 402a form a sliding ball-joint 401a. It is to be understood that slot 422a and thus race 402a can be linear and also can be configured in accordance with the various configurations of slot 122 and linear race 102 shown in the embodiments of FIGS. 1A-1H. Aperture 436a of ball 430a is accessible and configured for mounting adaptive spinal rod 400 to a threaded shaft of a pedicle screw such as shown in FIG. 3E.

FIG. 4B shows an exploded view of the second segment 400b of an adaptive spinal rod 400. Second segment 400b includes rod 410b, housing 420b, ball 430b and cap 440b. Rod 410b is connected to the middle of housing 420b. Rod 410b is similar in shape and material to a standard spinal rod. Rod 410b is adapted for mounting to a standard spinal screw/pedicle screw. Rod 410b is, in preferred embodiments, a cylinder about 5 mm to 6.5 mm in diameter and from 45 mm to 150 mm in length. Housing 420b is preferably in the form of a flattened disc. On one side of housing 420b is a bore 423b. Bore 423b runs parallel to rod 410b and passes through housing 420b. Bore 423b is configured to receive rod 410a of first segment 400a (see FIG. 4A) in a sliding fashion. Bore 423b intersects with a threaded bore 424b. A set screw 426b is provided for threaded bore 424b. The set screw 426b when driven in threaded bores 424b is adapted to intersect bore 423b and engage and lock rod 410a of first segment 400a (see FIG. 4A).

FIG. 4C shows two-level adaptive spinal rod 400 fully assembled. Ball 430a, slot 422a and cap 440a have been assembled to create sliding ball-joint 401a. Ball 430b, slot 422b and cap 440b have been assembled to create sliding ball-joint 401b which is similar in design and function to sliding ball-joint 401a. Rod 410a of first segment 400a passes through bore 423b of housing 420b of second segment 400b. The distance between first housing 420a and second housing 420b can be adjusted as suitable for the functional and anatomic needs of the patient. Set screw 426b is subsequently tightened thereby locking rod 410b to housing 420b and fixing the distance between housing 420a and housing 420b.

Figure 4D:
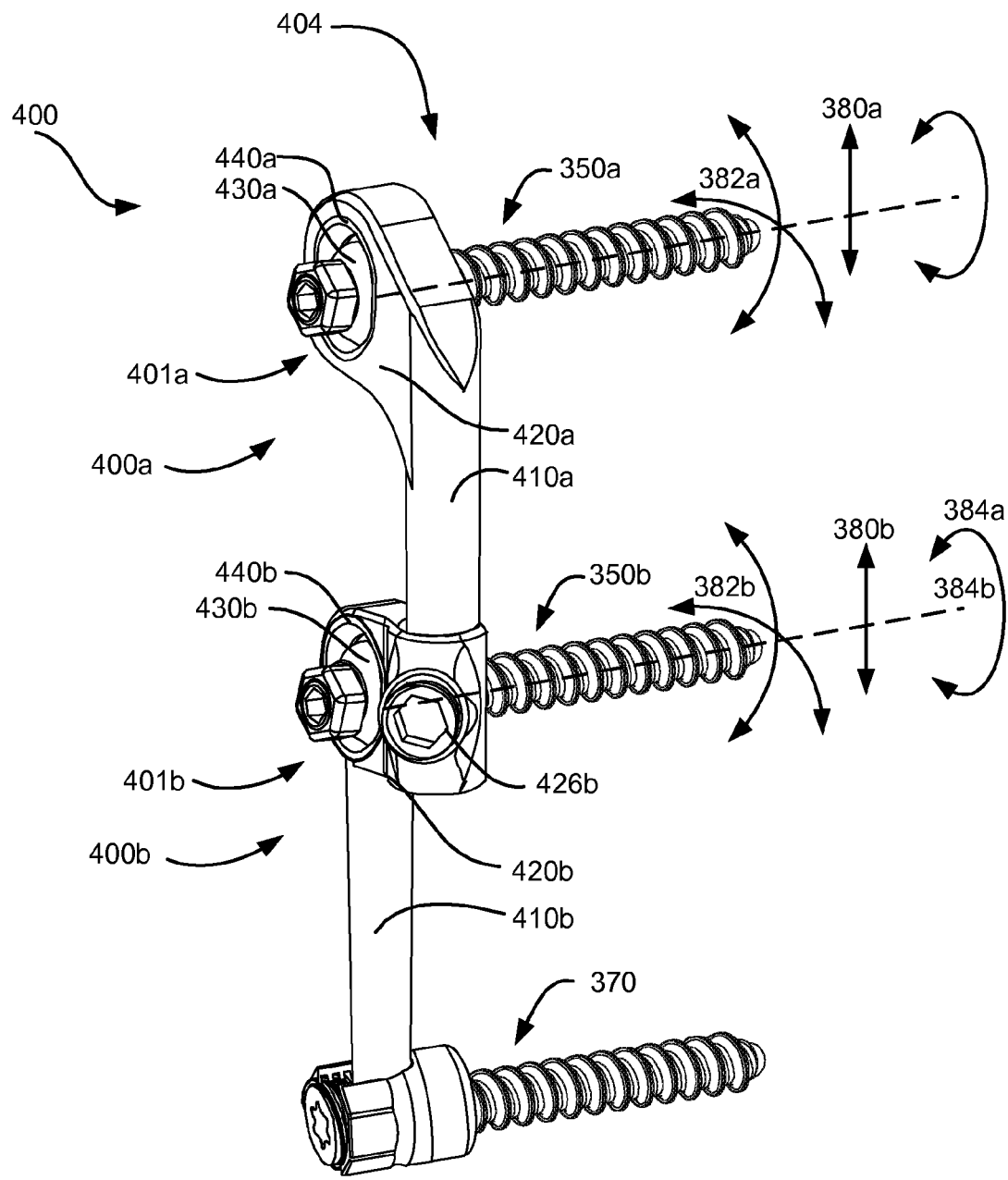
FIG. 4D is a perspective view of an adaptive spinal prosthesis including the two-level adaptive spinal rod of FIGS. 4A-4C according to an embodiment of the present invention.

FIG. 4D shows an example of a two-level spinal prosthesis incorporating two-level adaptive spinal rod 400. Adaptive spinal rod 400 is used, in some embodiments, in combination with two bone anchors 350a, 350b as shown in FIG. 3E and a conventional pedicle screw 370 to create an adaptive spinal prosthesis 404 similar to the adaptive spinal prosthesis shown in FIG. 3F. The first segment 400a of the adaptive spinal rod 400 is mounted by a bone anchor 350 to a first vertebra (not shown). The second segment 400b of the adaptive spinal rod 400 is mounted by a bone anchor 350b to an adjacent vertebra (not shown). The rod 410b of second segment 400b is secured to a third vertebra using a conventional pedicle screw 370. After implantation and assembly, rod 410b housing 420b, rod 410a and housing 420a are all held in substantially fixed relationship to the third vertebra. However sliding ball-joints 401a and 401b permit the bone anchors 350a, 350b to which they are connected to slide (arrows 380a, 380b), pivot (arrows 382a, 382b) and rotate (arrows 384a, 384b) independently of one another. The kinematics of both sliding ball-joints 401a and 401b are substantially as described in FIGS. 1E-1G and accompanying text. The spinal prosthesis is adapted to provide load-sharing while allowing motion thereby stabilizing a level of the spine 190 while restoring and/or preserving some natural motion of the vertebrae.

Figure 5A:
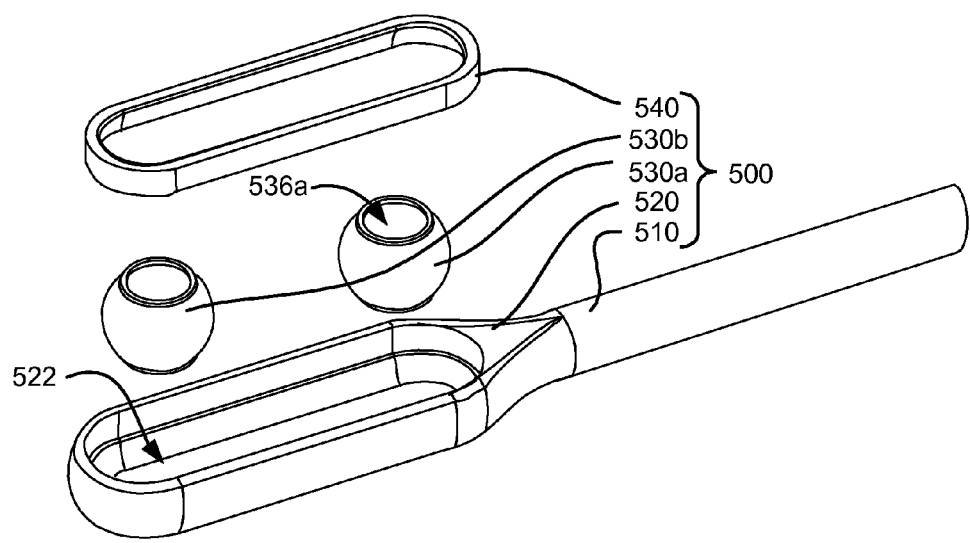
FIG. 5A is an exploded view of a two-level adaptive spinal rod according to an alternative embodiment of the present invention.
Figure 5B:
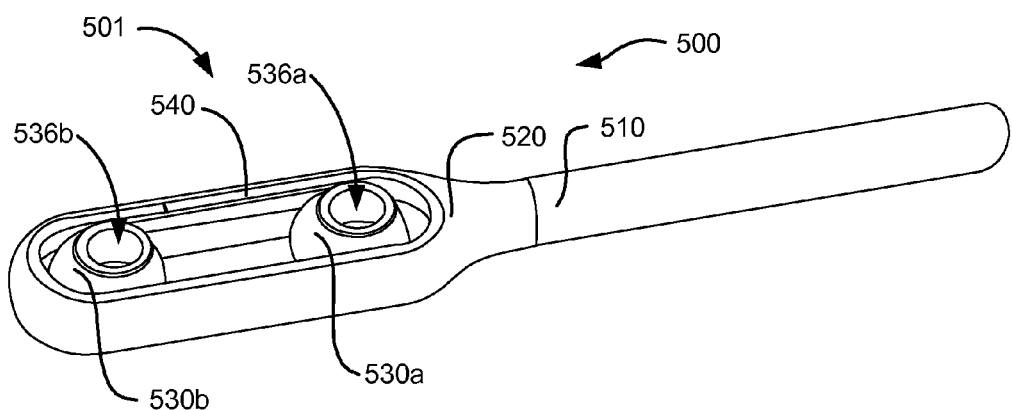
FIG. 5B is a perspective view of an adaptive spinal rod including the components of FIG. 5A according to an embodiment of the present invention.

FIGS. 5A-5B show views of an alternative two-level adaptive spinal rod according to an embodiment of the present invention. FIG. 5A shows an exploded view of the two-level adaptive stabilization system. FIG. 5B shows a perspective view of the assembled two-level adaptive spinal rod of FIG. 5A according to an embodiment of the present invention.

Referring first to FIG. 5A, which is an exploded view of the components of an adaptive spinal rod 500. Adaptive spinal rod 500 includes rod 510, housing 520, ball 530a, ball 530b, and cap 540. Rod 510 is connected to the end of housing 520. Rod 510 is similar in shape and material to standard spinal rods. Rod 510 is adapted for mounting to a conventional spinal screw. Rod 510 is, in a preferred embodiment, a cylinder about 5 mm to 6.5 mm in diameter and from 55 mm to 100 mm in length. Housing 520 is preferably in the form of an elongated flattened disc. Housing 520 has a slot 522 passing there through similar in design in function, but substantially longer than slot 122 of FIG. 1A. In embodiments slot 522 is between 30 mm and 120 mm in length. Slot 522 is shaped to receive both balls 530a and 530b. The long axis of slot 522 is parallel to the long axis of rod 510. Cap 540 is adapted to fit within slot 522 of housing 520. Cap 540 has a cap slot 542 there through. Balls 530a and 530b are of the same configuration as previously described with respect to FIG. 3B.

During assembly, balls 530a and 530b are placed into slot 522 of housing 520. Cap 540 is then secured into slot 522 of housing 520 trapping or containing balls 530a and 530b between cap 540 and housing 520. Slot 522 of housing 520 and slot 542 of cap 540 cooperate to form an elongated race 502 in which balls 530a and 530b are both trapped or contained. Although balls 530a and 530b are trapped within race 502, balls 530a and 530b can pivot and rotate within race 502. In combination, the surface of balls 530a and 530b, and the linear race 502 form an extended sliding ball-joint 501. It is to be understood that slot 522 and thus race 502 can be linear and also can be configured in accordance with the various configurations of slot 122 and linear race 102 shown in the embodiments of FIGS. 1A-1H. Bone anchors 350a, 350b are secured to balls 530a and 530b are accessible and configured for mounting adaptive spinal rod 500 to the threaded shafts of two pedicle screws such as shown in FIG. 3E. FIG. 5B shows two-level adaptive spinal rod 500 fully assembled. Balls 530a, 530b, slot 522 and cap 540 have been assembled to create sliding ball-joint 501. The distance between balls 530a and 530b can be adjusted as suitable for the functional and anatomic needs of the patient.

FIGS. 5C, 5D and 5E show how bone anchors 350a, 350b are able to move with respect to rod 510 of two-level adaptive spinal rod 500 when assembled as a two-level adaptive spinal prosthesis 504. FIG. 5C shows a section through bone anchor 350 and adaptive spinal rod 500 in a substantially saggital plane. FIG. 5D shows a section through bone anchor 350 and adaptive spinal rod 500 in a transverse plane. FIG. 5E shows a section through bone anchor 350 and adaptive spinal rod 500 in a substantially dorsal plane through the middle of the housing 520.

As shown in FIG. 5C, two-level adaptive spinal rod 500 can be used in combination with two bone anchors 350a, 350b (as described with respect to FIG. 3E) and a conventional spinal screw 170 (as, for example described with respect to FIG. 1D) to create an adaptive spinal prosthesis 504 similar to the adaptive spinal prosthesis shown in FIG. 3F. The first ball 530a of the adaptive spinal rod 500 is mounted by a bone anchor 350a to a first vertebra (not shown). The second ball 530b of the adaptive spinal rod 500 is mounted by another bone anchor 350b to an adjacent vertebra (not shown). The rod 510 of the adaptive spinal rod 500 is secured to a third vertebra (not shown) using a conventional spinal screw 170. After implantation and assembly, rod 510 and housing 520b are held in a substantially fixed relationship to the third vertebra. However the motion of balls 530a and 530b within sliding ball-joint 501 permits the bone anchors to which they are connected to slide, pivot and rotate.

Referring again to FIG. 5C which shows a section through an adaptive spinal prosthesis 504 in a substantially saggital plane (vertical and including the longitudinal axis of bone anchors 350a, 350b). As shown in FIG. 5C, balls 530a, 530b are trapped or contained in linear race 502 formed by cap 540 in conjunction with housing 520. Balls 530a, 530b can move within race 502. Bone anchors 350a, 350b are mounted to balls 530a, 530b and thus can move relative to rod 510 with one angular degree of freedom and one linear degree of freedom shown in this view.

In the saggital plane shown in FIG. 5C, the linear motion of balls 530a, 530b within race 502 allows bone anchors 350a, 350b a limited vertical range of movement (shown by arrows 580) equal to the linear travel of balls 530a, 530b within race 502. The range of vertical motion is limited by the length of linear race 502. The desired range of vertical motion 580, and thus the length of the race 502, is selected based upon the anatomical and functional needs of a patient. In this embodiment, however, linear race 502 is sufficiently long to span between vertebrae. Thus, although the maximum distance between balls 530a, 530b is constrained, balls 530a and 530b are relatively unconstrained in movement towards one another.

In the saggital plane shown in FIG. 5C, the pivoting of balls 530a, 530b within race 502 also allows each of bone anchors 350a, 350b a independent and limited angular range of movement which corresponds to spinal flexion/extension (shown by arrows 582). The center of balls 530a, 530b is the center of rotation. The range of angular motion 582 is limited by interference between one or more of balls 530a, 530b and bone anchor 350 with housing 520. The desired range of angular motion 582, and thus the shape of balls 530a, 530b, bone anchor 350 and housing 520, is selected based upon the anatomical and functional needs of a patient.

Referring next to FIG. 5D which shows a section through bone anchor 350a and adaptive spinal rod 500 in a substantially transverse plane (horizontal and including the longitudinal axis of bone anchor 350a). The kinematics of bone anchor 350b are substantially similar to that of bone anchor 350a. As shown in FIG. 5D, ball 530a is trapped or contained in linear race 502 formed by cap 540 in conjunction with housing 520. Ball 530a can move within race 502. Rod 510 is oriented either directly into or directly out of the page in this transverse view through housing 520. Bone anchor 350a is mounted to balls 530a and thus can move relative to housing 520 with one angular degree of freedom shown in this view.

In the transverse plane shown in FIG. 5D, the pivoting of ball 530a within race 502 allows bone anchor 350a a limited angular range of movement which corresponds to spinal rotation (shown by arrow 584). The center of ball 530a is the center of rotation. The range of angular motion is limited by interference between one or more of ball 530a and bone anchor 350 with housing 520. The desired range of angular motion 584, and thus the shape of ball 530a, bone anchor 350 and housing 520, is selected based upon the anatomical and functional needs of a patient. In embodiments, the range of angular movement 584 in the transverse plane is limited to less than 20 degrees.

Referring next to FIG. 5E which shows a section through bone anchor 350a and adaptive spinal rod 500 in a substantially dorsal plane (vertical and perpendicular to the longitudinal axis of bone anchors 350a, 350b). As shown in FIG. 5E, balls 530a, 530b are trapped or contained in linear race 502. Balls 530a, 530b can move within race 502. Bone anchors 350a, 350b are oriented either directly into or directly out of the page in this transverse view through housing 520. Bone anchors 350a, 350b are mounted to balls 530a, 530b and thus can move relative to rod 510 with one angular degree of freedom and one linear degree shown in this view.

In the dorsal plane shown in FIG. 5E, the linear motion of balls 530a, 530b within race 502 allows bone anchors 350a, 350b the limited vertical range of movement (shown by arrows 580) equal to the linear travel of balls 530a, 530b within race 502 as described above. Rotation of balls 530a, 530b within race 502 also allows bone anchors 350a, 350b to rotate freely an independently (360+ degrees) as shown by arrows 586 which corresponds to lateral spinal twisting. The bone anchors 350a, 350b and balls 530a, 530b rotate freely around the longitudinal axis of the bone anchors. The range of angular motion 586 is not limited in this embodiment. However features to limit such rotation could be designed into one or more of balls 530a, 530b and bone anchors 350a, 350b and housing 520. The desired range of angular motion 586, and thus the shape of balls 530a, 530b, bone anchors 350a, 350b and housing 520, can be selected, if necessary) based upon the anatomical and functional needs of a patient.

Figure 5F:
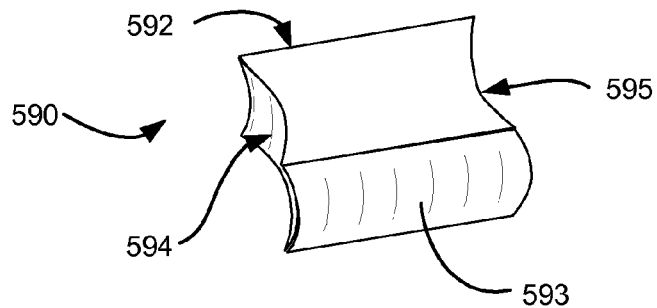
FIG. 5F shows a spacer which is, in some embodiments, incorporated into the two-level adaptive spinal rod of FIG. 5B.
Figure 5G:
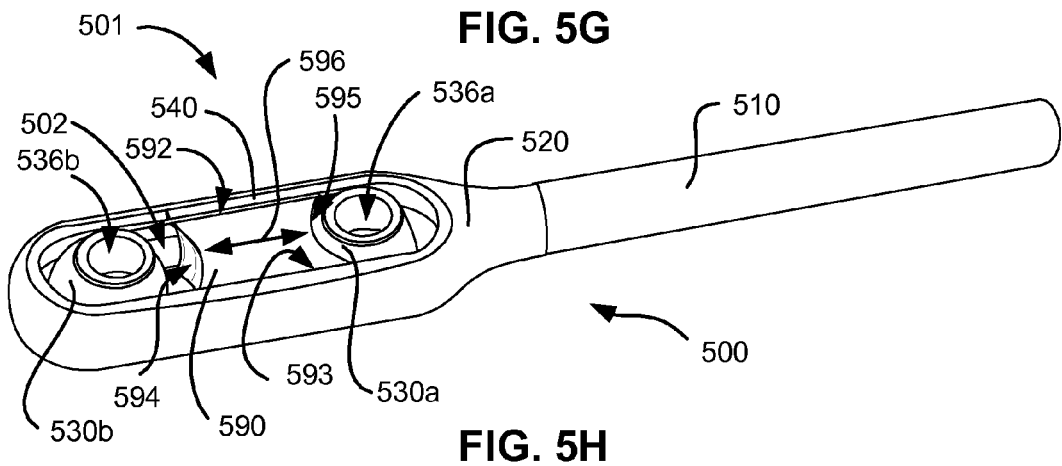
FIG. 5G is a perspective view of an adaptive spinal rod including the components of FIGS. 5A through 5E according to an alternative embodiment of the present invention.
Figure 5H:
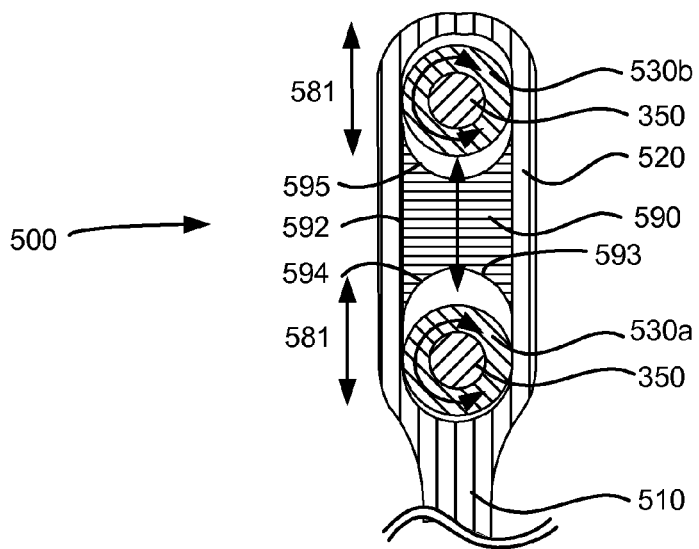
FIG. 5H is a dorsal section of a two-level adaptive spinal prosthesis incorporating the adaptive spinal rod of FIG. 5G.

FIGS. 5F, 5G and 5H relate to a modification to the two-level adaptive spinal rod of FIGS. 5A-5E incorporating a spacer. FIG. 5F is a perspective view the spacer. FIG. 5G shows the spacer in combination with the two-level adaptive spinal rod of FIGS. 5A-5E. FIG. 5H shows a sectional view through the modified adaptive spinal rod.

Referring first to FIG. 5F which is a perspective view of a spacer 590. As shown in FIG. 5F, spacer 590 has two parallel sides 592, 593. Parallel side 592, 593 are convex. The curvature of sides 592, 593 is selected to engage the curvature of the linear race 502. Sides 592, 593 are spaced such that spacer 590 can fit within linear race 502 and slide along linear race 502. Spacer 590 is, in some embodiments, made from a biocompatible metal, for example, titanium, titanium alloy and/or cobalt chrome. The other two sides 594, 595 of spacer 590 are concave. The surface of sides 594, 595 is selected to engage the surfaces of balls 530a, 530b. The thickness of spacer 590 is substantially the thickness of linear race 502.

Referring to FIG. 5G which shows spacer 590 assembled with the two-level adaptive spinal rod 500 of FIGS. 5A-5E. As shown in FIG. 5G, spacer 590 fits within linear-race 502 between balls 530a and 530b. Convex sides 592, 593 of spacer 590 engage and slide within the sides of linear race 502. Spacer 590 can slide along linear race 502 as shown by arrow 596. The sides 594, 595 are positioned to contact balls 530a, 530b and limit the travel of balls 530a, 530b toward one another. Thus, spacer 590 serves to constrain somewhat the range of motion of balls 530a, 530b and limit extension of the spine.

FIG. 5H shows a section through bone anchors 350a, 350b and adaptive spinal rod 500 including spacer 590 in a substantially dorsal plane (vertical and perpendicular to the longitudinal axis of bone anchors 350a, 350b). As shown in FIG. 5H, balls 530a, 530b are trapped or contained in linear race 502. Spacer 590 is positioned between balls 530, 530b Balls 530a, 530b can move within race 502. In the dorsal plane shown in FIG. 5E, the linear motion of balls 530a, 530b within race 502 allows bone anchors 350a, 350b the limited vertical range of movement shown by arrows 581 equal to the linear travel of balls 530a, 530b within race 502 but constrained by the presence of spacer 590. Note that the range of motion 581 is reduced compared to range of motion 580 of FIG. 5E because of the presence of spacer 590. The range of linear motion 181 is limited by interference between one or more of ball 350a, ball 350b, and spacer 590 with housing 520. The desired range of angular motion 581, and thus the shape of balls 530a, 530b, spacer 590 and housing 520, is selected based upon the anatomical and functional needs of a patient. In embodiments, the range of linear movement is limited to less than 10 mm. In preferred embodiments, the range of linear movement 581 is limited to less than 4 mm.

Rotation of balls 530a, 530b within race 502 still allows bone anchors 350a, 350b to rotate freely an independently (360+ degrees) as shown by arrows 586 which corresponds to lateral spinal twisting. The desired range of angular motion 586, and thus the shape of balls 530a, 530b, bone anchors 350a, 350b and housing 520, can be selected, if necessary) based upon the anatomical and functional needs of a patient.

Figure 6E:
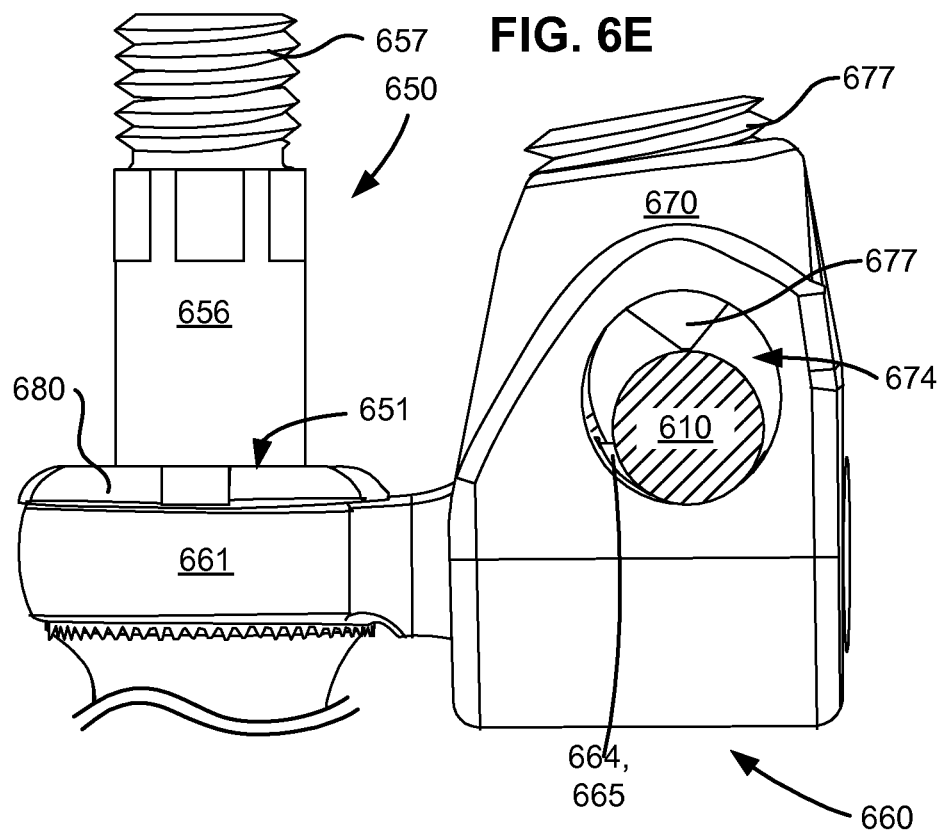
FIGS. 6E and 6F are views illustrating the clamping action of the polyaxial connector of FIG. 6C.
Figure 6F:
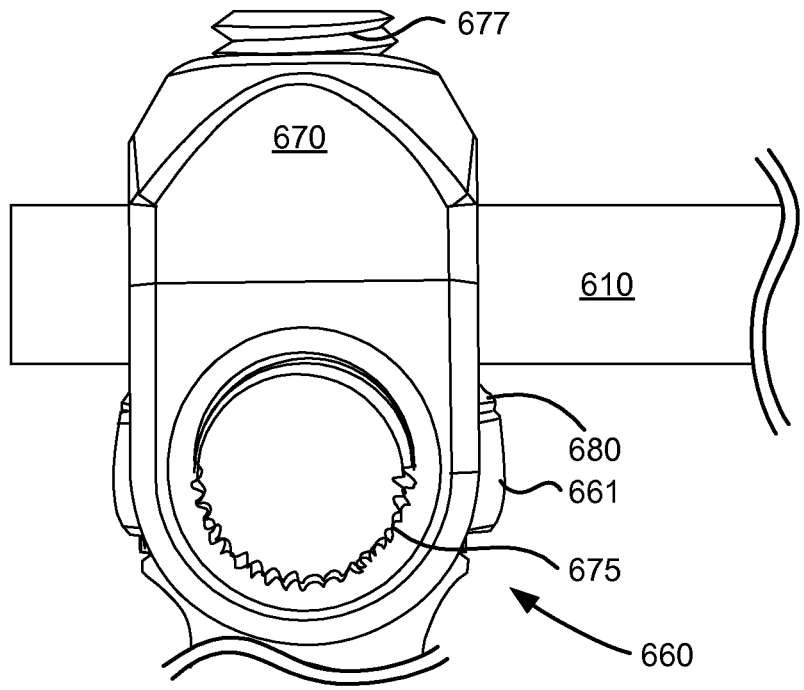
Figure 6G:
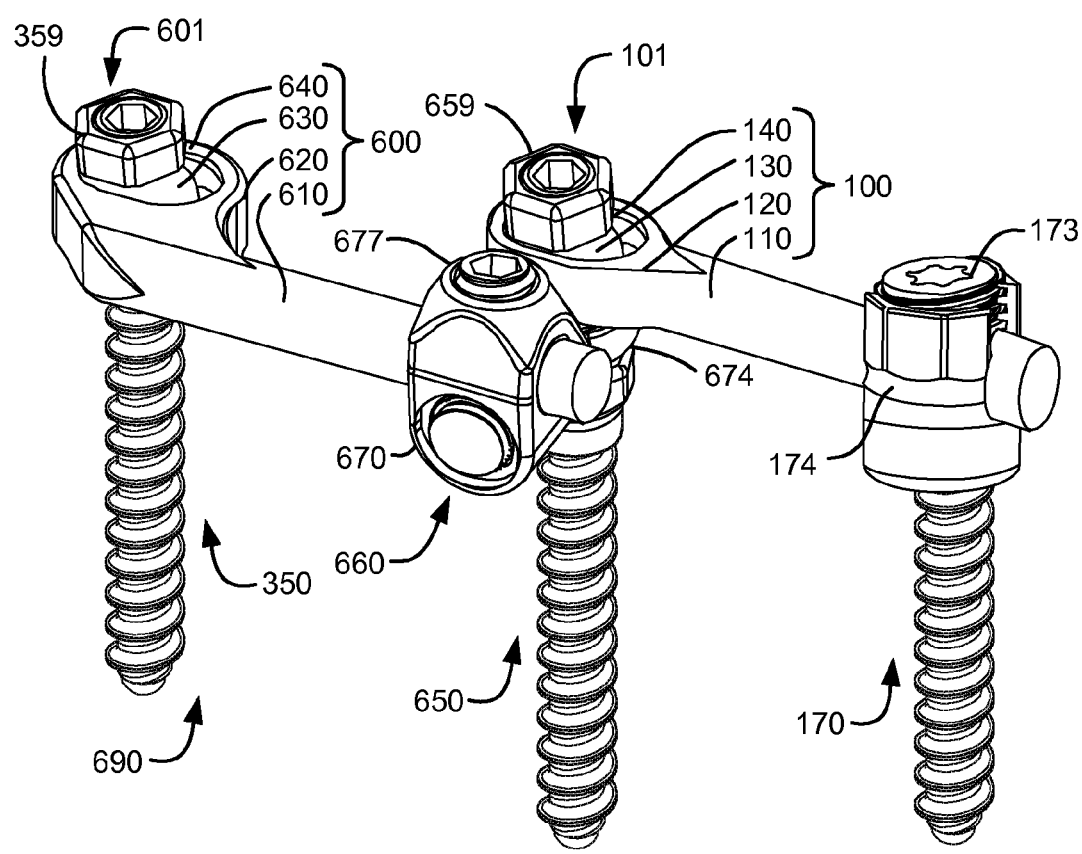
FIG. 6G is a perspective view illustrating a two-level adaptive spinal prosthesis utilizing the components of FIGS. 6A-6D.

In alternative embodiments, single-level adaptive spinal rods are connected using one or more connectors to assemble a multi-level adaptive spinal prosthesis. A range of polyaxial connectors adaptable for this purpose is disclosed in U.S. patent application Ser. No. 12/566,485 titled "Versatile Polyaxial Connector Assembly And Method For Dynamic Stabilization Of The Spine" to Mitchell et al. FIGS. 6A-6G show views of a polyaxial connector 660, suitable for use with bone anchor 650 and adaptive spinal rod 600 as part of a multi-level adaptive spinal prosthesis (see FIG. 6G). Connector 660 mounts externally to a second mount of a bone anchor 650. FIG. 6A shows an example of an adaptive spinal rod 600. FIG. 6B shows a two-mount bone anchor 650 suitable for use with adaptive spinal rod 600 and connector 66. FIG. 6C shows an exploded view of a connector 660, and components thereof. FIG. 6D shows a perspective view of connector 660 as assembled. FIGS. 6E and 6F illustrate operation of the connector 660. FIG. 6G shows a two-level adaptive spinal prosthesis using the components of FIGS. 6A-6F.

Referring first to FIG. 6A, which shows a single level adaptive spinal rod 600. Adaptive spinal rod 600 includes rod 610, housing 620, arm 621, ball 630 (see e.g. ball 330 of FIG. 3B) and cap 640. Rod 610 is connected to one side of housing 620. Rod 610 is similar in shape and material to standard spinal rods. Rod 610 is adapted for mounting to a connector or spinal screw (not shown). Rod 610 is, in a preferred embodiment, a cylinder about 5 mm to 6.5 mm in diameter and from 65 mm to 100 mm in length. An arm 621 projects laterally from housing 620 and connects to rod 610.

Housing 620 is preferably in the form of a flattened disc. Housing 620 has a slot 622 passing therethrough (similar in design in function to slot 122 of FIG. 1A). Slot 622 is shaped to receive ball 630. The long axis of slot 622 is parallel to the long axis of rod 610. Cap 640 is adapted to fit within slot 622 of housing 620. As shown in FIG. 6A, cap 640 and housing 620 cooperate to form race 602 in which ball 630 is trapped to form a linear ball-joint as previous described. Although ball 630 is trapped within race 602, ball 630 can pivot and rotate within race 602. It is to be understood that slot 622 and thus race 602 can be linear and also can be configured in accordance with the various configurations of slot 122 and linear race 102 shown in the various embodiments of FIGS. 1A-1H. Aperture 636 of ball 630 is accessible and configured for mounting adaptive spinal rod 600 to a bone anchor (see, e.g., FIG. 6B).

FIG. 6B, shows a bone anchor 650 configured for attachment of adaptive spinal rod 600 to a vertebra through a connector (not shown). As shown in FIG. 6B, bone anchor 650 includes a threaded shaft 652 at the distal end. Threaded shaft 652 is sized and configured for engaging a vertebra. In preferred embodiments threaded shaft 652 is sized and configured for implantation in the pedicle of a vertebra. Attached to threaded shaft 652 is head 654. Head 654 includes splines 655 which permit head to engage a connector in a fixed angular position. Protruding proximally from head 654 is a second mount 651. Second mount 651 is designed to be received in and engaged by connector 660 of FIGS. 6C and 6D. Second mount 651 is threaded in order that the connector can be secured to second mount Protruding proximally from second mount 651 is first mount 656. First mount 656 has a smooth exterior surface to receive ball 630 of FIG. 6A. Protruding proximally of first mount 656 is a threaded shaft 657 for attaching a nut 659 to secure ball 630 of FIG. 6A. In the proximal end of threaded shaft 657 is an aperture 658. Aperture 658 is shaped such that the aperture 658 can be engaged by a driver for implanting/removing bone anchor 650 and/or attaching nut 659. For example, aperture 658 has, in some embodiments, a hexagonal or octagonal cross-section.

Referring next to FIGS. 6C and 6D, which show respectively an exploded and assembled view of connector 660. The components of connector 660 include: snap ring 662, set screw 677, clamp ring 661, swivel 670 and ring nut 680. As shown in FIG. 6C, clamp ring 661 is generally annular with a bore 669. Bore 669 of clamp ring 661 is sized such that the clamp ring 661 can slide over second mount 651 of bone anchor 650 and also receive the distal end 682 of ring nut 680. Clamp ring 661 can rotate around the second mount 651 before the clamp ring 661 is locked in place by ring nut 680. Clamp ring 661 has a plurality of splines 667 on a distal surface for engaging splines 655 of bone anchor 650. Clamp ring 661 has a cylindrical extension 664. Cylindrical extension 664 includes a saddle 665 and terminal groove 668. The groove 668 is sized to engage snap ring 662.

Swivel 670 has a channel 674 which passes through swivel 670 and which is sized to receive therethrough the rod of an adaptive spinal rod (or conventional spinal rod). Swivel 670 has a threaded aperture 678 sized to fit set screw 677. Threaded aperture 678 intersects channel 674 to allow set screw 677 to contact a spinal rod (not shown) within channel 674. A bore 671 passes through swivel 670 and intersects with channel 674. Bore 671 is sized to receive cylindrical extension 664 of clamp ring 661. Bore 671 has a lip 672 sized to engage snap ring 662. Snap ring 662 is designed to fit engage groove 668 of cylindrical extension 664 and lip 672 of bore 671 to secure cylindrical extension 664 within bore 671. Cylindrical extension 664 can, however, rotate within bore 671.

As shown in FIG. 6D, ring nut 680 is received within bore 669 of clamp ring 661. Ring nut 680 is, in some embodiments, provided with a lip, groove, or other detent (not shown) to hold ring nut 680 within bore 669 while still allowing rotation of ring nut 680 relative to clamp ring 661. Ring nut 680 also has tool engagement features 684 which can be engaged by a tool/wrench to secure ring nut 680 to second mount 651 of bone anchor 650 (see FIG. 6B). Cylindrical extension 664 is received through bore 671 and held in place by snap ring 662. Set screw 672 is received within threaded aperture 678 of swivel 670.

FIGS. 6E and 6F illustrate the mounting of connector 660 to rod 610 and to the second mount 651 of bone anchor 650. As shown in FIG. 6E, rod 610 (shown in section) is received in channel 674 of connector 660. Second mount 651 is received in clamp ring 661. During implantation, clamp ring 661 can rotate around bone anchor 650. The unclamped configuration allows adjustment of the direction of rod 610 and also allows rod 610 to slide through channel 674, and also allows swivel 670 to rotate around cylindrical extension 664.

When ring nut 680 is tightened, splines 655 are forced against splines 667 locking clamp ring 661 to second mount 651 and preventing further rotation around bone anchor 650. When set screw 677 is tightened, it forces rod 610 against saddle 665, locking rod 610 in position. Set screw 677 also forces splines of cylindrical extension 664 against splines 675 of swivel 670 locking swivel 670 in position relative to clamp ring 661. Operation of the ring nut 680 and set screw 677 serves to place the connector 660 in a clamped configuration and lock the clamp ring 661 to the second mount 651 of the bone anchor 650, lock swivel 670 in a fixed position relative to clamp ring 661 and secure rod 610 within the channel 674 of connector 660.

The connector 660 of FIGS. 6C-6F may be used, in some embodiments, to construct an adaptive stabilization assembly for one or more levels of the spine of a patient. FIG. 6G shows an example of a two-level adaptive stabilization assembly 690 utilizing the connector 660 of FIGS. 6C-6F. FIG. 6G shows how the components may be assembled to provide a multi-level adaptive stabilization assembly which provides stabilization of the spine and load sharing while preserving motion. Note that an identical or similar construct would preferably be implanted on each side of the spine.

As shown in FIG. 6G, rod 110 of adaptive spinal rod 100 is mounted to head 174 of spinal screw 170. Ball 130 of adaptive spinal rod 100 is secured to bone anchor 650 by nut 659. Sliding ball-joint 101 permits bone anchor 650 to slide, pivot and rotate relative to spinal screw 170. Connector 660 is also mounted to bone anchor 650. Ring nut 680 (not shown) secures clamp ring 661 of connector 660 to bone anchor 650. Set screw 677 secures rod 610 of adaptive spinal rod 600 within channel 674 of swivel 670. Ball 630 of adaptive spinal rod 600 is secured to bone anchor 350 by nut 359. Sliding ball-joint 601 permits bone anchor 650 to slide pivot and rotate relative to bone anchor 350.

As also shown in FIG. 6G, ball 630 of adaptive spinal rod 600 is secured to bone anchor 350 by nut 359. Rod 110 is positioned within channel 674 of connector 660. The position of the rod 610 is then adjusted relative to connector 660 prior to tightening set screw 677. Adaptive stabilization assembly 690 spans two vertebrae two levels of the spine (three vertebrae). Connector 660 and adaptive spinal rods 100, 600 permit assembly of adaptive stabilization assembly 690 for a wide range of different patient anatomies and/or placement of bone anchors 350, 650 and spinal screw 170. Connector 660 is particularly useful where, as here, there is slight lateral displacement between the bone anchor positions on either side of a level.

Adaptive spinal prosthesis 690 is typically assembled in vivo by first implanting the bone anchors 650, 350 and spinal screw 170 in pedicles of adjacent vertebra. After implanting the bone anchors 650, 350 and spinal screw 170, the connector 660 is placed over bone anchor 650 and rod 610 is positioned within channel 674 of the connector 660. Ball 630 is then secured to bone anchor 350. After securing ball 630, the position of rod 610 and swivel 670 are adjusted and then connector 660 is locked in position by tightening set screw 677 and tightening ring nut 680 (not shown). Rod 110 is then secured to head 174 of spinal screw 170 by tightening set screw 173.

Figure 7A:
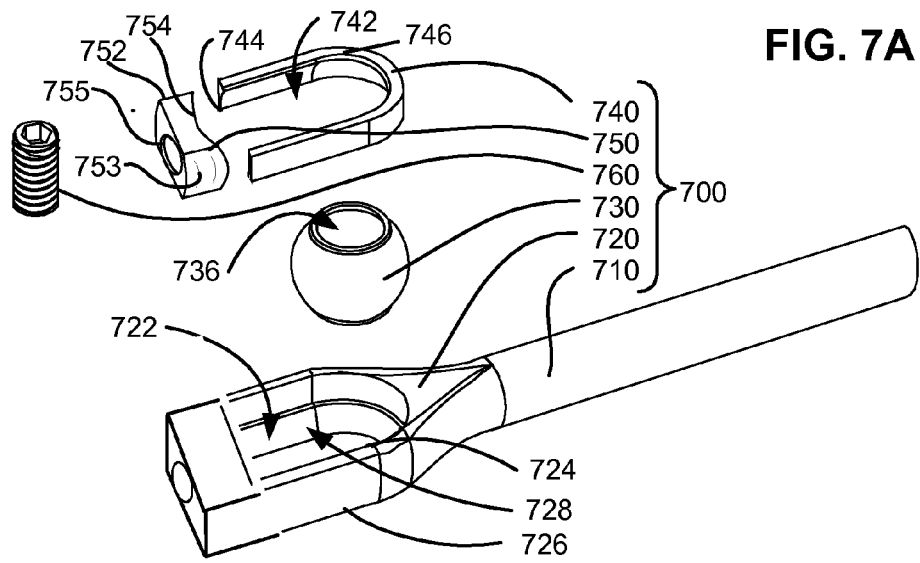
FIG. 7A is an exploded view of an adaptive spinal rod according to an embodiment of the present invention.
Figure 7B:
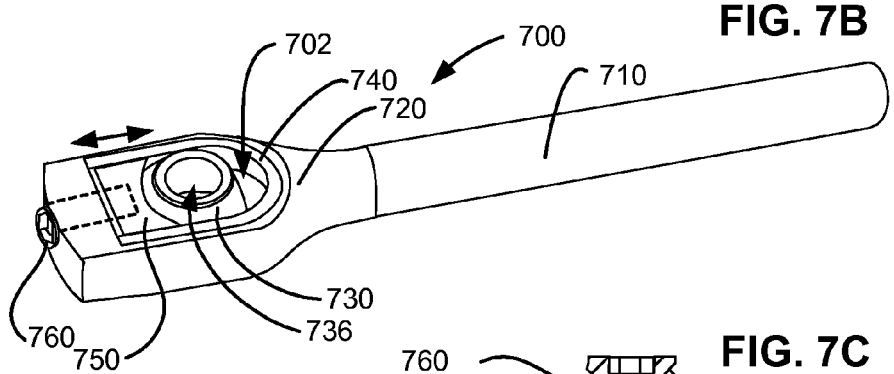
FIG. 7B is a perspective view of the adaptive spinal rod of FIG. 7A.
Figure 7C:
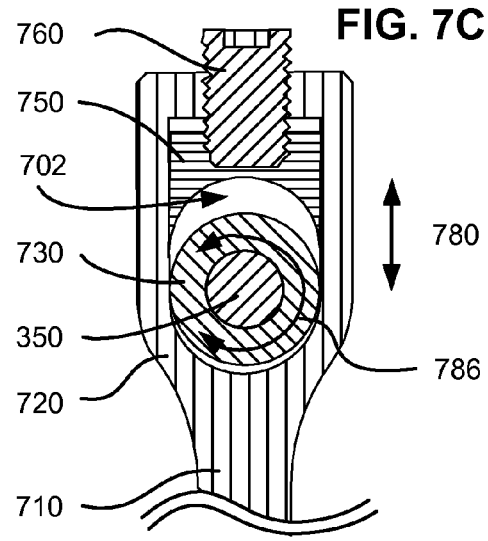
FIG. 7C is a partial sectional view of the adaptive spinal rod of FIG. 7A.

FIGS. 7A-7C are views of an adaptive stabilization system including an adaptive spinal rod according to an alternative embodiment of the present invention. FIG. 7A is an exploded view showing the components of an adaptive spinal rod. FIG. 7B is a perspective view of the assembled adaptive spinal rod. FIG. 7C is a sectional view illustrating the kinematics of a bone anchor relative to the adaptive spinal rod.

Referring first to FIG. 7A, which is an exploded view of the components of an adaptive spinal rod 700. Adaptive spinal rod 700 includes: rod 710, housing 720, ball 730, cap 740, spacer 750 and set screw 760. Rod 710 is connected at one end to housing 720. Rod 710 is similar in size, shape and material to standard spinal rods. Rod 710 is adapted for mounting to a standard pedicle screw or polyaxial screw (not shown). Rod 710 is in preferred embodiments, preferably a cylinder about 5 mm to 6.5 mm in diameter and from 35 mm to 100 mm in length. In preferred embodiments, rod 710 and housing 720 are made in one piece from titanium or titanium alloy.

Housing 720 has a slot 722 passing there through. Slot 722 is shaped to receive ball 730 and spacer 750 from open side 724 however, the closed side 726 of slot 722 is too small for ball 730 and spacer 750 to pass. Open side 724 of slot 722 is also shaped to receive cap 740. Closed side 726 of slot 722 has a curved surface 728 adapted to engage ball 730. In one embodiment curved surface 728 has the same radius of curvature as ball 730. Housing 720 has a threaded aperture 721 for receiving set screw 760.

Ball 730 is in some embodiments, of the same design as ball 130 of FIG. 1A or ball 330a of FIG. 3B. An aperture 736 passes through ball 730. In some embodiments the aperture is threaded in part and/or provided with tool engagement features (a hexagonal depression is shown) which allow ball 730 to be engaged and turned by a tool. Ball 730 is adapted to be secured to a bone anchor with or without using a separate nut depending on design.

Spacer 750 has two parallel sides 752, 753. Parallel side 752, 753 are convex. The curvature of sides 752, 753 is selected to engage the curvature of the linear race 502. Sides 752, 753 are spaced such that spacer 750 can fit within race 702 and slide along linear race 702. As discussed above, race 702 can have other configurations. Spacer 750 is, in some embodiments, made from a biocompatible metal, for example, titanium, titanium alloy and/or cobalt chrome. Side 754 of spacer 750 is concave for engaging ball 730. The remaining has an aperture 755 for engaging set screw 760. The thickness of spacer 750 is substantially the thickness of linear race 702. In alternative embodiments, set screw 760 is adapted to contact ball and directly limit the length of linear race 702 without the need for a spacer 750.

Cap 740 is adapted to fit within slot 722 of housing 720. Cap 740 has a cap slot 742 therethrough. The open side 744 of slot 742 is configured to admit a portion of ball 730 and spacer 750. The closed side 746 of slot 742 is too small for ball 730 and spacer 750 to pass. The interior of slot 742 has a curved surface adapted to engage ball 730 and spacer 750. During assembly, ball 730 and spacer 750 are placed into slot 722 of housing 720. Cap 740 is then secured into slot 722 of housing 720 trapping ball 730 and spacer 750 between cap 740 and housing 720.

FIG. 7B shows a fully assembled adaptive spinal rod 700 in which ball 730 and spacer 750 are positioned between cap 740 and housing 720. The position of spacer 750 is adjustably controlled by set screw 760. Slot 722 of housing 720 and slot 742 of cap 740 cooperate to from a linear race 702 in which ball 730 is contained or trapped. The position of spacer 750 controls the length of linear race 702. Although ball 730 is contained or trapped within linear race 702, ball 730 can pivot and rotate within race 702 as shown by arrows 760, 762. Ball 730 can also slide a small distance along linear race 702 as shown by arrow 764. The range of angular and linear movement of ball 730 can be adjusted by changing the length of linear race 702 using set screw 760 and spacer 750. In adaptive spinal rod 700 as assembled, aperture 736 of ball 730 is accessible and configured for mounting adaptive spinal rod 700 to a bone anchor, e.g. bone anchor 350 of FIG. 3E.

Referring next to FIG. 7C which shows a section through a bone anchor 350 and adaptive spinal rod 700 in a substantially dorsal plane (vertical and perpendicular to the longitudinal axis of bone anchor 350). As shown in FIG. 7C, ball 730 is contained or trapped in linear race 102. Set screw 760 is adjustable to move spacer 750 and control the length of race 702. Ball 730 can move within race 702. Bone anchor 350 is oriented either directly into or directly out of the page in this transverse view through housing 720. Bone anchor 350 is mounted to ball 730 and thus can move relative to rod 710 with one angular degree of freedom and one linear degree shown in this view.

In the dorsal plane shown in FIG. 7C, race 702 allows bone anchor 150 a limited vertical range of movement 780 corresponding to spinal flexion/extension. The range of linear motion can be adjusted using set screw 760 to more spacer 750. Rotation of ball 130 within race 702 is unrestricted, allowing bone anchor 350 to rotate freely (360+ degrees) as shown by arrow 786 which corresponds to lateral spinal twisting. The bone anchor 350 rotates freely around the longitudinal axis of the bone anchor 350. The range of rotation 786 is not limited in this embodiment. However features to limit such rotation could be designed into one or more of bone anchor 750, ball 730, cap 740, and housing 720. The desired range of linear motion 780 and rotation 786, can be selected, if necessary or desirable, based upon the anatomical and functional needs of a patient.

Implantation And Assembly Tools

The implantation and assembly of adaptive spinal rods is preferably performed in a minimally invasive manner and, thus, tools are provided to facilitate installation and assembly through cannulae. These tools can also be used in open procedures. One suitable minimally invasive approach to the lumbar spine is the paraspinal intermuscular approach. This approach is described for example in "The Paraspinal Sacraspinalis-Splitting Approach to the Lumber Spine," by Leon L. Wiltse et al., *The Journal of Bone & Joint Surgery*, Vol. 50-A, No. 5, July 1968, which is incorporated herein by reference. In general the patient is positioned prone. Incisions are made posterior to the vertebrae to be stabilized. The dorsal fascia is opened and the paraspinal muscle is split to expose the facet joints and lateral processes of the vertebra. Bone anchors according to embodiments of the present invention and conventional pedicle screws are placed in the vertebrae as necessary for the selected assembly. The screws are placed lateral to the facet joints and angled in towards the vertebral body.

After placement of the screws, the adaptive spinal rods according to embodiments of the present invention are then inserted into position adjacent the bone anchors, screws and conventional pedicle screws. The balls of the adaptive spinal rods are then secured to the mounts of the bone anchors the other end of the adaptive spinal rod is then connected to the conventional screws with the desired interpediclular distance. The implantation of the adaptive bone anchors and connection of the adaptive rods can be facilitated by specially designed implantation tools (FIGS. 8A-8D) and connection tools (FIGS. 9A-9F) as described below.

FIG. 8A shows a perspective view of an implantation tool 850 for use in implanting a bone anchor 150. Bone anchor 150 is as described with respect to FIG. 1C with the addition of a tool engagement feature (not shown). Implantation tool 850 includes an inner shaft 860 received within a tubular sleeve 870. Inner shaft 860 is free to rotate within sleeve 870. Sleeve 870 may also be slid towards the proximal end of inner shaft 860 by pulling on grip 874. A coil spring 872 is connected between the sleeve 870 and inner shaft 860 to hold sleeve 870 in its more distal position relative to shaft 860. The length and diameter of implantation tool 850 is selected so as to allow use through a cannula in a minimally invasive surgical technique thereby reducing disruption of tissues adjacent the implantation site, reducing patient recovery and improving surgical outcomes.

Referring again to FIG. 8A, shaft 860 has at a proximal end a quick release mount 862 to which a handle (not shown) may be attached for turning inner shaft 860. Suitable handles for attachment to shaft 860 include ratcheting handles, torque sensing handles and torque limiting handles. In alternative embodiments, a handle may be permanently connected to or integrated with the proximal end of shaft 862. Inner shaft has at a distal end a head 864. Head 864 includes means for engaging and securing bone anchor 150 during implantation as is described below.

As also shown in FIG. 8A, head 864 can be received over the proximal portion of bone anchor 150 with key 158 and mount 156 received within shaft 860 (see dashed line). In use, bone anchor 150 is inserted into the head 864 of shaft 860 with the head 154 and engagement features 155 engaged by head 864 and the key 158 secured within head 864. Bone anchor 150 is thus secured to implantation tool 850. Bone anchor 150 will not be released unless and until the surgeon pulls back on grip 874. Thus, bone anchor 150 and implantation tool can be inserted as one unit through a cannula to the implantation location in the spine facilitating the positioning and implantation of bone anchor 150.

FIG. 8B shows a detailed sectional view of the head 864 of the implantation tool 850 of FIG. 8A engaged with a bone anchor 150. As shown in FIG. 8B, head 864 includes a socket 865 for receiving and engaging head 154 of bone anchor 150. Socket 865 is designed to mate with head 154 in order to rotate the threaded shaft 152 of bone anchor 150. Thus, the interior of socket 865 may be hexagonal, octagonal or provided with flutes/splines etc., depending on the particular configuration of the head 154. Socket 865 should be able to apply sufficient torque to head 154 to implant the bone anchor 150 in a pedicle.

Referring again to FIG. 8B, head 864 also includes a bore 865 for receiving key 158 and mount 156 of adaptive bone anchor. As shown in FIG. 8B, key 158 includes a nipple 818 at the proximal end. A ball 852 is positioned within an aperture 867 which passes from the exterior of shaft 860 intersecting bore 865 adjacent nipple 818. Ball 852 is held by sleeve 870 in a position in which ball 852 protrudes into bore 865 so as to trap nipple 818 within bore 865. In a preferred embodiment, there are three such balls, however, only one is shown in this sectional view. Thus, head 154 is received in socket 865 and bone anchor 150 is locked to implantation tool 850 by the interaction of nipple 818 and ball(s) 852.

FIG. 8C shows a detailed sectional view of the head 864 of the implantation tool 850 of FIG. 8A configured to release a bone anchor 150. After implantation of bone anchor 150 it is necessary to remove implantation tool 850. The first step is to slide sleeve 870 proximally relative to shaft 860 as shown by arrow A. This is achieved by pulling back on grip 874 against the force of spring 872 (See FIG. 8A). As sleeve 870 is pulled proximally, ball(s) 852 enters a portion of sleeve 870 with a larger internal diameter. Ball(s) 852 can move away from engagement with nipple 818 and key 158 as they pass ramp 865 releasing nipple 818. At this stage both shaft 860 and sleeve 870 can be pulled together away from bone anchor 150.

Figure 8D:
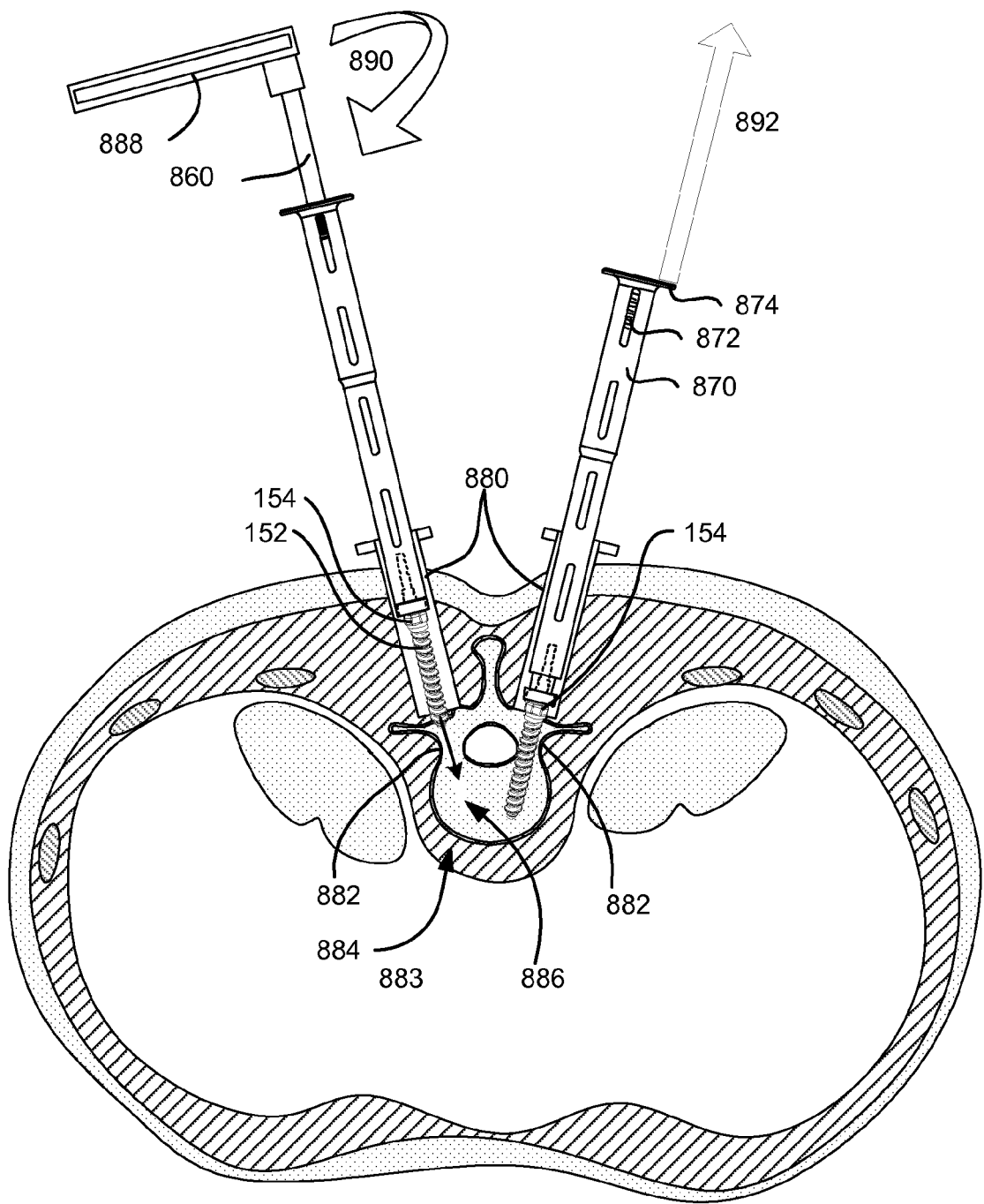
FIG. 8D is a transverse view of the lumbar spine illustrating use of the implantation tool of FIG. 8A to implant a bone anchor in the pedicles of a lumbar vertebra according to an embodiment of the invention.

FIG. 8D shows a transverse view of the lumbar spine illustrating use of the implantation tool 850 of FIG. 8A to implant bone anchors 150 in the pedicles 882 of a lumbar vertebra 884 according to an embodiment of the invention. As shown in FIG. 8D, implantation tool 850 may be used through a cannula 880 to implant the adaptive bone anchor in a minimally invasive procedure. The cannula 880 is introduced to the patient to approach the pedicles posteriorly. The pedicle 882 of the vertebra is 884 is exposed in the conventional fashion. A hole 886 is then drilled through the pedicle 882 into the vertebral body 883 of the vertebra. Next, a bone anchor 150 is selected having of suitable length, diameter and force/deflection characteristics is selected for implantation. The head 154 of the selected bone anchor 150 is inserted into the head 864 of implantation tool 850 and secured in place.

Referring now to the left side of FIG. 8D, bone anchor 150 and implantation tool 850 are inserted as one assembly through cannula 880 to the implantation site. Then bone anchor 150 is implanted by turning a handle 888 attached to the quick release on the proximal end of shaft 860. The bone anchor 150 is driven into hole 886 until the head 154 is at the surface of the vertebra 884 (see arrow 890). The torque to drive bone anchor 150 is provided by handle 888 through shaft 860 to head 154 of bone anchor 150.

Referring now to the right side of FIG. 8D, when bone anchor 150 is correctly positioned in pedicle 882, the physician pulls back on grip 874 against the force of spring 872. Sleeve 870 moves proximally relative to shaft 860. Shaft 860 releases the grip on bone anchor 150 and then both shaft 860 and sleeve 870 move away from cannula 880 and out of the patient (see arrow 892). Bone anchor 150 is now correctly implanted and prepared for attachment to an adaptive spinal rod and/or other spinal stabilization assembly components.

FIGS. 9A-9D show views of an attachment tool for securing an adaptive spinal rod 100 to a bone anchor 150 according to an embodiment of the invention. FIG. 9A shows a perspective view of an attachment tool 950 for securing an adaptive spinal rod 100 to a bone anchor 150 (shown in FIG. 9C) according to an embodiment of the invention. Adaptive spinal rod 100 may be, for example, the adaptive spinal rod 100 of FIGS. 1A-1B. Bone anchor 150 may be, for example, the bone anchor 150 as shown in FIG. 1C.

Referring first to FIG. 9A, attachment tool 950 includes an inner shaft 960 received within a tubular sleeve 970. The length and diameter of attachment tool 950 is selected so as to allow use through a cannula in a minimally invasive surgical technique thereby reducing disruption of tissues adjacent the implantation site, reducing patient recovery time and improving surgical outcomes. Inner shaft 960 is free to rotate and slide within sleeve 970. Inner shaft 960 has at a proximal end an attached handle 962. In alternative embodiments shaft 960 may have a fitting to which a handle might be attached, for example, ratcheting handles, torque sensing handles and torque limiting handles Inner shaft has at a distal end a head 964 for engaging and securing the key of an adaptive spinal rod 100 (see FIG. 9B).

Referring again to FIG. 9A, sleeve 970 includes a butterfly grip 974 at the proximal end thereof. Sleeve 970, has at the distal end thereof, means for engaging and securing the female tool engagement features of a ball of an adaptive spinal rod 100 during connection to a bone anchor as is described below. In a preferred embodiment, head 964 includes a male hex fitting 972 with a central aperture 973. FIG. 9B shows an enlarged view of head 964 from the distal end of attachment tool 950. FIG. 9B shows male hex fitting 972 with central aperture 973. Through central aperture 973 is visible female hex socket 965 of head 964. Protruding into female hex socket 965 are two spring tabs 967.

FIGS. 9C and 9D show detailed sectional views of the distal end attachment tool 950 in relation to an adaptive spinal rod 100 and bone anchor 150. Referring first to FIG. 9C, which shows a detailed sectional view of the distal end of the attachment tool 950 of FIG. 9A, engaged with an adaptive spinal rod 100 and a bone anchor 150. As shown in FIG. 9C, male hex fitting 972 of head 964 of outer sleeve 970 fits into the tool engagement features of ball 130. At the same time the key 158 of bone anchor 150 is received within female hex socket 965 of inner shaft 960. When thus engaged, turning handle 962 relative to butterfly grip 974 (See FIG. 9A) can rotate ball 130 relative to bone anchor 150. Attachment tool 950 is designed to apply sufficient torque to ball 130 to secure ball 130 to bone anchor 150 and to breakaway key 158. In a preferred embodiment, attachment tool 950 should be able to provide greater than 30 foot pounds of torque.

FIG. 9D shows a detailed sectional view of the distal end of the attachment tool 950 of FIG. 9A after break away of key 158 of bone anchor 150. As shown in FIG. 9D, when ball 130 has been tightened onto bone anchor 150, tabs 967 on central aperture 973 engage either side of a nipple 818 of key 158 to secure key 158 within female hex socket 965. Thus, when key 158 breaks away it can be removed from the patient with connection tool 950 as shown.

FIGS. 9E-9F show lateral views of the lumbar spine illustrating steps of attaching an adaptive spinal rod 100 to a bone anchor 150 utilizing the attachment tool of FIG. 9A according to an embodiment of the invention. As shown in FIG. 9E, the adaptive spinal rod 100 is implanted after the bone anchor 150 and a polyaxial screw 940 have already been implanted. Adaptive spinal rod 100 is implanted in a cranial direction—preferably in a minimally invasive manner until adaptive spinal rod 100 is positioned adjacent bone anchor 150 and polyaxial screw 940. The key 158 of bone anchor 150 is then fed through ball 130 of adaptive spinal rod 100 as shown.

Next, as shown in FIG. 9F, connection tool 950 is inserted through a cannula 880 to engage ball 130 and key 158. Ball 130 is then turned relative to key 158 until it is fully secured to bone anchor 150. When ball 130 is fully secured to bone anchor 150, further torque is applied until key 158 (not shown) is sheared off. In a preferred embodiment, this requires 30 foot pounds of torque and is sufficient to lock ball 130 to bone anchor 150. Next, as shown in FIG. 9G, connection tool 950 can be removed from cannula 880. As previously described, key 158 (not shown) is retained inside attachment tool 950 for easy removal from the patient. As shown in FIG. 9H, a conventional tool 984 is then inserted through cannula 980 to operate polyaxial screw 940 to secure the other end of adaptive spinal rod 100.

Alternative Connector for Two-Level Spinal Prosthesis

Figure 10E:
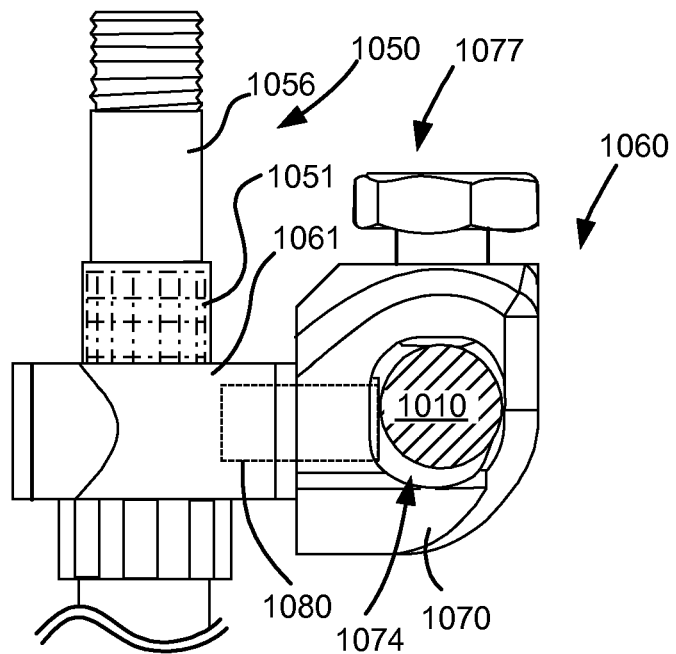
FIGS. 10E and 10F are views illustrating the clamping action of the polyaxial connector of FIG. 10C.
Figure 10F:
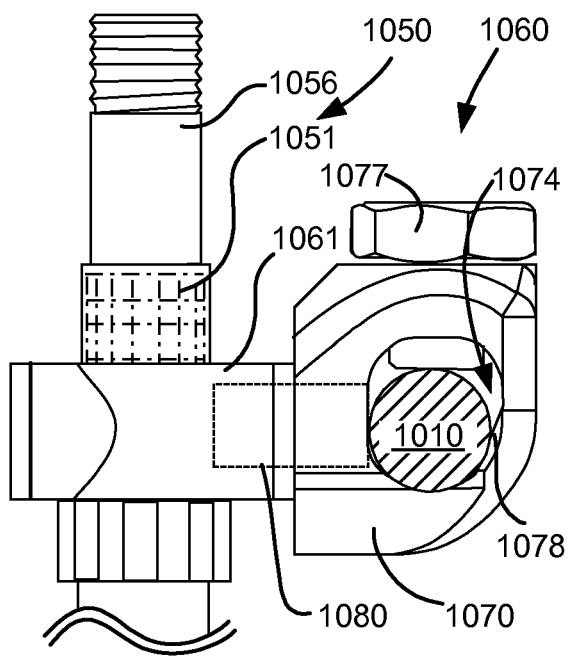
Figure 10G:
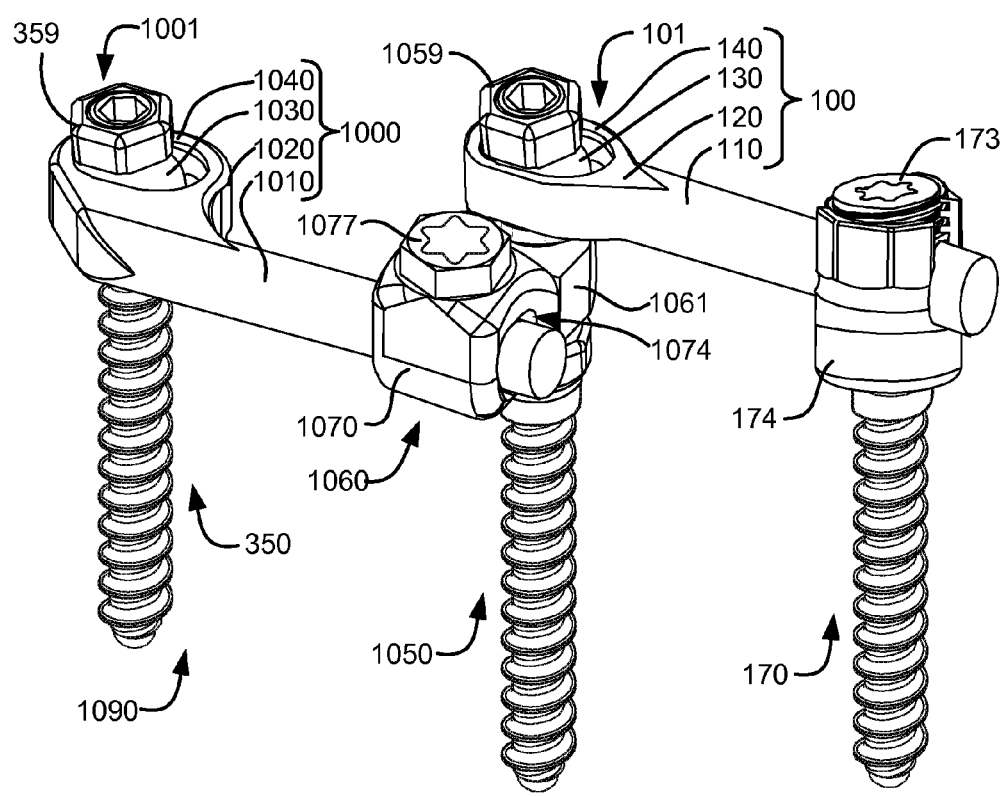
FIG. 10G is a perspective view illustrating a two-level adaptive spinal prosthesis utilizing the components of FIGS. 10A-10D.

In alternative embodiments, single-level adaptive spinal rods are connected using one or more connectors to assemble a multi-level adaptive spinal prosthesis. A range of polyaxial connectors adaptable for this purpose is disclosed in U.S. patent application Ser. No. 12/566,485 titled "Versatile Polyaxial Connector Assembly And Method For Dynamic Stabilization Of The Spine" to Mitchell et al. For example, FIGS. 10A-10G show views of a polyaxial connector 1060 adapted for connecting a bone anchor 1050 to an adaptive spinal rod 1000 in a two-level adaptive spinal prosthesis 1004. Connector 1060 mounts externally to a second mount of a bone anchor 1050. FIG. 10A shows an example of an adaptive spinal rod 1000. FIG. 10B shows a bone anchor 1050 suitable for use with adaptive spinal rod 1000 and a connector. FIGS. 10C and 10D shows an exploded view of a connector, and components thereof, suitable for use with bone anchor 1050 and adaptive spinal rod 1000 as part of a two-level adaptive spinal prosthesis. FIGS. 10E and 10F illustrate operation of the polyaxial connector. FIG. 10G shows a two-level adaptive spinal prosthesis 1090 using the components of FIGS. 10A-10F.

Referring first to FIG. 10A, which is an exploded view of the components of a single level adaptive spinal rod 1000. Adaptive spinal rod 1000 includes rod 1010, housing 1020, arm 1021, ball 330 (see FIG. 3B) and cap 1040a. Rod 1010a is connected to one side of housing 1020a. Rod 1010a is similar in shape and material to standard spinal rods. Rod 1010a is adapted for mounting to the second segment 1000b (See FIG. 10B) of adaptive spinal rod 1000 (See FIG. 10C). Rod 1010 is, in a preferred embodiment, a cylinder about 5 mm to 6.5 mm in diameter and from 105 mm to 100 mm in length. Housing 1020 is preferably in the form of a flattened disc. An arm projects laterally from housing 1020 and connects to rod 1010. Housing 1020 has a slot 1022 passing therethrough (similar in design in function to slot 122 of FIG. 1A). Slot 1022 is shaped to receive ball 1030. The long axis of slot 1022 is parallel to the long axis of rod 1010. Cap 1040 is adapted to fit within slot 1022 of housing 1020. As shown in FIG. 10A, cap 1040 and slot 1020 cooperate to form race 1002 in which ball 1030 is contained or trapped to form a linear ball-joint as previous described. Although ball 1030 is contained or trapped within race 1002, ball 1030 can pivot and rotate within race 1002. It is to be understood that slot 1022 and thus race 1002 can be linear and also can be configured in accordance with the various configurations of slot 1022 and linear race 1002 shown in the embodiments of FIGS. 1A-1H. Aperture 1036 of ball 1030 is accessible and configured for mounting adaptive spinal rod 1000 to a bone anchor as shown in FIG. 10B.

FIG. 10B, shows a bone anchor 1050 configured for attachment of adaptive spinal rod 1000 to a vertebra. As shown in FIG. 10E, bone anchor 1050 includes a threaded shaft 1052 at the distal end. Threaded shaft 1052 is sized and configured for engaging a vertebra. In preferred embodiments threaded shaft 1052 is sized and configured for implantation in the pedicle of a vertebra. Attached to threaded shaft 1052 is head 1054. Head 1054 includes surface features 1055 which permit head to be engaged by a tool to rotate head 1054 and threaded shaft 1052 and drive bone anchor 1050 into a desired implant location. Protruding proximally from head 1054 is a second mount 1051. Second mount 1051 can be provided with surface texture e.g. knurling and/or surface features. Second mount 1051 is designed to be received in and engaged by connector 1060 of FIGS. 10C-10G. Protruding proximally from second mount 1051 is first mount 1056. First mount 1056 has a smooth exterior surface 1057 to receive ball 1030 of FIG. 10A. Protruding proximally of first mount 1056 is a threaded shaft 1057 for attaching a nut 1059 to secure ball 1030 of FIG. 10A. In the proximal end of threaded shaft 1057 is an aperture 1058. Aperture 1058 is shaped such that the aperture 1058 can be engaged by a driver for implanting/removing bone anchor 1050 and/or attaching nut 1059. For example, aperture 1058 has, in some embodiments, a hexagonal or octagonal cross-section.

Referring next to FIG. 10C, which is an exploded view of connector 1060 the connector 1060 revealing the components: snap ring 1002, locking screw 1077, clamp ring 1061, swivel 1070 and plunger 1080. As shown in FIG. 10C, clamp ring 1061 is generally annular with a bore 1069. Bore 1069 of clamp ring 1061 is sized such that the clamp ring 1061 can slide freely up and down second mount 1051 of bone anchor 1050 (see FIG. 10B) and rotate around the second mount 1051 before the clamp ring 1061 is locked. A rim 1063 is, in some embodiments, provided around bore 1069. On one side of clamp ring 1061 is a cylindrical extension 1064. A bore 1062 passes through the middle of cylindrical extension 1064 and intersects with bore 1069 of the clamp ring 1061. Cylindrical extension 1064 has a groove 1068 on its outer surface. The groove 1068 is sized so that snap ring 1002 fits entirely within the groove 1068 when snap ring 1002 is compressed.

Referring to FIGS. 10C and 10D (which shows an alternate view of swivel 1070). Connector 1070 has a channel 1074 which passes through swivel 1070 and which is sized to receive therethrough the rod of an adaptive spinal rod (or conventional spinal rod). Swivel 1070 has a threaded aperture 1078 sized to fit locking screw 1077. Threaded aperture 1078 intersects channel 1074 to allow set screw 1077 to contact a spinal rod within channel 1074. An aperture 1071 passes through another side of swivel 1070 and intersects with channel 1074. Aperture 1071 is sized to receive cylindrical extension 1064 of clamp ring 1061 and plunger 1080. Aperture 1071 has a lip 1075 which prevents plunger 1080 from slipping too far into channel 1074. Aperture 1071 also has a groove 1072 sized to engage snap ring 1002.

Referring again to FIG. 10C, plunger 1080 is generally cylindrical and sided to fit within bore 1062. The first end 1082 of plunger 1080 is inserted into bore 1062 of clamp ring 1061. First end 1082 is, in some embodiments, concave so as to better engage a bone anchor placed in bore 1069. Plunger 1080 has a lip 1086 at its second end 1084 so that it cannot fall entirely through bore 1062. Snap ring 1002 is designed to fit within groove 1068 of cylindrical extension 1064. In an uncompressed state snap ring 1002 is slightly smaller in diameter to fit over cylindrical extension 1064. To insert snap ring 1002 into groove 1064, snap ring 1002 is expanded slightly and pushed over cylindrical extension 1064 of clamp ring 1061 until snap ring 1002 snaps into groove 1068.

During assembly, snap ring 1002 is compressed into groove 1064 of cylindrical extension 1064 while cylindrical extension 1064 is inserted into aperture 1071. When cylindrical extension 1064 is inserted the correct distance into aperture 1071, groove 1068 becomes aligned with groove 1072 and snap ring 1002 can expand into groove 1072. When snap ring 1002 has expanded into groove 1072 a portion of snap ring 1002 remains within each of grooves 1072 and 1068. Cylindrical extension 1064 is thereby locked into aperture 1071 of swivel 1070. Cylindrical extension 1064 can, however, rotate within aperture 1071. Furthermore, plunger 1080 may still slide somewhat in and out of bore 1062 of clamp ring 1061. Second end 1084 of plunger 1080 protrudes slightly into the channel 1074 when assembled as described below. When the plunger 1080 is pushed through bore 1062 outwards from channel 1074 the plunger grips the second mount and prevents the clamp ring 1061 from moving in any direction.

FIGS. 10E and 10F illustrate the clamping action of connector 1060 to rod 1010 and to the second mount 1056 of bone anchor 1050. As shown in FIG. 10E, rod 1010 (shown in section) is received in channel 1074 of connector 1060. Second mount 1051 is received in bore 1069 of clamp ring 1061. Plunger 1080 (shown by dotted line) sits in bore 1062 (not shown) of clamp ring 1061 between rod 1010 and second mount 1051. In this unclamped configuration, clamp ring 1061 may slide up and down on second mount 1051 and rotate around second mount 1051; swivel 1070 is free to also free to rotate relative to clamp ring 1061; and rod 1010 can slide freely in and out of channel 1074. The unclamped configuration thereby allows adjustment of the direction and angle of rod 1010 with several degrees of freedom.

As shown in FIG. 10F, when set screw 1077 is tightened against a rod 1010 within channel 1074 of swivel 1070, the set screw 1077 pushes rod 1010 against a ramp 1078 at the opposite side of channel 1074 from locking screw 1077. Ramp 1078 pushes rod 1088 against plunger 1080. Plunger 1080 is forced by rod 1010 through bore 1062 (not shown) in clamp ring 1061. Plunger 1080 is thereby forced against second mount 1051 of the bone anchor 1050 preventing further movement of clamp ring 1061 relative to bone anchor 1050. The force of plunger 1080 against second mount 1051 also applies force between grooves 1068 and 1072 and snap ring 1002 (see FIGS. 10C and 10D) thereby preventing further rotation of swivel 1070 relative to clamp ring 1061. Additionally rod 1010 is locked in position within aperture 1074. Operation of the single set screw 1077 serves to place the connector in a clamped configuration and lock the clamp ring 1061 to the second mount 1051 of the bone anchor 1050, lock swivel 1070 in a fixed position relative to clamp ring 1061 and secure rod 1010 within the channel 1074 of connector 1060.

The connector 1060 of FIGS. 10C-10F may be used, in some embodiments, to construct an adaptive stabilization assembly for one or more levels of the spine of a patient. FIG. 10G shows an example of a two-level adaptive stabilization assembly 1090 utilizing the connector 1060 of FIGS. 10C-10F. FIG. 10G shows how the components may be assembled and implanted in the spine of a patient to provide a multilevel adaptive stabilization assembly which provides stabilization of the spine and load sharing while preserving motion. Note that an identical or similar construct would preferably be implanted on the left side of the spine.

As shown in FIG. 10G, rod 110 of adaptive spinal rod 100 is mounted to head 174 of spinal screw 170. Ball 130 of adaptive spinal rod 100 is secured to bone anchor 1050 by nut 1059. Sliding ball-joint 101 permits bone anchor 1050 to slide, pivot and rotate relative to spinal screw 170. Connector 1060 is also mounted to bone anchor 1050. Set screw 1077 secures clamp ring 1061 of connector to bone anchor 1050 and also secures rod 1010 of adaptive spinal rod 1000 within channel 1074 of swivel 1070. Ball 1030 of adaptive spinal rod 1000 is secured to bone anchor 350 by nut 359. Sliding ball-joint 1001 permits bone anchor 1050 to slide pivot and rotate relative to bone anchor 350. Adaptive spinal prosthesis is typically assembled in vivo by first implanting the bone anchors 1050, 350 and spinal screw 170 in pedicles of adjacent vertebra. After implanting the bone anchors 1050, 350 and spinal screw 170, the connector 1061 is placed over bone anchor 1050 and rod 1010 is positioned within channel 1074 of the connector 1060. Ball 1030 is then secured to bone anchor 350. After securing ball 1030, the position of rod 1010 and swivel 1070 are adjusted and then connector 1060 is locked by tightening set screw 1077.

Ball 130 of adaptive spinal rod 100 is secured to bone anchor 1050 by nut 1059. Rod 110 is then placed within head 174 of spinal screw 170. The position of the rod 110 is then adjusted relative to head 174 and the head 174 is secured to rod 110 by set screw 173. Adaptive stabilization assembly 1090 spans two vertebrae two levels of the spine (three vertebrae). Connector 1060 and adaptive spinal rods 100, 1000 permit assembly of adaptive stabilization assembly 1090 for a wide range of different patient anatomies and/or placement of bone anchors 350, 1050 and spinal screw 170. Connector 1060 is particularly useful where, as here, there is slight lateral displacement between the bone anchor positions on either side of a level.

Alternative Adaptive Spinal Rods

Figure 11A:
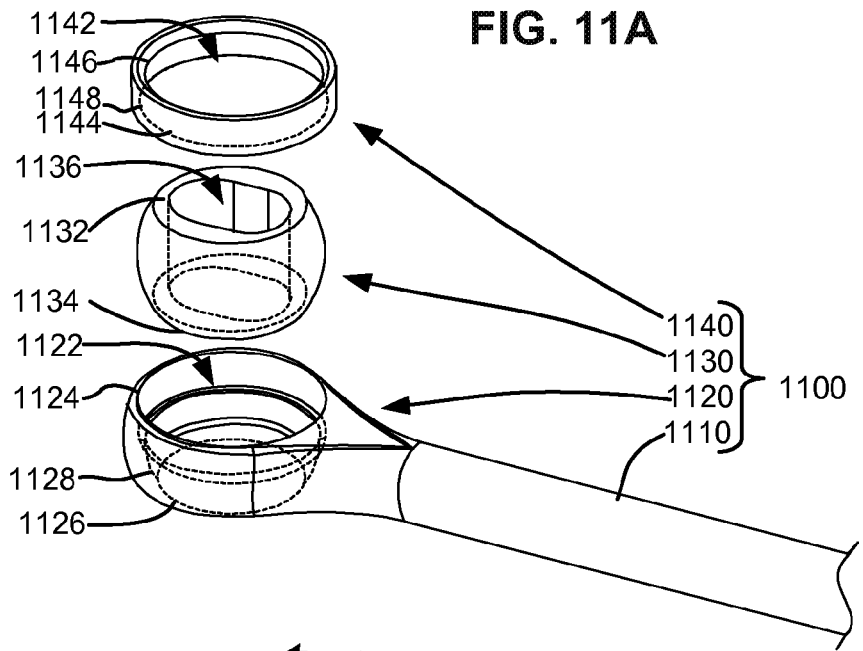
FIG. 11A is an exploded view of an adaptive spinal rod according to an alternative embodiment of the present invention.
Figure 11B:
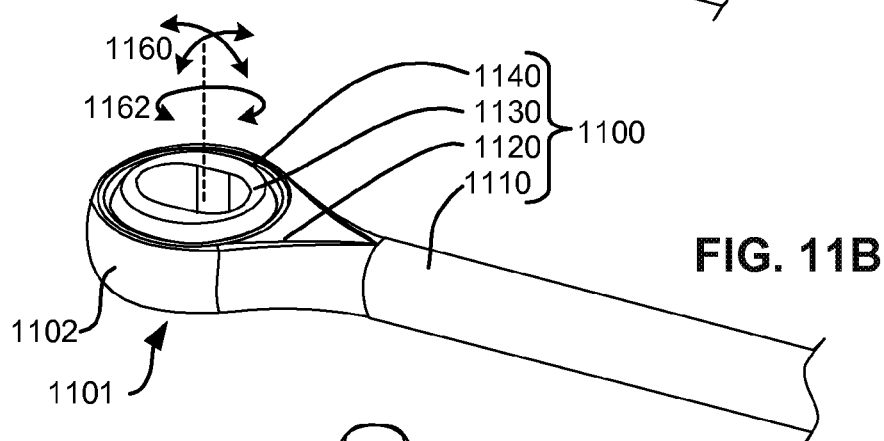
FIG. 11B is a perspective view of the adaptive spinal rod of FIG. 11A as assembled.
Figure 11C:
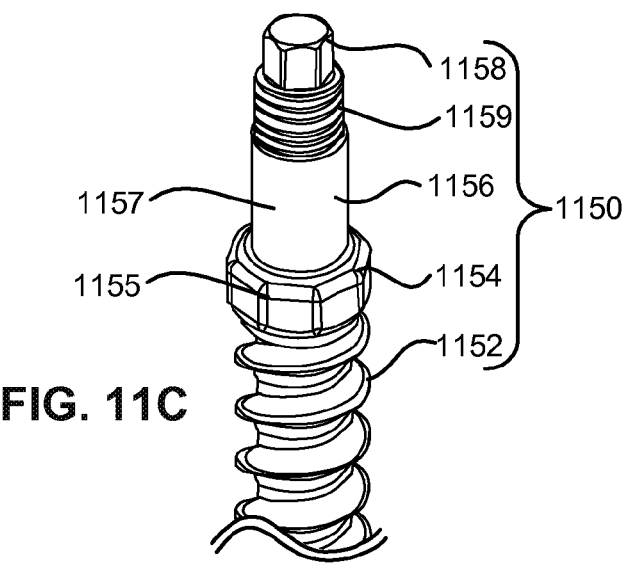
FIG. 11C is a perspective view of a bone anchor adapted for use with the adaptive spinal rod of FIGS. 11A, and 11B according to an embodiment of the present invention.
Figure 11D:
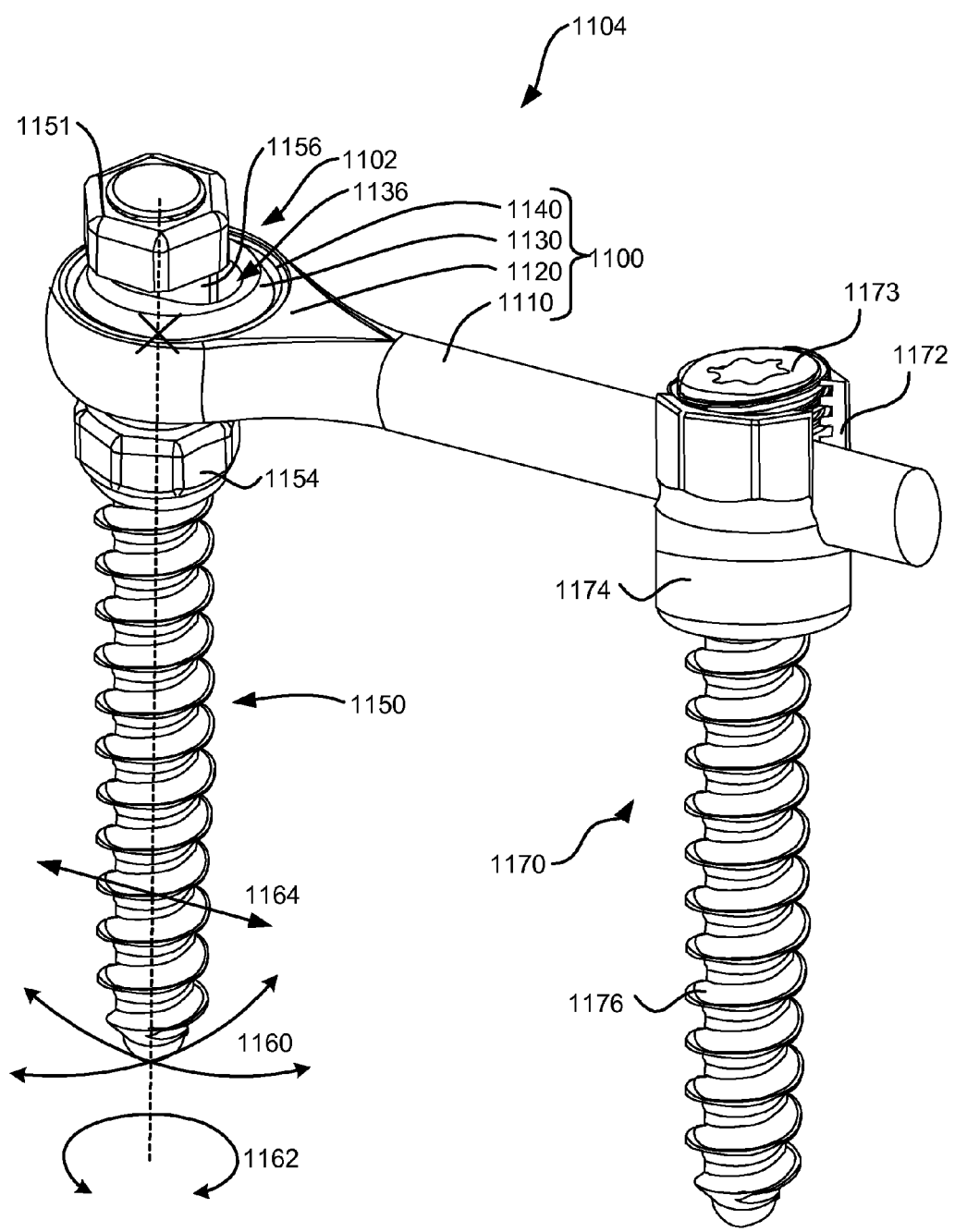
FIG. 11D is a perspective view of a spinal prosthesis including the adaptive spinal rod of FIGS. 11A and 11B and bone anchor of FIG. 11C.

FIGS. 11A-11G are views of an adaptive stabilization system including an alternative adaptive spinal rod according to an embodiment of the present invention. FIG. 11A is an exploded view showing the components of an adaptive spinal rod. FIG. 11B is a perspective view of the assembled adaptive spinal rod. FIG. 11C shows a perspective view of a bone anchor suitable for mounting the adaptive spinal rod to a vertebra. FIG. 11D shows a spinal prosthesis assembly including the adaptive spinal rod, a bone anchor and a conventional pedicle screw. FIGS. 11E, 11F, 11G and 11H are sectional views illustrating the kinematics of the bone anchor relative to the adaptive spinal rod.

Referring first to FIG. 11A, which is an exploded view of the components of an adaptive spinal rod 1100. Adaptive spinal rod 1100 has three components: rod 1110, ball or ball-shaped mount or partially-spherical mount 1130 and cap 1140. Rod 1110, preferably, is connected and/or includes at one end a housing 1120. Rod 1110 is similar in size, shape and material to standard spinal rods. Rod 1110 is adapted for mounting to a standard pedicle screw or polyaxial screw (not shown). Rod 1110 is, in preferred embodiments, a cylinder about 5 mm to 6.5 mm in diameter and from 35 mm to 100 mm in length. Housing 1120 is preferably in the form of a flattened disc. Housing 1120 has an aperture 1122 passing therethrough. Aperture 1122 is circular in section to receive ball 1130. Aperture 1122 is shaped to receive ball 1130 from open side 1124. However, the closed side 1126 of aperture 1122 is too small for ball 1130 to pass. Closed side 1126 of aperture 1122 has a curved surface 1128 adapted to engage ball 1130. In one embodiment curved surface 1128 has the same radius of curvature as ball 1130. Open side 1124 of aperture 1122 is shaped to receive cap 1140 after placement of ball 1130. Cap 1140 can be force fit or welded to the housing 1120 to hold ball 1130 in place. In preferred embodiments, rod 1110 and housing 1120 are made in one piece from titanium or titanium alloy.

As indicated above, cap 1140 is adapted to fit within aperture 1122 of housing 1120. Cap 1140 has a cap aperture 1142 therethrough. The open side 1144 of cap aperture 1142 is configured to admit a portion of ball 1130. The closed side 1146 of cap aperture 1142 is too small for ball 1130 to pass. The interior of cap aperture 1142 has a curved surface 1148 adapted to engage ball 1130. In one embodiment curved surface 1148 has the same radius of curvature as ball 1130. During assembly, ball 1130 is placed into aperture 1122 of housing 1120. Cap 1140 is then secured into aperture 1122 of housing 1120 trapping or containing ball 1130 between cap 1140 and housing 1120 to form a ball-joint (see FIG. 11E). When assembled, ball 1130 can pivot and rotate within a race created by curved surface 1148 of cap 1140 and curved surface 1128 of housing 1120.

Ball 1130 is in the form of a sphere truncated on two opposing sides 1132, 1134. An elongated slot 1136 passes through ball 1130 from side 1132 to side 1134. Elongated slot 1136 is preferably shaped like an oval and/or a rectangle having rounded corners, and/or "race tracks" and/or elliptical. In the preferred embodiment, the walls of slot 1136 are about perpendicular to the truncated opposing sides 1132, 1134. The width (shorter dimension) 1137 of slot 1136 is preferably at least slightly larger than the diameter of the posterior mount 1156 of bone anchor 1150 to be received in the slot 1136 (not shown, but see FIG. 11C). In embodiments, the length (longer dimension) 1139 of slot 1136 is about 1 mm to 5 mm greater than the diameter of the posterior mount 1156 to be received in slot 1136. In preferred embodiments, the length of slot 1136 is about 1 mm to 3 mm greater than the diameter of the posterior mount 1156 to be received in slot 1136. Ball 1130 is adapted to receive a smooth mount 1156 of a bone anchor 1150—the mount 1156 is held in place using a separate nut 1151 (see FIG. 11D). Slot 1136 is elongated to allow a bone anchor to slide (and rotate) in slot 1136 as explained below. Thus, when secured in place, the posterior mount 1156 can slide and rotate within slot 1136. The bone anchor 1150 can slide, rotate and pivot relative to the spinal rod 1110. The ball 1130 can rotate and pivot inside housing 1120 and spinal rod 1100. The range of sliding movement of the mount 1156 is dependent upon the length of the elongated slot 1136.

FIG. 11B shows a fully assembled adaptive spinal rod 1100 in which ball 1130 is positioned between cap 1140 and housing 1120. Aperture 1122 of housing 1120 and cap aperture 1142 of cap 1140 cooperate to from a partially-spherical race 1102 in which ball 1130 is contained or trapped. Although ball 1130 is contained or trapped within circular race 1102, ball 1130 can pivot and rotate within circular race 1102 as shown by arrows 1160, 1162. In combination, the surface of ball 1130 and the linear race 1102 form a ball-joint 1101.

As shown in FIG. 11B, slot 1136 of ball 1130 is accessible from both sides of the housing 1120 after ball 1130 has been secured between cap 1140 and housing 1120. Slot 1136 of ball 1130 is accessible and configured for mounting adaptive spinal rod 1100 to a bone anchor, for example, the bone anchor shown, in FIG. 11C. The longitudinal axis of slot 1136 is shown in FIG. 11B to be aligned with the longitudinal axis of rod 1110. However, because ball 1130 can rotate within circular race 1102, slot 1136 can be aligned at an angle to, as well as parallel, to the longitudinal axis of rod 1110. As further discussed herein, this arrangement allows the spinal rod 1110 to be out of alignment with the motion of the spine. When the surgical slot 1136 is aligned with the direction of movement of the spine, and slot 1136 can be at an angle with the longitudinal axis of the spinal rod 1110.

FIG. 11C shows a bone anchor 1150 configured for attachment of adaptive spinal rod 1100 to a vertebra. As shown in FIG. 11C, bone anchor 1150 includes a threaded shaft 1152 at the distal end. Threaded shaft 1152 is sized and configured for engaging a vertebra. In preferred embodiments, threaded shaft 1152 is sized and configured for implantation in the pedicle of a vertebra. Attached to threaded shaft 1152 is head 1154. Head 1154 includes surface features 1155 which permit head to be engaged by a tool to rotate head 1154 and threaded shaft 1152 and drive bone anchor 1150 into a desired implant location in a vertebra. Protruding proximally from head 1154 is a mount 1156. Mount 1156 has a smooth cylindrical exterior surface 1157 to which ball 1130 of FIGS. 11A and 11B can be mounted. Protruding proximally of mount 1156 are threaded shaft 1159 and key 1158. Threaded shaft 1159 is configured for attachment of a nut 1151 (not shown, but see FIG. 11D) to secure ball 1130 to mount 1156. Key 1158 is shaped such that the key 1158 can be engaged by a driver for implanting bone anchor 1150 and/or attaching ball 1130. For example, key 1158 has, in some embodiments, a hexagonal or octagonal cross-section. At the base of key 1158 is, in some embodiments, a groove which reduces the cross-section of material such that the key 1158 is designed to breakaway when a predetermined amount of torque is applied to key 1158. The breakaway torque is determined by the shape of the groove and the remaining cross-section of material. The breakaway key can thus be used to ensure that the correct amount of torque is applied when securing a nut to threaded shaft 1159.

FIG. 11D shows a perspective view of a spinal prosthesis 1104 including adaptive spinal rod 1100 mounted to bone anchor 1150 by a nut 1151. Spinal prosthesis 1104 includes, in this embodiment: adaptive spinal rod 1100 of FIGS. 11A and 11B; bone anchor 1150 of FIG. 11C; and a conventional spinal screw 1170. Spinal screw 1170 is, in some embodiments, a polyaxial pedicle screw. As shown in FIG. 11D, adaptive spinal rod 1100 is secured at one end to conventional spinal screw 1170. Rod 1110 has been secured into a slot 1172 in a head 1174 of spinal screw 1170 by a set screw 1173. Set screw 1173 secures spinal rod 1110 in a fixed position relative to head 1174 and also, in some embodiments, locks the position of head 1174 relative to the threaded screw shaft 1176 of spinal screw 1170. In spinal prosthesis 1104, when implanted, rod 1110 and housing 1120 of adaptive spinal rod 1100 are secured in a fixed position relative to spinal screw 1170 (and any vertebra to which it is mounted).

Adaptive spinal rod 1100 is secured, at the other end to bone anchor 1150 of FIG. 11C through ball 1130. Ball 1130, contained or trapped within race 1102, has been secured to posterior mount 1156 of bone anchor 1150. Breakaway key 1158 (see FIG. 11C) has been broken away from posterior mount 1156 during implantation, and removed from the patient. Although ball 1130 has been secured to mount 1156, ball 1130 is still able to pivot and rotate within race 1102 relative to housing 1120 of adaptive spinal rod 1100. Moreover, posterior mount 1156 can still slide and rotate within slot 1136 of ball 1130. It is to be understood that mount 1156 of bone anchor 1150 can slide along the longer dimension 1139 of slot 1136 in ball 1130. Further, if bone anchor 1150 is loosely secured to ball 1130 by nut 1151, bone anchor 1150 can slide through ball 1130 in the directions of sides 1132 and 1134. Consequently, with bone anchor 1150 secured to adaptive spinal rod 1100 through ball 1130 (FIG. 11E), bone anchor 1150 is still able to slide, pivot and rotate relative to rod 1110 and spinal screw 1170. (See FIGS. 11E, 11F, 11G and 11H). Similarly, the spinal rod 1100 can slide, pivot and rotate relative to posterior mount 1156 and also bone anchor 1150 (see FIGS. 11E, 11F, 11G and 11H).

Referring again FIG. 11D, pivoting of ball 1130 allows bone anchor 1150 to pivot relative rod 1110 as shown by arrows 1160. In preferred embodiments, bone anchor 1150 can pivot in all directions from perpendicular without interference between housing 1120 and either head 1154 or nut 1151. Head 1154 and nut 1151 are, in some embodiments, provided with relief features to prevent interference with housing 1120. Rotation of ball 1130 allows bone anchor 1150 to rotate around its longitudinal axis relative to rod 1110 as shown by arrow 1162. Such rotation is also permitted by rotation of mount 1156 within slot 1136. Sliding movement of posterior mount 1156 within slot 1136 also allows linear movement of bone anchor 1150 relative to rod 1110 as shown by arrow 1164. This linear movement is shown aligned with the longitudinal axis of rod 1110. However, as previously stated, because ball 1130 can rotate, the longitudinal axis of slot 1136 can align itself at an angle to the longitudinal axis of rod 1110 to better accommodate relative movement of the vertebrae in which bone anchors 1150 and 1170 are implanted.

Figure 11E:
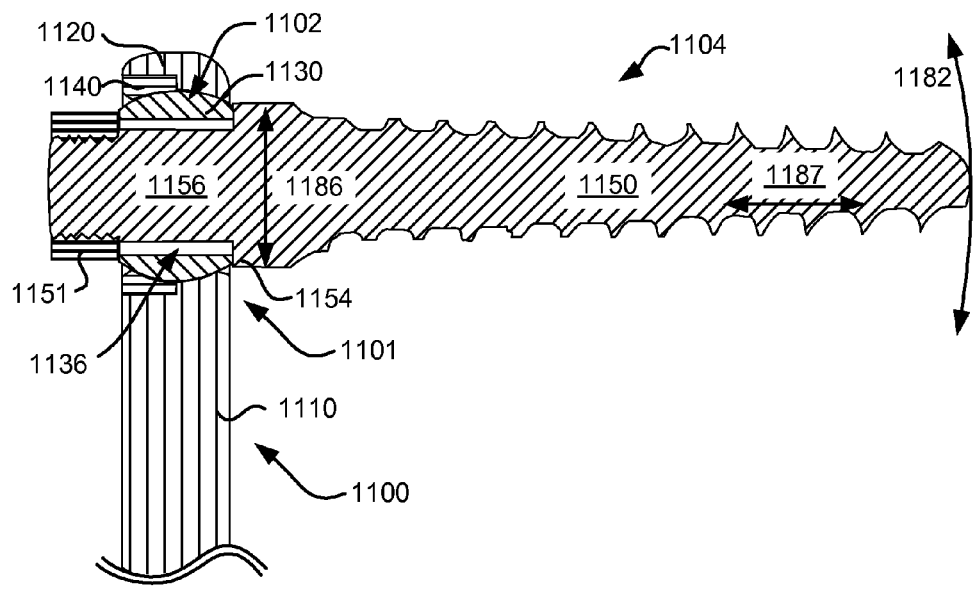
FIG. 11E is a saggital section of the spinal prosthesis of FIG. 11D.
Figure 11F:
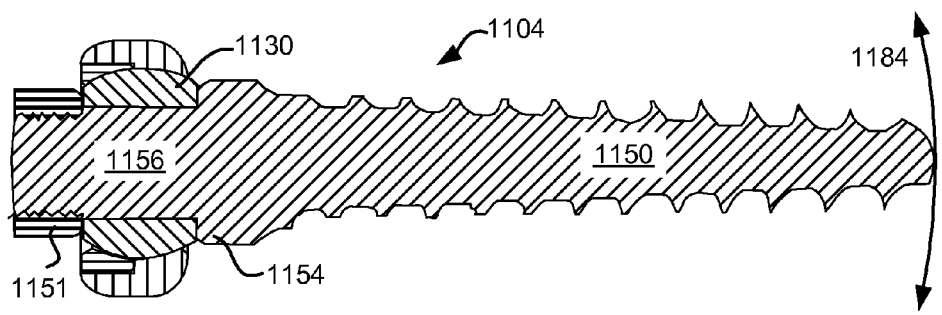
FIG. 11F is a transverse section of the spinal prosthesis of FIG. 11D.
Figure 11G:
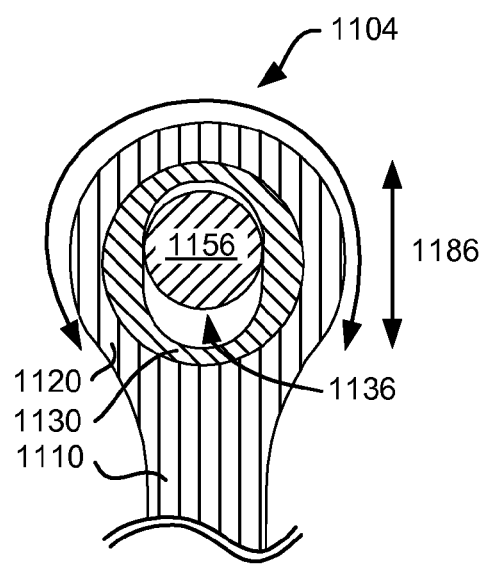
FIG. 11G is a dorsal section of the spinal prosthesis of FIG. 11D.
Figure 11H:
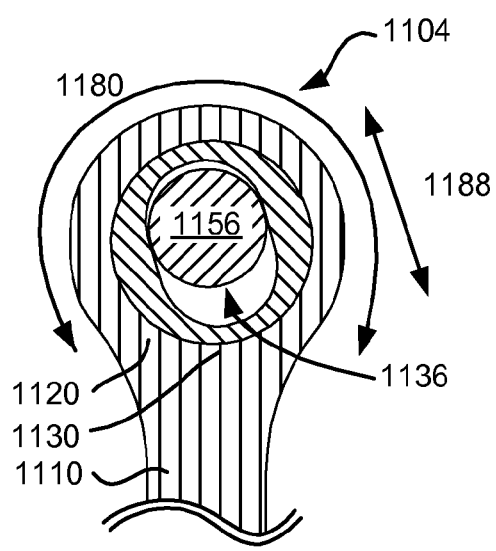
FIG. 11H is a dorsal section of the spinal prosthesis of FIG. 11D.

FIGS. 11E, 11F, 11G and 11H are partial sectional views of spinal prosthesis 1104 of FIG. 11D illustrating the kinematics of bone anchor 1150 relative to adaptive spinal rod 1100 in different planes. FIG. 11E shows a section through bone anchor 1150 and adaptive spinal rod 1100 in a substantially saggital plane. FIG. 11F shows a section through bone anchor 1150 and adaptive spinal rod 1100 in a substantially transverse plane. FIGS. 11G and 11H show sections through bone anchor 1150 and adaptive spinal rod 1100 in a substantially dorsal plane through the middle of the housing 1120.

Referring first to FIG. 11E shows a section through bone anchor 1150 and adaptive spinal rod 1100 in a substantially saggital plane (vertical and including the longitudinal axis of bone anchor 1150). As shown in FIG. 11E, ball 1130 is contained or trapped between cap 1140 and housing 1120 to form a ball-joint. Ball 1130 can pivot within the housing 1120 within limits imposed by contact between housing 1120, cap 1140, nut 1151 and head 1154. Additionally, posterior mount 1156 can slide within slot 1136 of ball 1130 within limits imposed by contact of posterior mount 1156 and the walls of slot 1136. Additionally, bone anchor 1150 can rotate in slot 1136. As a result, bone anchor 1150 can pivot in the saggital plane as shown by arrow 1182 and translate in the saggital plane as shown by arrow 1186 and rotate. Additionally, if desired, the nut 1151 can be fastened to threaded shaft 1159 in a manner that allows the bone anchor 1150 to translate along the longitudinal axis along the direction of arrow 1187. This can be accomplished by providing for a longer posterior mount 1156 that distances nut 1131 further from the ball 1130 than is shown in FIG. 11G. This arrangement can be provided in the other embodiments discussed herein.

In the saggital plane shown in FIG. 11E, slot 1136 allows bone anchor 1150 a limited range of vertical movement which corresponds to spinal flexion/extension (shown by arrow 1186). The desired range of vertical motion 1186, and thus the dimensions of slot 1136, are selected based upon the anatomical and functional needs of a patient. In embodiments, the range of movement is limited to less than 5 mm. In preferred embodiments, the range of translational movement is approximately 2 mm. The difference between the length of slot 1136 and the diameter of posterior mount 1156 controls the linear range of movement. Further, for large patients, the range of motion can be greater than 5 mm.

In the saggital plane shown in FIG. 11E, the ball-joint also allows bone anchor 1150 a limited angular range of movement which corresponds to spinal flexion/extension (shown by arrow 1182). The desired range of angular motion 1182, is selected based upon the anatomical and functional needs of a patient. In the embodiments, preferably the range of angular movement in the saggital plane is limited to less than 15 degrees.

Referring now to FIG. 11F which shows a section through bone anchor 1150 and adaptive spinal rod 1100 in a substantially transverse plane. In the transverse plane shown in FIG. 11F, the ball-joint 1101 allows bone anchor 1150 a limited angular range of movement which corresponds to spinal rotation (shown by arrow 1184). The range of angular movement is limited by contact between housing 1120 and cap 1140 with nut 1151 and/or head 1154. The desired range of angular motion 1184, and thus the shape of housing 1120, cap 1140, nut 1151 and head 1154 can be selected based upon the anatomical and functional needs of a patient. In the embodiments, preferably the range of angular movement in the transverse plane is limited to less than 10 degrees in each direction. In other embodiments, the range of angular movement can be 10 degrees or greater. The range of angular movement in the transverse plane can, in some embodiments, be different than the range in the saggital/vertical plane.

Referring next to FIG. 11G which shows a section through bone anchor 1150 and adaptive spinal rod 1100 in a substantially dorsal plane (vertical and perpendicular to the longitudinal axis of bone anchor 1150). Bone anchor 1150 is oriented either directly into or directly out of the page in this transverse view through housing 1120 and posterior mount 1156. As shown in FIG. 11G, ball 1130 is contained or trapped in housing 1120. Ball 1130 can rotate within race 1102 and thus, in housing 1120. Mount or post 1156 of the bone anchor 1150 is contained or trapped in slot 1136 of ball 1130. Mount or post 1156 of the bone anchor 1150 can slide within slot 1136 as well as rotate within slot 1136. The mount 1156 and thus the bone anchor 1150 can pivot with respect to spinal rod

1100. Based on the embodiment of 11G, the spinal rod 1100 can slide, rotate and pivot relative to the bone anchor 1150. Similarly, the bone anchor 1150 can slide, rotate and pivot relative to the spinal rod 1100. Further, the ball 1130 can rotate and pivot relative to the spinal rod 1100 and the mount or post of the bone anchor can rotate and slide relative to the ball 1130.

Figure 11I:
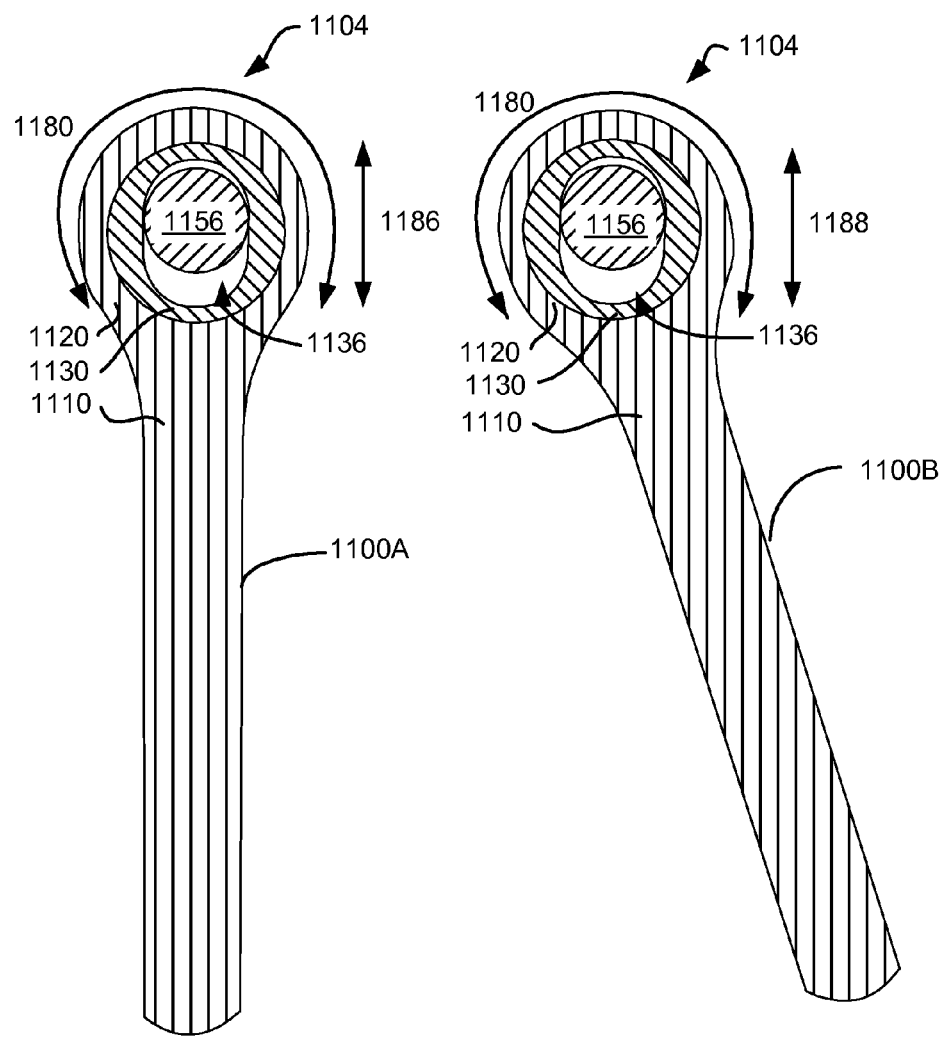
FIG. 11I is a composite view of FIGS. 11G and 11H.

In the dorsal plane shown in FIG. 11G, linear slot 1136 allows bone anchor 1150 the limited vertical range of movement 1186 as described above. Rotation of ball 1130 within housing 1120 and rotation of posterior mount 1156 within slot 1136 is unrestricted in this preferred embodiment, allowing bone anchor 1150 to rotate freely (360+ degrees) as shown by arrow 1180 which corresponds to lateral spinal twisting. The bone anchor 1150 rotates freely around the longitudinal axis of the spinal rod 1100. The range of rotation 1180 is not limited in this embodiment. However, features to limit such rotation could be designed into one or more of bone anchor 1150, ball 1130, cap 1140, and housing 1120 if desired with appropriate stop surface. The desired range of rotation 1180, can be selected, if necessary or desirable, based upon the anatomical and functional needs of a patient. FIGS. 11H and 11I show other dorsal sectional view. In FIG. 11H, slot 1136 is no longer aligned with the longitudinal axis of rod 1110. FIG. 11H illustrates how the linear movement axis 1188 can change based on rotation of ball 1130.

FIG. 11I is a representation of the implantation of two spinal rods 1100a and 1100b, side by side in generally a vertical orientation adjacent to the spine of a patient. These respective spinal rods are secured to an upper vertebra with first anchor screws and are secured to lower vertebra with second anchor screws. Due to the placement of the screws and the anatomy of the patient, spinal rod 1100b is placed about vertical and parallel to the spine. Again, due to the placement of the screws and the anatomy of the patient, spinal rod 1100a is placed at an angle to vertical and in this embodiment; spinal rod 1100a is placed at an angle of about 20 degrees or less. The direction of motion of the spine in flexion and extension along a vertical path is shown by arrow 1188. As is evident from FIG. 11I, spinal rod 1100a is not aligned with vertical arrow 1186. However, as ball 1130 can rotate in housing 1120, slot 1136 can rotate to be substantially parallel with vertical arrow 1188. Thus, the post or mount 1156 located in slot 1136 of spinal rod 1100a can slide or translate parallel to the direction of motion 1186 of the spine, even though spinal rod 1100a is not aligned with the direction of motion 1188.

With reference to FIGS. 11A to 11H and also to similar embodiments herein, aperture 1122 in the housing of 1120 at the end of spinal rod 1110, instead of being circular as shown, can also be elongated, oval or rectangular with rounded corners, or race-track shaped, as for example, shown in FIGS. 1G and 3A. Accordingly, in this embodiment, both the aperture 1122 in housing 1120 and slot 1136 in mount or ball 1130 are elongated, oval or rectangular with rounded corners or race-track shaped. Accordingly, in addition to the motions afforded between spinal rod 1100 and bone anchor 1150 due to the elongated slot 1136 as shown in FIG. 11G, motions afforded between spinal rod 1100 and bone anchor 1150 due to the elongated aperture 1122 are available in this embodiment.

Figure 12A:
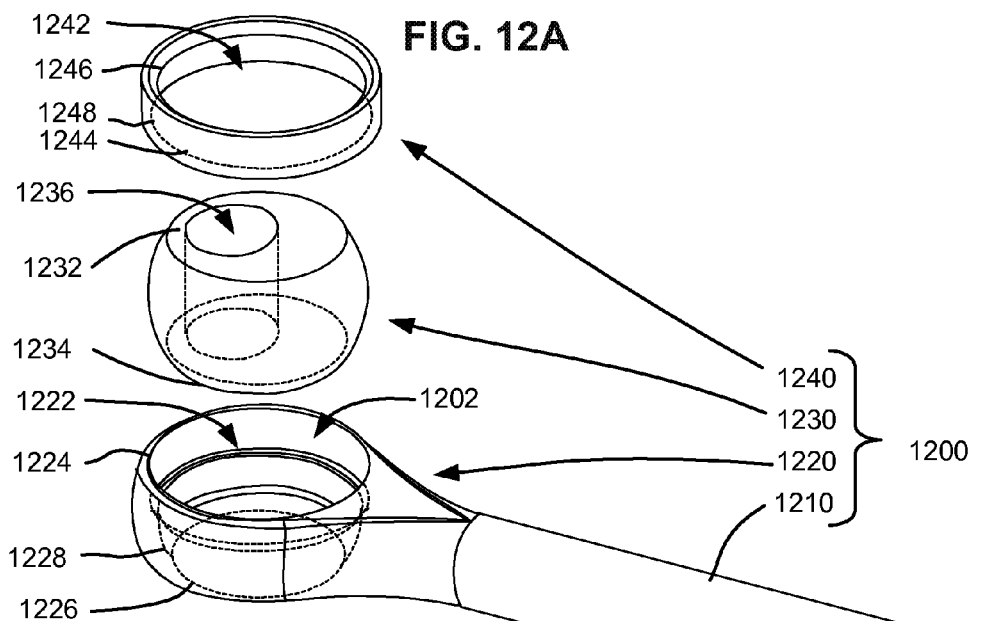
FIG. 12A is an exploded view of an adaptive spinal rod according to an alternative embodiment of the present invention.
Figure 12B:
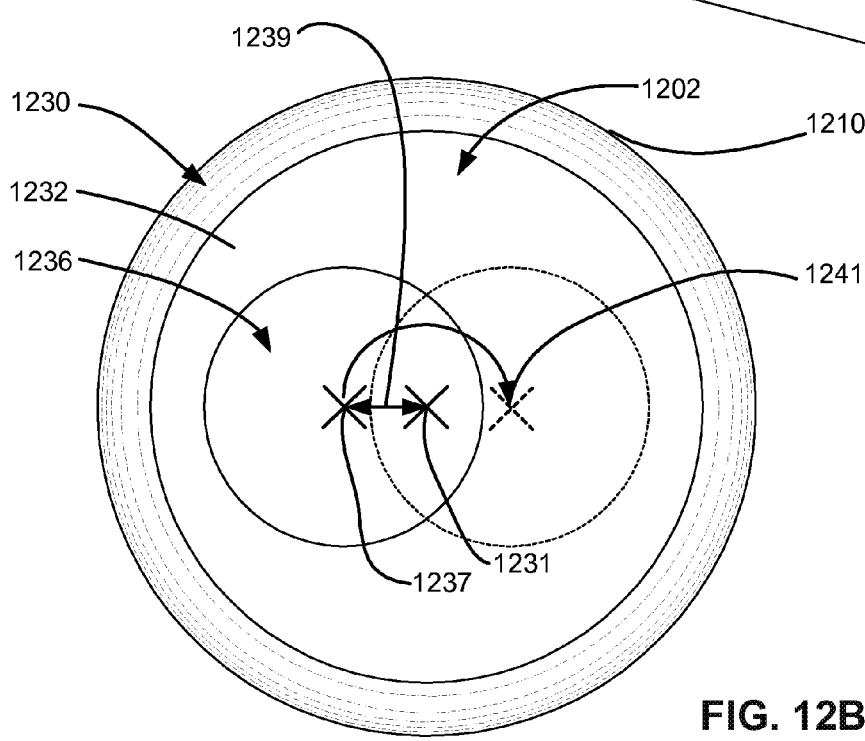
FIG. 12B is a plane view of the adaptive spinal rod of FIG. 11A as assembled.

FIGS. 12A-12B are views of an adaptive stabilization system including another alternative adaptive spinal rod according to an embodiment of the present invention. FIG. 12A is an exploded view showing the components of an adaptive spinal rod. FIG. 12B is a plane view of the assembled adaptive spinal rod. FIG. 12C is a perspective view of the adaptive spinal rod 1200 of FIG. 12A as assembled. Referring first to FIG. 12A, which is an exploded view of the components of an adaptive spinal rod 1200, adaptive spinal rod 1200 has three components: rod 1210, ball 1230 and cap 1240. Rod 1210 is preferably connected and/or includes at one end to housing 1220. Rod 1210, preferably, is similar in size, shape and material to standard spinal rods. Rod 1210 is preferably adapted for mounting to a standard pedicle screw or polyaxial screw (not shown). Rod 1210 is, in preferred embodiments, a cylinder about 5 mm to 6.5 mm in diameter and from 35 mm to 100 mm in length.

Housing 1220 is preferably in the form of a flattened disc. Housing 1220 has an aperture 1222 passing therethrough. Aperture 1222 is circular in section to receive ball 1230. Aperture 1222 is shaped to receive ball 1230 from open side 1224, however, the closed side 1226 of aperture 1222 is too small for ball 1230 to pass. Closed side 1226 of aperture 1222 has a curved surface 1228 adapted to engage ball 1230. In one embodiment, curved surface 1228 has the same radius of curvature as ball 1230. Open side 1224 of aperture 1222 is shaped to receive cap 1240 after placement of ball 1230. Cap 1240 can be force fit or welded to the housing 1220 to hold ball 1230 in place. In preferred embodiments, rod 1210 and housing 1220 are made in one piece from titanium or titanium alloy.

Cap 1240 is adapted to fit within aperture 1222 of housing 1220. Cap 1240 has a cap aperture 1242 therethrough. The open side 1244 of cap aperture 1242 is configured to admit a portion of ball 1230. The closed side 1246 of cap aperture 1242 is too small for ball 1230 to pass. The interior of cap aperture 1242 has a curved surface 1248 adapted to engage ball 1230. In one embodiment curved surface 1248 has the same radius of curvature as ball 1230. During assembly, ball 1230 is placed into aperture 1222 of housing 1220. Cap 1240 is then secured into aperture 1222 of housing 1220 trapping ball 1230 between cap 1240 and housing 1220 to form a ball-joint (see FIG. 12C). When assembled, ball 1230 can pivot and rotate within a race created by curved surface 1248 of cap 1240 and curved surface 1228 of housing 1220.

Ball 1230 is in the form of a sphere truncated on two opposing sides 1232, 1234. A bore 1236 passes through ball 1230 from side 1232 to side 1234. The walls of bore 1236 are preferably perpendicular to the truncated opposing sides 1232, 1234. Ball 1230 is adapted to receive a smooth shaft of a bone anchor—the shaft is held in place using a separate nut. The bore 1236 is cylindrical and has an internal diameter sized to receive the posterior shaft of a bone anchor to be received in the bore (not shown but see FIG. 11C) and to allow bone anchor rotation. Thus, when secured in place, the shaft of the bone anchor can slide (along the longitudinal axis of the bone anchor) and rotate within bore 1236. Bore 1236 is eccentric in that the axis of bore 1236 does not pass through the center of ball 1230.

FIG. 12B shows an enlarged view of ball 1230 from side 1232. Bore 1236 passes all the way through ball 1230. The axis of bore 1236 is preferably perpendicular to side 1232 (and side 1234, not shown). Bore 1236 is circular and the center axis 1237 of bore 1236 is offset from the center axis 1231 of ball 1230 (the axis passing through the center of ball 1230 perpendicular to sides 1232 and 1234). The offset 1239 is illustrated by a double-headed arrow. In embodiments, the axis of bore 1236 is offset from the center of ball 1230 by preferably 0.5 mm to 2.5 mm. In one preferred embodiment, the axis of bore 1236 is offset from the center of ball 1230 by 1 mm. Because of the offset, rotation of the ball 1230 can move the center axis 1237 of bore 1236 through a range of double the amount of offset 1239. When integrated into adaptive spinal rod 1200, ball 1230 provides a linear range of motion of twice the amount of offset between the rod 1210 and a shaft mounted in bore 1236 achieving results kinematically similar to adaptive spinal rod 1100 of FIGS. 11A-11H.

FIG. 12C shows a fully assembled adaptive spinal rod 1200 in which ball 1230 is positioned between cap 1240 and housing 1220. Aperture 1222 of housing 1220 and cap aperture 1242 of cap 1240 cooperate to from a partially-spherical race 1202 in which ball 1230 is contained or trapped. Although ball 1230 is contained or trapped within race 1202, ball 1230 can pivot and rotate within circular race 1202. In combination, the surface of ball 1230, and the linear race 1202 form a ball-joint.

As shown in FIG. 12C, bore 1236 of ball 1230 is accessible from both sides of the housing 1220 after ball 1230 has been secured between cap 1240 and housing 1220. Bore 1236 of ball 1230 is accessible and configured for mounting adaptive spinal rod 1200 to a bone anchor, for example, the bone anchor shown, in FIG. 11C. The bore 1236 is shown in FIG. 12B to be on the opposite side of race 1202 from rod 1210. However, because ball 1230 can rotate within race 1202, bore 1236 can move closer to rod 1210 by a distance double the offset 1239 to position 1241 (See FIG. 12B).

Materials for Adaptive Spinal Rod

Movement of the adaptive spinal rod relative to the bone anchor provides load sharing and adaptive stabilization properties to the adaptive stabilization assembly. The characteristics of the material of the adaptive spinal rod in combination with the dimensions of the components affect the force-deflection characteristics of the adaptive spinal rod. The dimensions and materials may be selected to achieve the desired force-deflection characteristics.

The adaptive spinal rod and bone anchors are preferably made of biocompatible implantable metals. Components of the adaptive spinal rod are, in some embodiments, made from stainless steel, titanium, titanium alloy and/or cobalt chrome. In preferred embodiments, the bone anchor and adaptive spinal rod are made of titanium alloy; however, other materials, for example, stainless steel may be used instead of or in addition to the titanium components. Furthermore, moving components of the adaptive spinal rod are, in some embodiments, made of cobalt chrome for good wear characteristics.

The particular adaptive stabilization assemblies shown herein are provided by way of example only. It is an aspect of preferred embodiments of the present invention that a range of components be provided and that the components may be assembled in different combinations and organizations to create different assemblies suitable for the functional needs and anatomy of different patients. Also, adaptive spinal rods having different force deflection characteristics may be incorporated at different spinal levels in accordance with the anatomical and functional requirements. Stabilization and load sharing may be provided at one or more motion segments and in some cases stabilization and load sharing may be provided at one or more motion segments in conjunction with fusion at an adjacent motion segment. Particular adaptive stabilization assemblies may incorporate combinations of the bone anchors, adaptive spinal rods, vertical rods, deflection rods, offset and coaxial connectors described herein, described in the related applications incorporated by reference, and also standard spinal stabilization and/or fusion components, for example screws, rods and polyaxial screws.

The foregoing description of preferred embodiments of the present invention has been provided for the purposes of illustration and description. It is not intended to be exhaustive or to limit the invention to the precise forms disclosed. Many embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the claims and their equivalents.

What is claimed is:

1. An adaptive spinal rod adapted to stabilize a spinal segment, wherein the spinal rod comprises:
   an elongated rod having a first end, a second end and a longitudinal rod axis;
   an aperture at the first end of the rod;
   a partially-spherical mount contained in the aperture, the partially-spherical mount can rotate and pivot within the aperture, wherein the partially-spherical mount has a central axis perpendicular to a base side of the partially-spherical mount;
   the partially-spherical mount having an elongated slot adapted to receive a post of a bone anchor, wherein the elongated slot has a first dimension perpendicular to the central axis of the partially-spherical mount and a second dimension parallel to the central axis of the partial-spherical mount,
   wherein the post is loosely coupled to the elongated slot such that the post can slide in the first dimension and the second dimension of the elongated slot, and rotate in the elongated slot; and
   wherein the bone anchor can be secured relative to the partially-spherical mount while permitting the bone anchor to change in angle relative to the longitudinal rod axis.

2. The adaptive spinal rod of claim 1, in combination with a bone anchor, wherein the bone anchor comprises a threaded shaft adapted to engage a vertebra and a post adapted to mount relative to the partially-spherical mount in the elongated slot.

3. The adaptive spinal rod of claim 1, in combination with a first bone anchor and a second bone anchor, wherein:
   the first bone anchor comprises a post and a threaded shaft adapted to engage a vertebra;
   the second bone anchor comprises a head and a threaded shaft adapted to engage a vertebra;
   wherein the partially-spherical mount is secured relative to the post of the first bone anchor; and
   wherein the second end of the elongate rod is secured to the head of the second bone anchor.

4. The adaptive spinal rod of claim 1 wherein the aperture is off-set from said longitudinal rod axis.

5. The adaptive spinal rod of claim 1 wherein said elongated slot of said partially-spherical mount is adapted to allow the post to slide along the elongated slot in a direction about perpendicular to a longitudinal axis of the post.

6. The adaptive spinal rod of claim 1 wherein said aperture is linear such that said partially-spherical mount can move linearly in said linear aperture.

7. The adaptive spinal rod of claim 1, wherein the elongated slot is adapted to allow the bone anchor to at least one of slide, pivot and rotate relative to the elongated slot in the adaptive spinal rod.

8. The adaptive spinal rod of claim 1, wherein the elongated slot is adapted to allow the bone anchor to slide, pivot and rotate relative to the elongated slot in the adaptive spinal rod.

9. An adaptive spinal rod adapted to stabilize a spine, wherein the spinal rod comprises:
   an elongated rod having a first end, a second end, and a longitudinal rod axis;
   a housing at the first end of the rod;
   a rod aperture passing through the housing;
   a race within the rod aperture;

a mount contained by the race and movable relative to the race, the mount can rotate and pivot within the rod aperture, wherein the mount has a central axis perpendicular to a base side of the mount;

an elongated slot passing through the mount and said elongated slot adapted to receive a post, wherein the elongated slot has a first dimension perpendicular to the central axis of the mount and a second dimension parallel to the central axis of the mount, and wherein the post is loosely coupled to the elongated slot such that the post can slide in the first dimension and the second dimension of the elongated slot, and rotate in the elongated slot.

10. The adaptive spinal rod of claim 9 wherein said mount is spherically shaped and said elongated rod is adapted to slide, rotate and pivot relative to said post.

11. The adaptive spinal rod of claim 9, wherein the elongated rod is adapted to slide, rotate and pivot relative to the post.

12. The adaptive spinal rod of claim 9 wherein the aperture is off-set from said longitudinal rod axis.

13. The adaptive spinal rod of claim 9 wherein said elongated slot is adapted to allow the post to slide along the elongated slot in a direction about perpendicular to a longitudinal axis of the post.

14. The adaptive spinal rod of claim 9 wherein said aperture is elongated such that said mount can move linearly in said elongated aperture.

15. The adaptive spinal rod of claim 9 wherein the elongated slot is one of oval, elliptical, rectangular with rounded corners and race track shaped.

16. An adaptive spinal rod adapted to stabilize a spine, wherein the spinal rod comprises:

an elongated rod having a first end, a second end, and a longitudinal rod axis;

an aperture located at the first end of the elongated rod;

a curved mount contained by the aperture, the curved mount can rotate and pivot within the aperture, wherein the curved mount has a central axis perpendicular to a base side of the curved mount;

the curved mount having an elongated slot adapted to receive a post from a bone anchor, wherein the elongated slot has a first dimension perpendicular to the central axis of the curved mount and a second dimension parallel to the central axis of the curved mount; and wherein the post is loosely coupled to the elongated slot such that the post can slide in the first dimension and the second dimension of the elongated slot, and rotate in the elongated slot.

17. The adaptive spinal rod of claim 16 wherein the aperture is off-set from said longitudinal rod axis.

18. The adaptive spinal rod of claim 16 wherein said aperture is linear such that said curved mount can move linearly in said linear aperture.

* * * * *